United States Patent
Dyckman et al.

(10) Patent No.: US 11,059,784 B2
(45) Date of Patent: Jul. 13, 2021

(54) OXIME ETHER COMPOUNDS

(71) Applicant: BRISTOL-MYERS SQUIBB COMPANY, Princeton, NJ (US)

(72) Inventors: Alaric J. Dyckman, Lawrenceville, NJ (US); Ling Li, Pennington, NJ (US); T. G. Murali Dhar, Newtown, PA (US); Hai-Yun Xiao, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/636,662

(22) PCT Filed: Aug. 8, 2018

(86) PCT No.: PCT/US2018/045690
§ 371 (c)(1),
(2) Date: Feb. 5, 2020

(87) PCT Pub. No.: WO2019/032631
PCT Pub. Date: Feb. 14, 2019

(65) Prior Publication Data
US 2021/0147361 A1    May 20, 2021

Related U.S. Application Data

(60) Provisional application No. 62/542,961, filed on Aug. 9, 2017.

(51) Int. Cl.
| | |
|---|---|
| C07D 213/53 | (2006.01) |
| C07D 207/12 | (2006.01) |
| A61P 37/06 | (2006.01) |
| C07D 211/96 | (2006.01) |
| C07D 211/40 | (2006.01) |

(52) U.S. Cl.
CPC ............ *C07D 213/53* (2013.01); *A61P 37/06* (2018.01); *C07D 207/12* (2013.01); *C07D 211/40* (2013.01); *C07D 211/96* (2013.01)

(58) Field of Classification Search
CPC .. C07D 213/53; C07D 207/12; C07D 211/40; C07D 211/96; A61P 37/06
See application file for complete search history.

(56) References Cited

U.S. PATENT DOCUMENTS

| | | | |
|---|---|---|---|
| 3,843,666 A | 10/1974 | Coombs et al. | |
| 5,670,522 A | 9/1997 | Lesson et al. | |
| 6,251,922 B1 | 6/2001 | Jahne et al. | |
| 7,115,545 B1 | 10/2006 | Witschel et al. | |
| 8,492,441 B2 | 7/2013 | Legangneux | |
| 2004/0259904 A1 | 12/2004 | Tong et al. | |
| 2005/0027125 A1 | 2/2005 | Linden et al. | |
| 2007/0281963 A1 | 12/2007 | Fukumoto et al. | |
| 2010/0216762 A1 | 8/2010 | Harris et al. | |
| 2016/0052888 A1* | 2/2016 | Dyckman ............ | A61K 31/351 514/63 |

FOREIGN PATENT DOCUMENTS

| | | |
|---|---|---|
| EP | 223914 A1 | 9/2010 |
| EP | 2592071 A1 | 5/2013 |
| GB | 1354097 | 5/1974 |
| GB | 1354098 | 5/1974 |
| JP | 47016454 | 9/1972 |
| JP | 47022226 | 10/1972 |
| JP | 4899161 | 12/1973 |
| JP | 2004-18489 | 1/2004 |
| WO | WO199725317 A1 | 7/1997 |
| WO | WO199813356 A1 | 4/1998 |
| WO | WO199917769 A1 | 4/1999 |
| WO | WO200027822 A2 | 5/2000 |
| WO | WO200187846 A2 | 11/2001 |
| WO | WO2003061655 A1 | 7/2003 |
| WO | WO2003097609 A1 | 11/2003 |
| WO | WO2003105840 A2 | 12/2003 |
| WO | WO2005095387 A1 | 10/2005 |
| WO | WO2006052555 A2 | 5/2006 |
| WO | WO2008028168 A2 | 3/2008 |
| WO | WO2008039520 A2 | 4/2008 |

(Continued)

OTHER PUBLICATIONS

International Preliminary Report on Patentability PCT/US2018/045690, dated Feb. 11, 2020.

Dinges, et al., "1,4-Dihydroindeno[1,2-c]pyrazoles with Acetylenic Side Chains as Novel and Potent Multitargeted Receptor Tyrosine Kinase Inhibitors with Low Affinity for the hERG Ion Channel", J. Med. Chem., 2007, vol. 50, pp. 2011-2029.

Ho, et al. "(6,7-Dimethoxy-2,4-dihydroindeno[1,2-c]pyrazol-3-yl)phenylamines: Platelet-Derived Growth Factor Receptor Tyrosine Kinase Inhibitors with Broad Antiproliferative Activity against Tumor Cells", J. Med. Chem., 2005, vol. 48, pp. 8163-8173.

(Continued)

*Primary Examiner* — Timothy R Rozof
(74) *Attorney, Agent, or Firm* — Gary Greenblatt

(57) ABSTRACT

Disclosed are compounds of Formula (I): (I) or a salt thereof, wherein: X is CH or N; Y is CH or N; $R_1$ is —OH or —OP(O)(OH)$_2$; L is —CR$_3$=N—O—CR$_a$R$_a$— or CR$_a$R—O—N=CR$_3$; L$_2$ is a bond, —C(O)—, or S(O)$_2$—; and R$_2$, R$_3$, R$_a$, m, and n are defined herein. Also disclosed are methods of using such compounds as selective agonists for G protein coupled receptor S1P1, and pharmaceutical compositions comprising such compounds. These compounds are useful in treating, preventing, or slowing the progression of diseases or disorders in a variety of therapeutic areas, such as autoimmune diseases and vascular disease.

13 Claims, 1 Drawing Sheet

(56) References Cited

FOREIGN PATENT DOCUMENTS

| WO | WO2008053300 A1 | 5/2008 |
| WO | WO2008094896 A1 | 8/2008 |
| WO | WO2008118790 A1 | 10/2008 |
| WO | WO2009078983 A1 | 6/2009 |
| WO | WO2009089305 A1 | 7/2009 |
| WO | WO2009123971 A1 | 10/2009 |
| WO | WO2010011316 A1 | 1/2010 |

OTHER PUBLICATIONS

Kumar, et al., "Efficient Routes to Pyrazolo[3,4-b]indoles and Pyrazolo[1,5-a]benzimidazoles via Palladium- and Copper-Catalyzed Intramolecular C_C and C—N Bond Formation", J. Org. Chem., 2009, vol. 74, pp. 7046-7051.

Marcoux, et al., "Identification of potent tricyclic prodrug S1P1 receptor modulators", MedChemComm, 2017, vol. 8, pp. 725.

Ponomarev, et al., "Nature of the excited states of dialkylamino derivatives of aromatic and heteroaromatic compounds with annelated oxazole rings", Teoreticheskaya i Eksperimental'naya Khimiya, 1990, 26 (6), pp. 644-650.

Ponomarev, et al., "Spin-orbit interaction of the π π*-states in molecules with annelated oxazole rings", Teoreticheskaya i Eksperimental'naya Khimiya, 1990, vol. 26 (4), pp. 403-406.

Rosen, et al., "Discovery of the first known small-molecule inhibitors of heme-regulated eukaryotic initiation factor 2α (HRI) kinase", Bioorganic & Medicinal Chemistry Letters, 2009, vol. 19, pp. 6548-6551.

Shen, et al.,, "Discovery of Novel Tricyclic Full Agonists for the G-Protein-Coupled Niacin Receptor 109A with Minimized Flushing in Rats", J. Med. Chem, 2009, vol. 52, pp. 2587-2602.

Tao, et al., "Discovery of 4'-(1,4-dihydro-indeno[1,2-c]pyrazol-3-yl)-benzonitriles and 4'-(1,4-dihydro-indenol[1,2-c]pyrazol-3-yl)-pyridine-2'-carbonitriles as potent checkpoint kinase (Chk1) inhibitors", Bioorganic & Medicinal Chemistry Letters, 2007, vol. 17, pp. 5944-5951.

* cited by examiner

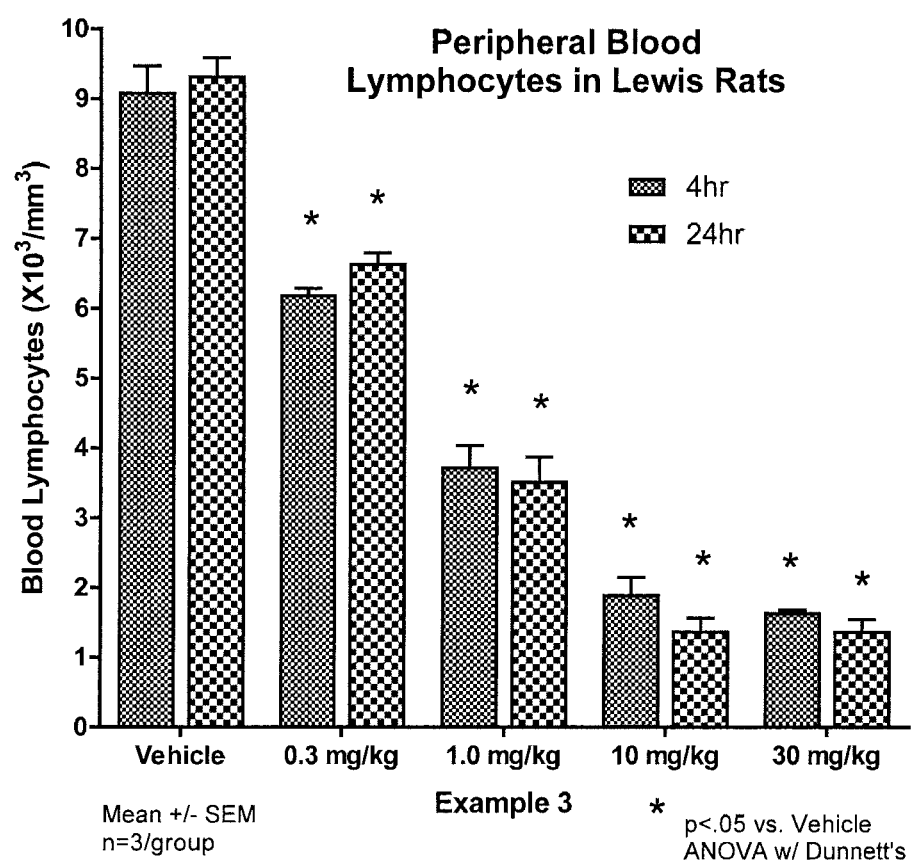

OXIME ETHER COMPOUNDS

CROSS REFERENCE TO RELATED APPLICATIONS

This application is a national phase application under 35 U.S.C. § 371 of International Patent Application No. PCT/US2018/045690, filed Aug. 8, 2018, which claims priority to U.S. Provisional Application No. 62/542,961, filed Aug. 9, 2017, which are expressly incorporated fully herein by reference.

DESCRIPTION

The present invention generally relates to oxime ether compounds useful as $S1P_1$ agonists. Provided herein are oxime ether compounds, compositions comprising such compounds, and methods of their use. The invention further pertains to pharmaceutical compositions comprising at least one compound according to the invention that are useful for the treatment of conditions related to $S1P_1$ agonism, such as autoimmune diseases and vascular disease.

BACKGROUND OF THE INVENTION

Sphingosine-1-phosphate (S1P) has been demonstrated to induce many cellular effects, including those that result in platelet aggregation, cell proliferation, cell morphology, tumor cell invasion, endothelial cell and leukocyte chemotaxis, endothelial cell in vitro angiogenesis, and lymphocyte trafficking. S1P receptors are therefore good targets for a wide variety of therapeutic applications such as tumor growth inhibition, vascular disease, and autoimmune diseases. S1P signals cells in part via a set of G protein-coupled receptors named $S1P_1$ or S1P, $S1P_2$ or $S1P_2$, $S1P_3$ or $S1P_3$, $S1P_4$ or $S1P_4$, and $S1P_5$ or $S1P_5$ (formerly called EDG-1, EDG-5, EDG-3, EDG-6, and EDG-8, respectively).

S1P is important in the entire human body as it is also a major regulator of the vascular and immune systems. In the vascular system, S1P regulates angiogenesis, vascular stability, and permeability. In the immune system, S1P is recognized as a major regulator of trafficking of T- and B-cells. S1P interaction with its receptor $S1P_1$ is needed for the egress of immune cells from the lymphoid organs (such as thymus and lymph nodes) into the lymphatic vessels. Therefore, modulation of S1P receptors was shown to be critical for immunomodulation, and S1P receptor modulators are novel immunosuppressive agents.

The $S1P_1$ receptor is expressed in a number of tissues. It is the predominant family member expressed on lymphocytes and plays an important role in lymphocyte trafficking. Downregulation of the $S1P_1$ receptor disrupts lymphocyte migration and homing to various tissues. This results in sequestration of the lymphocytes in lymph organs thereby decreasing the number of circulating lymphocytes that are capable of migration to the affected tissues. Thus, development of an $S1P_1$ receptor agent that suppresses lymphocyte migration to the target sites associated with autoimmune and aberrant inflammatory processes could be efficacious in a number of autoimmune and inflammatory disease states.

Among the five S1P receptors, $S1P_1$ has a widespread distribution and is highly abundant on endothelial cells where it works in concert with $S1P_3$ to regulate cell migration, differentiation, and barrier function. Inhibition of lymphocyte recirculation by non-selective S1P receptor modulation produces clinical immunosuppression preventing transplant rejection, but such modulation also results in transient bradycardia. Studies have shown that $S1P_1$ activity is significantly correlated with depletion of circulating lymphocytes. In contrast, $S1P_3$ receptor agonism is not required for efficacy. Instead, $S1P_3$ activity plays a significant role in the observed acute toxicity of nonselective S1P receptor agonists, resulting in the undesirable cardiovascular effects, such as bradycardia and hypertension. (See, e.g., Hale et al., *Bioorg. Med. Chem. Lett.*, 14:3501 (2004); Sanna et al., *J. Biol. Chem.*, 279:13839 (2004); Anliker et al., *J. Biol. Chem.*, 279:20555 (2004); Mandala et al., *J. Pharmacol. Exp. Ther.*, 309:758 (2004).)

An example of an $S1P_1$ agonist is FTY720. This immunosuppressive compound FTY720 (JPI 1080026-A) has been shown to reduce circulating lymphocytes in animals and humans, and to have disease modulating activity in animal models of organ rejection and immune disorders. The use of FTY720 in humans has been effective in reducing the rate of organ rejection in human renal transplantation and increasing the remission rates in relapsing remitting multiple sclerosis (see Brinkman et al., *J. Biol. Chem.*, 277:21453 (2002); Mandala et al., *Science*, 296:346 (2002); Fujino et al., *J. Pharmacol. Exp. Ther.*, 305:45658 (2003); Brinkman et al., *Am. J. Transplant.*, 4:1019 (2004); Webb et al., *J. Neuroimmunol.*, 153:108 (2004); Morris et al., *Eur. J. Immunol.*, 35:3570 (2005); Chiba, *Pharmacology & Therapeutics*, 108:308 (2005); Kahan et al., *Transplantation*, 76:1079 (2003); and Kappos et al., *N. Engl. J. Med.*, 335:1124 (2006)). Subsequent to its discovery, it has been established that FTY720 is a prodrug, which is phosphorylated in vivo by sphingosine kinases to a more biologically active agent that has agonist activity at the $S1P_1$, $S1P_3$, $S1P_4$, and $S1P_5$ receptors. It is this activity on the S1P family of receptors that is largely responsible for the pharmacological effects of FTY720 in animals and humans.

Clinical studies have demonstrated that treatment with FTY720 results in bradycardia in the first 24 hours of treatment (Kappos et al., *N. Engl. J. Med.*, 335:1124 (2006)). The observed bradycardia is commonly thought to be due to agonism at the $S1P_3$ receptor. This conclusion is based on a number of cell based and animal experiments. These include the use of $S1P_3$ knockout animals which, unlike wild type mice, do not demonstrate bradycardia following FTY720 administration and the use of $S1P_1$ selective compounds. (Hale et al., *Bioorg. Med. Chem. Lett.*, 14:3501 (2004); Sanna et al., *J. Biol. Chem.*, 279:13839 (2004); and Koyrakh et al., *Am. J. Transplant.*, 5:529 (2005)).

The following applications have described compounds as $S1P_1$ agonists: WO 03/061567 (U.S. Publication No. 2005/0070506), WO 03/062248 (U.S. Pat. No. 7,351,725), WO 03/062252 (U.S. Pat. No. 7,479,504), WO 03/073986 (U.S. Pat. No. 7,309,721), WO 03/105771, WO 05/058848, WO 05/000833, WO 05/082089 (U.S. Publication No. 2007/0203100), WO 06/047195, WO 06/100633, WO 06/115188, WO 06/131336, WO 2007/024922, WO 07/109330, WO 07/116866, WO 08/023783 (U.S. Publication No. 2008/0200535), WO 08/029370, WO 08/114157, WO 08/074820, WO 09/043889, WO 09/057079, WO 2014/130752, WO 2016/028959, and U.S. Pat. No. 6,069,143. Also see Hale et al., *J. Med. Chem.*, 47:6662 (2004).

There still remains a need for compounds useful as $S1P_1$ agonists and yet having selectivity over $S1P_3$.

Applicants have found potent compounds that have activity as $S1P_1$ agonists. Further, applicants have found compounds that have activity as $S1P_1$ agonists and are selective over $S1P_3$. These compounds are provided to be useful as pharmaceuticals with desirable stability, bioavailability, therapeutic index, and toxicity values that are important to their drugability.

SUMMARY OF THE INVENTION

The present invention provides substituted oxime ether compounds of Formula (I), which are useful as modulators of $S1P_1$ activity, including salts thereof.

The present invention also provides pharmaceutical compositions comprising a compound of Formula (I) and/or a pharmaceutically acceptable salt thereof, and a pharmaceutically acceptable carrier.

The present invention also provides a method of treating a disease or disorder associated with the activity of G protein-coupled receptor $S1P_1$, the method comprising administering to a mammalian patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament for the treatment or prophylaxis of $S1P_1$ receptor-related conditions, such as autoimmune and vascular diseases.

The compounds of Formula (I) and compositions comprising the compounds of Formula (I) may be used in treating, preventing, or curing various $S1P_1$ related conditions. Pharmaceutical compositions comprising these compounds are useful in treating, preventing, or slowing the progression of diseases or disorders in a variety of therapeutic areas, such as autoimmune and vascular diseases.

These and other features of the invention will be set forth in expanded form as the disclosure continues.

BRIEF DESCRIPTION OF THE DRAWINGS

The invention is illustrated by reference to the accompanying drawing described below.

FIG. 1 shows the peripheral blood lymphocyte levels in Lewis Rats dosed with Example 3 compared to vehicle.

DETAILED DESCRIPTION

The first aspect of the present invention provides at least one compound of Formula (I):

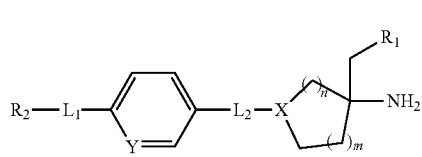

or a salt thereof, wherein:
X is CH or N;
Y is CH or N;
$R_1$ is —OH or —OP(O)(OH)$_2$;
$L_1$ is —CR$_3$=N—O—CR$_a$R$_a$— or —CR$_a$R$_a$—O—N=CR$_3$—;
$L_2$ is a bond, —C(O)—, or —S(O)$_2$—;

$R_2$ is $C_{1-4}$ alkyl, —CH=CH$_2$, $C_{3-6}$ cycloalkyl, —(CH$_2$)$_p$-A, or —CH$_2$O-A;
A is phenyl substituted with zero to 2 substituents independently selected from F, Cl, $C_{1-2}$ alkyl, —CF$_3$, —NO$_2$, —O(C$_{1-2}$ alkyl), and $C_{3-6}$ cycloalkyl;
$R_3$ is H, $C_{1-2}$ alkyl, or —CF$_3$;
each $R_a$ is independently H or —CH$_3$;
m is 1 or 2;
n is 1 or 2; provided that n+m is 2 or 3; and
p is zero, 1, or 2.

In one embodiment, a compound of Formula (I) or a salt thereof is provided wherein $L_1$ is —CR$_3$=N—O—CR$_a$R$_a$—; and X, Y, $L_2$, $R_1$, $R_2$, $R_3$, m, and n are defined in the first aspect. Compounds of this embodiment have the structure of Formula (II):

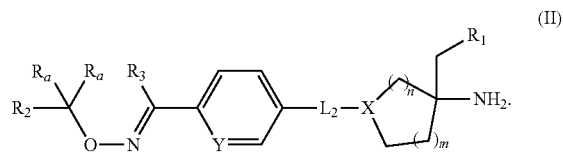

Included in this embodiment are compounds in which $R_1$ is —OH. Also included in this embodiment are compounds in which each $R_a$ is H. Additionally, included in this embodiment are compounds in which $R_1$ is —OP(O)(OH)$_2$.

In one embodiment, a compound of Formula (I) or a salt thereof is provided wherein $L_1$ is —CH$_2$—O—N=CR$_3$—; and X, Y, $L_2$, $R_1$, $R_2$, $R_3$, m, and n are defined in the first aspect. Compounds of this embodiment have the structure of Formula (III):

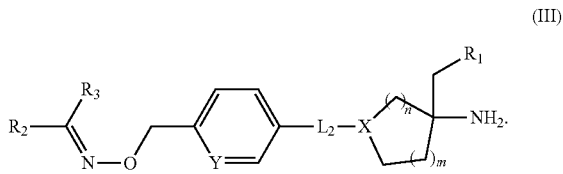

Included in this embodiment are compounds in which $R_1$ is —OH. Also included in this embodiment are compounds in which $R_1$ is —OP(O)(OH)$_2$.

In one embodiment, a compound of Formula (I) or a salt thereof is provided wherein Y is CH; and X, $L_1$, $L_2$, $R_1$, $R_2$, m, and n are defined in the first aspect.

Compounds of this embodiment have the structure of Formula (Ia):

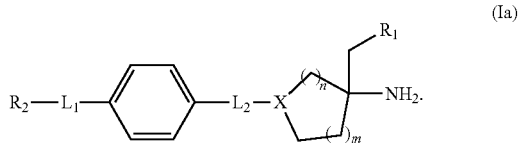

Included in this embodiment are compounds in which $R_1$ is —OH. Also included in this embodiment are compounds in which $R_1$ is —OP(O)(OH)$_2$.

In one embodiment, a compound of Formula (I) or a salt thereof is provided wherein Y is N; and X, $L_1$, $L_2$, $R_1$, $R_2$, m, and n are defined in the first aspect. Compounds of this embodiment have the structure of Formula (Ib):

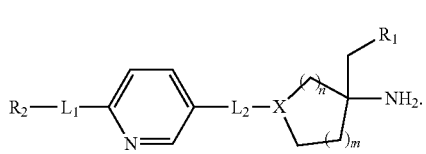

(Ib)

Included in this embodiment are compounds in which $R_1$ is —OH. Also included in this embodiment are compounds in which $R_1$ is —OP(O)(OH)$_2$.

In one embodiment, a compound of Formula (I) or a salt thereof is provided wherein $L_1$ is —CR$_3$—N=O—CR$_a$R$_a$—; Y is CH; and X, $L_2$, $R_1$, $R_2$, $R_3$, m, and n are defined in the first aspect. Compounds of this embodiment have the structure of Formula (IIa):

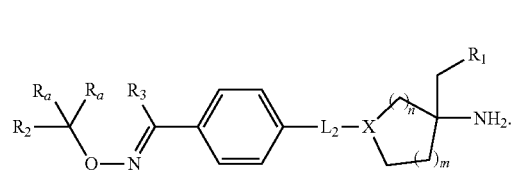

(IIa)

Included in this embodiment are compounds in which $R_1$ is —OH. Also included in this embodiment are compounds in which each $R_a$ is H. Additionally, included in this embodiment are compounds in which $R_1$ is —OP(O)(OH)$_2$.

In one embodiment, a compound of Formula (I) or a salt thereof is provided wherein $L_1$ is —CR$_3$—N=O—CH$_2$—; Y is N; and X, $L_2$, $R_1$, $R_2$, $R_3$, m, and n are defined in the first aspect. Compounds of this embodiment have the structure of Formula (IIb):

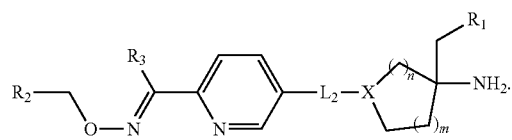

(IIb)

Included in this embodiment are compounds in which $R_1$ is —OH. Also included in this embodiment are compounds in which $R_1$ is —OP(O)(OH)$_2$.

In one embodiment, a compound of Formula (I) or a salt thereof is provided wherein $L_1$ is —CH$_2$—O—N=CR$_3$—; Y is CH; and X, $L_2$, $R_1$, $R_2$, $R_3$, m, and n are defined in the first aspect. Compounds of this embodiment have the structure of Formula (IIIa):

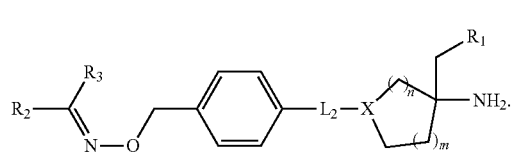

(IIIa)

Included in this embodiment are compounds in which $R_1$ is —OH. Also included in this embodiment are compounds in which $R_1$ is —OP(O)(OH)$_2$.

In one embodiment, a compound of Formula (I) or a salt thereof is provided wherein $L_1$ is —CH$_2$—O—N=CR$_3$—; Y is N; and X, $L_2$, $R_1$, $R_2$, $R_3$, m, and n are defined in the first aspect. Compounds of this embodiment have the structure of Formula (IIIb):

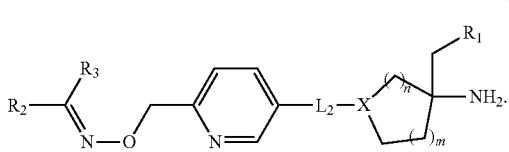

(IIIb)

Included in this embodiment are compounds in which $R_1$ is —OH. Also included in this embodiment are compounds in which $R_1$ is —OP(O)(OH)$_2$.

One embodiment provides a compound of Formula (I) or a salt thereof, wherein $R_1$ is —OH.

One embodiment provides a compound of Formula (I) or a salt thereof, wherein $R_1$ is —OP(O)(OH)$_2$.

One embodiment provides a compound of Formula (I) or a salt thereof, wherein $L_2$ is a bond; and X, Y, $L_1$, $R_1$, $R_2$, m, and n are defined in the first aspect. Included in this embodiment are compounds in which m+n is 2. Also included in this embodiment are compounds in which X is CH.

One embodiment provides a compound of Formula (I) or a salt thereof, wherein $L_2$ is a bond; Y is CH; and X, $L_1$, $R_1$, $R_2$, m, and n are defined in the first aspect. Included in this embodiment are compounds in which m+n is 2. Also included in this embodiment are compounds in which X is CH.

One embodiment provides a compound of Formula (I) or a salt thereof, wherein $L_2$ is —C(O)— or —S(O)$_2$—; and X, Y, $L_1$, $R_1$, $R_2$, m, and n are defined in the first aspect. Included in this embodiment are compounds in which X is N. Also included are compounds in which Y is CH.

One embodiment provides a compound of Formula (I) or a salt thereof, wherein $L_2$ is —C(O)—; and X, Y, $L_1$, $R_1$, $R_2$, m, and n are defined in the first aspect. Included in this embodiment are compounds in which X is N. Also included are compounds in which Y is CH.

One embodiment provides a compound of Formula (I) or a salt thereof, wherein $L_2$ is —S(O)$_2$—; and X, Y, $L_1$, $R_1$, $R_2$, m, and n are defined in the first aspect. Included in this embodiment are compounds in which X is N. Also included are compounds in which Y is CH.

One embodiment provides a compound of Formula (I) or a salt thereof, wherein each $R_a$ is H.

One embodiment provides a compound of Formula (I) or a salt thereof, wherein each $R_a$ is —CH$_3$.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_2$ is $C_{1-4}$ alkyl. Included in this embodiment are compounds in which $R_2$ is $C_{2-4}$ alkyl. Also included in this embodiment are compounds in which $R_2$ is ethyl, n-propyl, or n-butyl.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_2$ is $C_{3-6}$ cycloalkyl. Included in this embodiment are compounds in which $R_2$ is cyclopropyl and cyclohexyl.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_2$ is $C_{1-4}$ alkyl or $C_{3-6}$ cycloalkyl. Included in this embodiment are compounds in which $R_2$ is ethyl, n-propyl, n-butyl, or $C_{3-6}$ cycloalkyl. Also included in this embodiment are compounds in which $R_2$ is n-propyl, cyclopropyl, or cyclohexyl.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_2$ is —(CH$_2$)$_p$-A; A is phenyl substituted with zero to 2 substituents independently selected from F, $C_1$, $C_{1-2}$ alkyl, —CF$_3$, —NO$_2$, —O(C$_{1-2}$ alkyl), and $C_{3-6}$ cycloalkyl; and p is zero, 1, or 2. Included in the embodiment are compounds in which A is phenyl substituted with zero to 2 substituents independently selected from F, —CF$_3$, —NO$_2$, —OCH$_3$, and cyclohexyl.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_2$ is —CH$_2$O-A; and A is phenyl substituted with zero to 2 substituents independently selected from F, $C_1$, $C_{1-2}$ alkyl, —CF$_3$, —NO$_2$, —O(C$_{1-2}$ alkyl), and $C_{3-6}$ cycloalkyl. Included in the embodiment are compounds in which A is phenyl substituted with zero to 2 substituents independently selected from F, —CF$_3$, —NO$_2$, —OCH$_3$, and cyclohexyl.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_2$ is —(CH$_2$)$_p$-A or —CH$_2$O-A; A is phenyl substituted with zero to 2 substituents independently selected from F, $C_1$, $C_{1-2}$ alkyl, —CF$_3$, —NO$_2$, —O(C$_{1-2}$ alkyl), and $C_{3-6}$ cycloalkyl; and p is zero, 1, or 2. Included in the embodiment are compounds in which A is phenyl substituted with zero to 2 substituents independently selected from F, —CF$_3$, —NO$_2$, —OCH$_3$, and cyclohexyl.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_2$ is —CH$_2$CH$_2$CH$_3$, $C_{3-6}$ cycloalkyl, —(CH$_2$)$_p$-A, or —CH$_2$O-A; A is phenyl substituted with zero to 2 substituents independently selected from F, —CF$_3$, —NO$_2$, —OCH$_3$, and cyclohexyl; and p is zero, 1, or 2.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_3$ is H.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_3$ is $C_{1-2}$ alkyl. Included in this embodiment are compounds in which $R_3$ is —CH$_3$. Also included in this embodiment are compounds in which $R_3$ is —CH$_2$CH$_3$.

One embodiment provides a compound of Formula (I), Formula (Ia), Formula (Ib), Formula (II), Formula (IIa), Formula (IIb), Formula (III), Formula (IIIa), or Formula (IIIb), or a salt thereof, wherein $R_3$ is $C_{1-2}$ alkyl or —CF$_3$. Included in this embodiment are compounds in which $R_3$ is —CF$_3$.

One embodiment provides a compound of Formula (I) or a salt thereof, wherein X is CH; Y is CH or N; $R_1$ is —OH or —OP(O)(OH)$_2$; $L_1$ is —CR$_3$=N—O—CH$_2$— or —CH$_2$—O—N=CR$_3$—; $L_2$ is a bond; $R_2$ is —CH$_2$CH$_2$CH$_3$, cyclopropyl, cyclohexyl, —(CH$_2$)$_p$-A, or —CH$_2$O-A; A is phenyl substituted with zero to 2 substituents independently selected from F, —CF$_3$, —NO$_2$, —OCH$_3$, and cyclohexyl; $R_3$ is H or —CH$_3$; m is 1; n is 1; and p is zero, 1, or 2. Included in this embodiment are compounds in which $L_1$ is —CR$_3$=N—O—CH$_2$—. Also included in this embodiment are compounds in which $L_1$ is —CH$_2$—O—N=CR$_3$—.

One embodiment provides a compound of Formula (I) or a salt thereof, wherein X is N; Y is CH; $R_1$ is —OH or —OP(O)(OH)$_2$; $L_1$ is —CR$_3$=N—O—CH$_2$—; $L_2$ is —C(O)— or —S(O)$_2$—; $R_2$ is —(CH$_2$)$_p$-A; A is phenyl substituted with zero to 2 substituents independently selected from —CF$_3$ and cyclohexyl; $R_3$ is $C_{1-2}$ alkyl or —CF$_3$; m is 1 or 2; n is 1 or 2; provided that n+m is 2 or 3; and p is zero, 1, or 2. Included in this embodiment are compounds in which n+m is 2. Also included in this embodiment are compounds in which n+m is 3.

One embodiment provides a compound of Formula (I) or a salt thereof, wherein said compound is 1-(4-(3-amino-3-(hydroxymethyl)cyclopentyl)phenyl)ethanone O-phenethyl oxime (1-4); 1-(4-((1R,3R)-3-amino-3-(hydroxymethyl)cyclopentyl)phenyl) ethanone O-benzyl oxime, TFA (5); 1-(4-((1R,3R)-3-amino-3-(hydroxymethyl) cyclopentyl)phenyl) ethan-1-one O-cyclopropylmethyl oxime (6); (E)-1-(4-((1R,3R)-3-amino-3-(hydroxymethyl)cyclopentyl)phenyl)ethan-1-one O-(4-cyclohexyl-3-(trifluoromethyl)benzyl) oxime (7); 1-(4-((1R,3R)-3-amino-3-(hydroxymethyl) cyclopentyl)phenyl)ethan-1-one O-(3-phenylpropyl) oxime (8); 1-(4-((1R,3R)-3-amino-3-(hydroxymethyl)cyclopentyl)phenyl) ethan-1-one O-(4-nitrobenzyl) oxime (9); 1-(4-((1R,3R)-3-amino-3-(hydroxymethyl)cyclopentyl)phenyl)ethan-1-one O-(4-fluorobenzyl) oxime (10); 1-(4-((1R,3R)-3-amino-3-(hydroxymethyl)cyclopentyl)phenyl)ethan-1-one O-cyclohexylmethyl oxime (11); 1-(4-((1S,3R)-3-amino-3-(hydroxymethyl)cyclopentyl) phenyl)ethan-1-one O-(3-methoxybenzyl) oxime (12); 1-(4-((1S,3R)-3-amino-3-(hydroxymethyl)cyclopentyl)phenyl)ethan-1-one O-(2-methoxybenzyl) oxime (13); 1-(4-((1S,3R)-3-amino-3-(hydroxymethyl)cyclopentyl)phenyl)ethan-1-one O-butyl oxime (14); (E)-acetophenone O-(4-((1R,3R)-3-amino-3-(hydroxymethyl)cyclopentyl)benzyl) oxime, TFA (15); (E)-1-phenylethan-1-one O-(4-((1S,3R)-3-amino-3-(hydroxymethyl) cyclopentyl)benzyl) oxime (16); (E)-1-(3-methoxyphenyl)ethan-1-one O-(4-((1S,3R)-3-amino-3-(hydroxymethyl) cyclopentyl)benzyl) oxime (17); (E)-3-methoxybenzaldehyde O-(4-((1S,3R)-3-amino-3-(hydroxymethyl)cyclopentyl)benzyl) oxime (18); ethyl 4-(6-acetylpyridin-3-yl)-1-aminocyclopent-2-enecarboxylate (19-20); (3-amino-3-(hydroxymethyl)pyrrolidin-1-yl) (4-(1-(phenethoxyimino)ethyl)phenyl) methanone (21 and 22); (3-amino-3-(hydroxymethyl)pyrrolidin-1-yl)(4-(1-((3-phenylpropoxy)imino) ethyl)phenyl)methanone, TFA (23 and 24); (3-amino-3-(hydroxymethyl)pyrrolidin-1-yl) (4-(1-(((4-cyclohexyl-3-(trifluoromethyl) benzyl)oxy)imino) ethyl)phenyl)methanone (25-26); (3-amino-3-(hydroxymethyl)pyrrolidin-1-yl)(4-(1-((3-phenylpropoxy)imino) propyl) phenyl)methanone (27-28); (3-amino-3-(hydroxymethyl)piperidin-1-yl)(4-(1-((3-phenylpropoxy)imino)ethyl) phenyl)methanone (29-30); (3-amino-3-(hydroxymethyl) piperidin-1-yl)(4-(1-(((4-cyclohexyl-3-(trifluoromethyl) benzyl)oxy)imino)ethyl)phenyl) methanone (31-32); (3-amino-3-(hydroxymethyl)piperidin-1-yl)(4-(1-

(phenethoxyimino) ethyl)phenyl) methanone (33); (4-amino-4-(hydroxymethyl)piperidin-1-yl)(4-(1-((3-phenylpropoxy)imino)ethyl) phenyl)methanone (34); (3-amino-3-(hydroxymethyl) pyrrolidin-1-yl)(4-(2,2,2-trifluoro-1-((3-phenylpropoxy) imino)ethyl)phenyl)methanone (35); (E)-1-(4-((4-amino-4-(hydroxymethyl)piperidin-1-yl)sulfonyl) phenyl)ethanone O-(3-phenylpropyl)oxime, TFA (36); 1-(4-((4-amino-4-(hydroxymethyl)piperidin-1-yl) sulfonyl) phenyl)ethan-1-one O-(4-cyclohexyl-3-(trifluoromethyl) benzyl) oxime (37); (E)-1-(4-(3-amino-3-(hydroxymethyl) cyclopentyl)phenyl)ethan-1-one O-phenethyl oxime (74); (E)-1-(4-((1S,3R)-3-amino-3-(hydroxymethyl)cyclopentyl) phenyl)ethan-1-one O-(3-phenylpropyl) oxime (75); (E)-1-(4-((1R,3R)-3-amino-3-(hydroxymethyl)cyclopentyl) phenyl)ethan-1-one O-(4-(trifluoromethyl)benzyl) oxime (76); (E)-1-(4-((1R,3R)-3-amino-3-(hydroxymethyl)cyclopentyl) phenyl)ethan-1-one O-(2-phenoxyethyl) oxime (77); (E)-1-(4-((1R,3R)-3-amino-3-(hydroxymethyl)cyclopentyl) phenyl)ethan-1-one O-(2-(3-(trifluoromethyl)phenoxy)ethyl) oxime (78); (E)-1-(4-((1R,3R)-3-amino-3-(hydroxymethyl) cyclopentyl)phenyl)ethan-1-one O-allyl oxime (79); (E)-1-(4-((1R,3R)-3-amino-3-(hydroxymethyl)cyclopentyl)phenyl)ethan-1-one O-isopropyl oxime (80); (E)-1-(4-((1R,3R)-3-amino-3-(hydroxymethyl)cyclopentyl)phenyl) ethan-1-one O-(tert-butyl) oxime (81); (E)-1-(4-((1R,3R)-3-amino-3-(hydroxymethyl) cyclopentyl)phenyl)ethan-1-one O-(3-fluorobenzyl) oxime (82); (E)-1-(4-((1R,3R)-3-amino-3-(hydroxymethyl) cyclopentyl)phenyl)ethan-1-one O-phenyl oxime (83); (E)-1-(4-((1R,3R)-3-amino-3-(hydroxymethyl) cyclopentyl)phenyl)ethan-1-one O-(3-methoxybenzyl) oxime (84); (E)-1-(4-((1R,3R)-3-amino-3-(hydroxymethyl) cyclopentyl) phenyl)ethan-1-one O-(4-methoxybenzyl) oxime (85); (E)-1-(4-((1R,3R)-3-amino-3-(hydroxymethyl) cyclopentyl) phenyl)ethan-1-one O-(3-(trifluoromethyl)benzyl) oxime (86); (E)-1-(4-((1R,3R)-3-amino-3-(hydroxymethyl)cyclopentyl)phenyl)ethan-1-one O-(2-methoxybenzyl) oxime (87); or (4-amino-4-(hydroxymethyl)piperidin-1-yl)(4-(1-(((4-cyclohexyl-3-(trifluoromethyl)benzyl)oxy)imino)ethyl)phenyl)methanone (88).

One embodiment provides a compound of Formula (I) or a salt thereof, wherein said compound is ((1R,3R)-1-amino-3-(4-(1-((cyclopropylmethoxy)imino)ethyl)phenyl) cyclopentyl) methyl dihydrogen phosphate (38); ((1R,3R)-1-amino-3-(4-(1-((benzyloxy) imino)ethyl)phenyl) cyclopentyl)methyl dihydrogen phosphate (39); ((1R,3R)-1-amino-3-(4-((E)-1-(((4-cyclohexyl-3-(trifluoromethyl) benzyl)oxy)imino)ethyl)phenyl)cyclopentyl) methyl dihydrogen phosphate (40); ((1R,3R)-1-amino-3-(4-((E)-1-((3-phenylpropoxy) imino)ethyl)phenyl)cyclopentyl) methyl dihydrogen phosphate (41); ((1R,3R)-1-amino-3-(4-(1-(((4-nitrobenzyl)oxy)imino)ethyl)phenyl)cyclopentyl) methyl dihydrogen phosphate (42); ((1R,3R)-1-amino-3-(4-(1-(((4-fluorobenzyl)oxy)imino)ethyl)phenyl) cyclopentyl) methyl dihydrogen phosphate (43); ((1R,3R)-1-amino-3-(4-(1-(((4-fluorobenzyl)oxy) imino)ethyl)phenyl)cyclopentyl) methyl dihydrogen phosphate (44); ((1R,3R)-1-amino-3-(4-(1-(((4-(trifluoromethyl)benzyl)oxy)imino)ethyl)phenyl) cyclopentyl)methyl dihydrogen phosphate (45); ((1R,3R)-1-amino-3-(4-(1-((2-phenoxyethoxy)imino)ethyl) phenyl) cyclopentyl) methyl dihydrogen phosphate (46); ((1R,3R)-1-amino-3-(4-(1-((2-(3-(trifluoromethyl)phenoxy)ethoxy) imino)ethyl)phenyl) cyclopentyl)methyl dihydrogen phosphate (47); ((1R,3R)-1-amino-3-(4-(1-(((3-fluorobenzyl)oxy)imino)ethyl)phenyl) cyclopentyl) methyl dihydrogen phosphate (48); ((1R,3R)-1-amino-3-(4-((E)-1-(((2-methoxybenzyl)oxy)imino)ethyl)phenyl)cyclopentyl) methyl dihydrogen phosphate (49); ((1R,3R)-1-amino-3-(4-((E)-1-(((3-methoxybenzyl) oxy)imino)ethyl)phenyl)cyclopentyl) methyl dihydrogen phosphate (50); ((1R,3R)-1-amino-3-(4-((E)-1-(((3-(trifluoromethyl) benzyl)oxy)imino) ethyl)phenyl)cyclopentyl) methyl dihydrogen phosphate (51); ((1R,3S)-1-amino-3-(4-(((((E)-1-(3-methoxyphenyl) ethylidene)amino)oxy)methyl) phenyl) cyclopentyl)methyl dihydrogen phosphate (52); ((1R,3S)-1-amino-3-(4-(((((E)-1-(3-methoxyphenyl)ethylidene)amino) oxy)methyl) phenyl)cyclopentyl)methyl dihydrogen phosphate (53); ((1R, 3S)-1-amino-3-(4-(((((E)-1-(3-methoxyphenyl) ethylidene) amino)oxy)methyl) phenyl)cyclopentyl) methyl dihydrogen phosphate (54); (3-amino-1-(4-(1-(phenethoxyimino)ethyl) benzoyl) pyrrolidin-3-yl)methyl dihydrogen phosphate (55); (4-amino-1-(4-(1-(phenethoxyimino) ethyl)benzoyl)piperidin-4-yl)methyl dihydrogen phosphate (56); (4-amino-1-(4-(1-((3-phenylpropoxy)imino)ethyl)benzoyl) piperidin-4-yl) methyl dihydrogen phosphate (57); (E)-(4-amino-1-(4-(1-(((4-cyclohexyl-3-(trifluoromethyl)benzyl)oxy)imino)ethyl) benzoyl)piperidin-4-yl)methyl dihydrogen phosphate (58); (E)-(3-amino-1-(4-(1-(((4-cyclohexyl-3-(trifluoromethyl) benzyl)oxy) imino)ethyl) benzoyl)pyrrolidin-3-yl)methyl dihydrogen phosphate (59-60); (E)-(3-amino-1-(4-(1-((3-phenylpropoxy)imino)ethyl) benzoyl)pyrrolidin-3-yl) methyl dihydrogen phosphate (61-62); (E)-(3-amino-1-(4-(1-((3-phenylpropoxy)imino)propyl) benzoyl)pyrrolidin-3-yl) methyl dihydrogen phosphate (63-64); (Z)-(3-amino-1-(4-(2,2,2-trifluoro-1-((3-phenylpropoxy)imino)ethyl) benzoyl) pyrrolidin-3-yl)methyl dihydrogen phosphate (65); (E)-(3-amino-1-(4-(1-(((4-cyclohexyl-3-(trifluoromethyl) benzyl)oxy) imino)ethyl) benzoyl)piperidin-3-yl)methyl dihydrogen phosphate (66-67); (E)-(3-amino-1-(4-(1-((3-phenylpropoxy)imino)ethyl)benzoyl) piperidin-3-yl)methyl dihydrogen phosphate (68-69); (E)-(4-amino-1-((4-(1-(((4-cyclohexyl-3-(trifluoromethyl)benzyl)oxy) imino)ethyl) phenyl)sulfonyl)piperidin-4-yl) methyl dihydrogen phosphate (70); (E)-(4-amino-1-((4-(1-((3-phenylpropoxy) imino) ethyl)phenyl)sulfonyl)piperidin-4-yl)methyl dihydrogen phosphate (71); or ((1R,3R)-1-amino-3-(4-((E)-1-(phenethoxyimino)ethyl) phenyl)cyclopentyl)methyl dihydrogen phosphate (72-73).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist to $S1P_1$, or effective to treat or prevent autoimmune and/or inflammatory disease states, such as multiple sclerosis and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease. Thus it has been observed that therapeutic agents which act on the immune system or certain cell types of the immune system (such as B-lymphocytes, and T lymphocytes, T cells) may have utility in more than one autoimmune disease.

It is well recognized in the art, including the literature references cited herein, that S1P receptors are good targets for a wide variety of therapeutic applications, including autoimmune diseases. S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other processes. Therefore, compounds that act on some S1P receptor family members while having diminished or no activity at other family members are desirable and are expected to provide a therapeutic effect with an improved side effect profile (i.e., reduction or elimination of unwanted side effects).

As used herein, the term "agonist" in reference to $S1P_1$ refers to an agent which exerts pharmacological effects such as decreased motility of T cells, decreased trafficking of T cells, or decreased egress of T cells from lymphoid tissues. (Rosen et al., Trends in Immunology, 28:102 (2007)).

By virtue of their $S1P_1$ activity as agonists, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy, and asthma.

More particularly, the compounds of the present invention are useful to treat or prevent a disease or disorder selected from the group consisting of transplantation of organs or tissue, graft-versus-host diseases brought about by transplantation, autoimmune syndromes including rheumatoid arthritis, juvenile idiopathic arthritis, systemic lupus erythematosus, cutaneous lupus erythematosus (discoid lupus erythematosus, subacute lupus erythematosus) and lupus nephritis, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, psoriatic arthritis, atopic dermatitis, contact dermatitis, eczematous dermatitis, seborrheic dermatitis, lichen planus, pemphigus, bullous pemphigoid, epidermolysis bullosa, urticaria, angioedemas, vasculitis including ANCA-associated vasculitis, giant cell arteritis, Takayasu's arteritis, microscopic poliangiitis, central nervous system vasculitis, Churg-Strauss Syndrome, and rheumatoid vasculitis, erythema, cutaneous eosinophilia, acne, alopecia areata, keratoconjunctivitis, vernal conjunctivitis, uveitis associated with Behcet's disease, keratitis, herpetic keratitis, conical cornea, dystrophia epithelialis comeae, comeal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, neuropathic pain, chronic bacterial infection, thrombocytopenia, IgA nephropathy, mesangioproliferative glomerulonephritis, IgG4-related disease, ankylosing spondylitis, and relapsing polychondritis. Juvenile idiopathic arthritis includes oligoarthritis-onset juvenile idiopathic arthritis, polyarthritis-onset juvenile idiopathic arthritis, systemic-onset juvenile idiopathic arthritis, juvenile psoriatic arthritis, and enthesitis-related juvenile idiopathic arthritis.

One embodiment provides a method for treating autoimmune and/or inflammatory diseases, comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of autoimmune and/or inflammatory diseases. In another embodiment, provided is the use of the compounds of Formula (I) or pharmaceutically acceptable salts thereof, for the manufacture of a medicament for the treatment or prophylaxis of autoimmune and/or inflammatory disease. A therapeutically effective amount may be employed in these embodiments. Preferably, in these embodiments, the autoimmune and inflammatory diseases are selected from multiple sclerosis, rheumatoid arthritis, inflammatory bowel disease (including Crohn's disease and ulcerative colitis), psoriasis, and as an agent to prevent the rejection of transplanted organs. The method of the present embodiment includes administration of a therapeutically effect amount of a compound of Formula (I) or a pharmaceutically effective salt thereof.

In another embodiment, a method for treating vascular disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of vascular disease. In another embodiment, provided is the use of the compounds of Formula (I) or pharmaceutically acceptable salts thereof, for the manufacture of a medicament for treatment of vascular disease. A therapeutically effective amount may be employed in these embodiments. Preferably, in these embodiments, the vascular disease is selected from atherosclerosis and ischemia reperfusion injury.

In another embodiment, a method for treating inflammatory bowel disease is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of inflammatory bowel disease. In another embodiment, provided is the use of the compounds of Formula (I) or pharmaceutically acceptable salts thereof, for the manufacture of a medicament for treatment of inflammatory bowel disease. A therapeutically effective amount may be employed in these embodiments. Preferably, in these embodiments, the inflammatory bowel disease is selected from Crohn's disease, ulcerative colitis, collagenous colitis, lymphocytic colitis, ischaemic colitis, diversion colitis, Behçet's disease, and indeterminate colitis.

In another embodiment, a method for treating lupus is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of lupus. In another embodiment, provided is the use of the compounds of Formula (I) or pharmaceutically acceptable salts thereof, for the manufacture of a medicament for treatment of lupus. A therapeutically effective amount may be employed in these embodiments. Lupus includes systemic lupus erythematosus, cutaneous lupus erythematosus, discoid lupus erythematosus, subacute lupus erythematosus and lupus nephritis.

In another embodiment, a method for treating multiple sclerosis is provided comprising administering to a mammal in need thereof at least one compound of Formula (I) or a pharmaceutically acceptable salt thereof. Another embodiment provides the compounds of Formula (I) or pharmaceutically acceptable salts thereof, for use in therapy for the treatment of multiple sclerosis. In another embodiment, provided is the use of the compounds of Formula (I) or pharmaceutically acceptable salts thereof, for the manufacture of a medicament for treatment of multiple sclerosis. A therapeutically effective amount may be employed in these embodiments. Preferably, in these embodiments, multiple sclerosis includes relapsing remitting multiple sclerosis, primary progressive multiple sclerosis, secondary progressive multiple sclerosis, and progressive relapsing multiple sclerosis.

The methods of treating S1P1-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to act as an agonist at the S1P1 receptor. The combination of compounds is preferably a synergistic combination. Synergy, as described, for example, by Chou et al., *Adv. Enzyme Regul.*, 22:27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased efficacy, or some other beneficial effect of the combination compared with the individual components.

Exemplary of such other therapeutic agents include corticosteroids or glucocorticoids such as dexamethasone, methylprednisolone, prednisolone, and prednisone; PDE4 inhibitors such as rolipram, cilomilast, roflumilast, and oglemilast; cytokine-suppressive anti-inflammatory drugs (CSAIDs) and inhibitors of p38 kinase, 4-substituted imidazo [1,2-A]quinoxalines as disclosed in U.S. Pat. No. 4,200,750; antibodies or fusion proteins directed to cell surface molecules such as CD2, CD3, CD4, CD8, CD20 such as RITUXAN®, CD25, CD30, CD40, CD69, CD80 (B7.1), CD86 (B7.2), CD90, CTLA, for example abatacept (ORENCIA®), belatacept, or their ligands including CD154 (GP39, or CD40L); antibodies to, fusion proteins, or soluble receptors of human cytokines or growth factors, for example, TNF such as, infliximab (REMICADE®), etanercept (Embrel), adalimumab (HUMIRA®), LT, Il-1 such as anakinra (KINERET®) (an IL-1 receptor antagonist), IL-2, IL-4, IL-5, Il-6, such as CNTO 328 (a chimeric anti-IL-6 antibody), Il-7, Il-8, Il-12, Il-15, Il-16, Il-17, Il-21, Il-23 such as Ustekinumab (a human anti-IL-12/23 monoclonal antibody), and interferons such as interferon beta 1a (AVONEX®, REBIF®), interferon beta 1b (BETASERON®); integrin receptor antagonists such as TYSABRI®; polymeric agents such as glatiramer acetate (COPAXONE®); sulfasalazine, mesalamine, hydroxychloroquine, non-steroidal antiinflammatory drugs (NSAIDs) such as salicylates including aspirin, salsalate, and magnesium salicylate, and non-salicylates such as, ibuprofen, naproxen, meloxicam, celecoxib and rofecoxib; antiviral agents such as abacavir; antiproliferative agents such as methotrexate, mercaptopurine, leflunomide, cyclosporine, mycophenololate, FK506 (tacrolimus, PROGRAF®); cytotoxic drugs such as azathioprine and cyclophosphamide; nuclear translocation inhibitors, such as deoxyspergualin (DSG); gold containing products such as auronofin; penicllamine, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a desired compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

Scheme 1 illustrates methods for the preparation of examples of Formula (II). 1-Amino-3-(4-bromophenyl)cyclopentane-1-carboxylates (1) can be transformed to (1-amino-3-(4-bromophenyl)cyclopentyl)methanol (2) through treatment with various reducing agents and the resulting amino alcohol can be protected to give 3. Conversion to ketone 4 can be achieved through coupling with tributyl(1-ethoxyvinyl)stannane and acidic hydrolysis of the resulting adduct. Treatment of 4 with hydroxylamines provides the oxime ethers 5 which are converted to the desired final products via deprotection of the cyclic carbamate. In an alternative sequence, 1 is first converted to the oxime ethers 8 under conditions similar to the above and the ester is then reduced to afford 6. The starting material 1 (representing four possible stereoisomers) can be used as a mixture of isomers, with the isomers being separated along the way, or at the final product stage or the starting material 1 can be obtained in homochiral form and carried forth as such to afford final products as single stereoisomers.

SCHEME 1

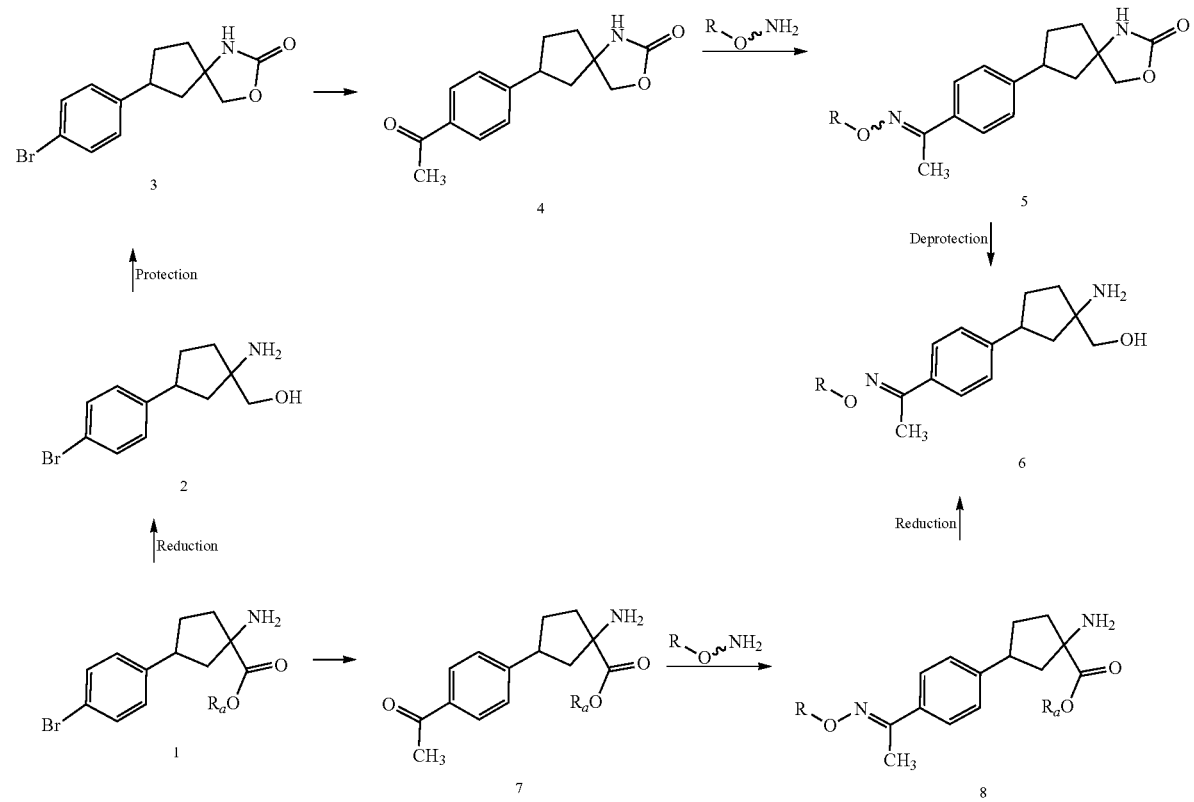

Scheme 2 illustrates a method for the preparation of examples of Formula (III). Carbonylation of 1, followed by treatment under reducing conditions can lead to diol 10. Protection of the 1,2-aminoalcohol as a cyclic carbamate (11) permits the amination of the hydroxymethyl group to afford ethanolamine 12. Condensation with carbonyl compounds and subsequent deprotection of the carbamate leads to the target oxime ether compounds 14.

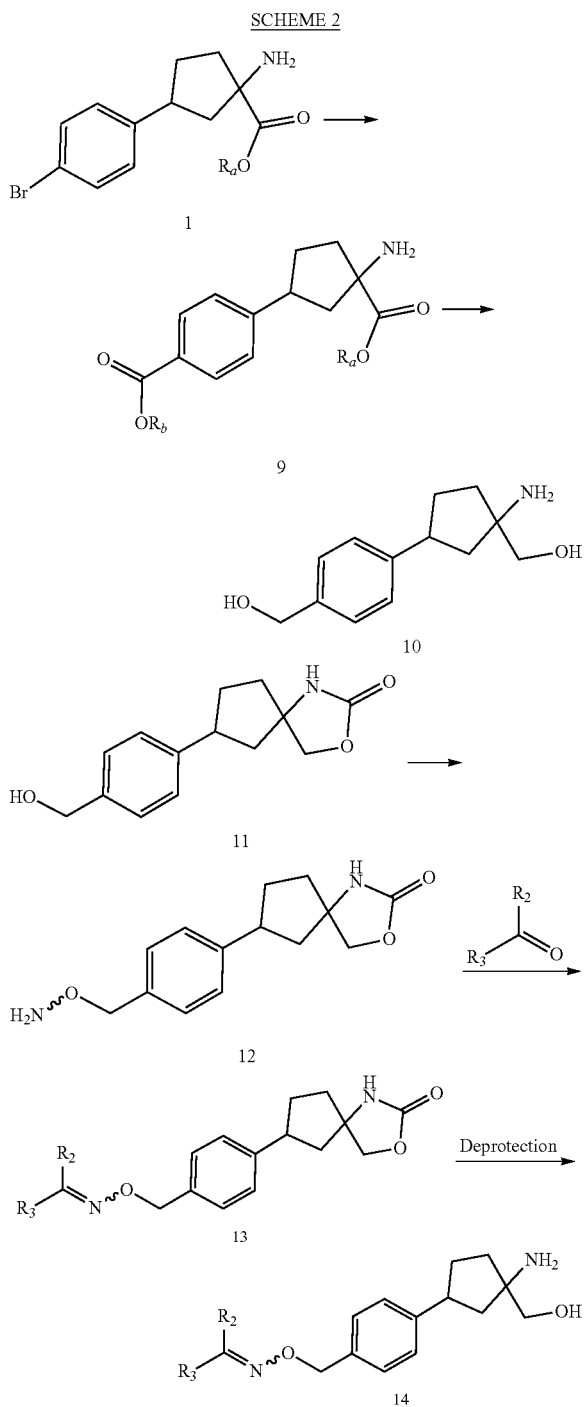

Scheme 3 illustrates one method for the preparation of piperidinyl carboxamide compounds of Formula (I). Transition metal mediated cross-coupling of p-bromobenzoic acid with tributyl(1-ethoxyvinyl)stannane, followed by hydrolysis of the resulting product affords 4-acetylbenzoic acid. Amidation of (4-aminopiperidin-4-yl)methanol and condensation with alkoxyamines provides compounds of Formula (I). Selective phosphorylation of the alcohol can be accomplished with pyrophosphoryl chloride.

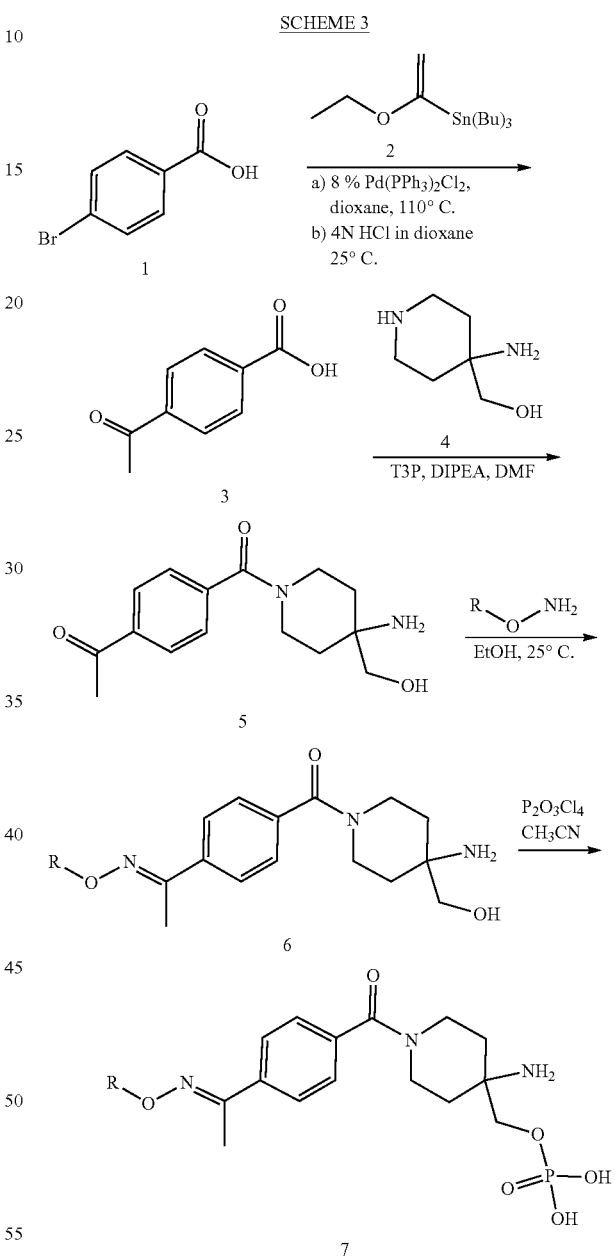

Scheme 4 illustrates one method for the preparation of pyrrolidinyl carboxamide compounds of Formula (I). Amidation of 3-((tert-butoxycarbonyl)amino)pyrrolidine-3-carboxylic acid with p-bromobenzoyl chloride, esterification with concomitant removal of the BOC protecting group through treatment with methanolic HCl and reduction of the ester with NaBH$_4$ provides 12. Stille coupling, hydrolysis, condensation with alkoxyamines, and phosphorylation proceed as described for Scheme 1.

SCHEME 4

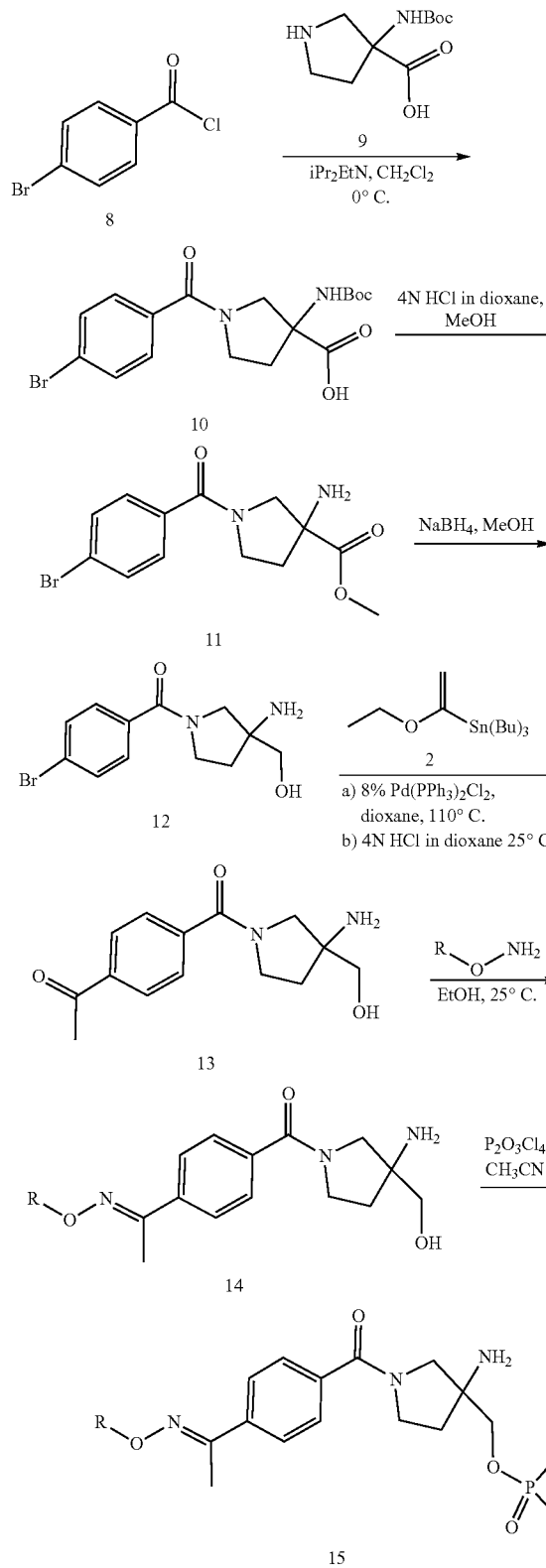

dines, condensation with alkoxyamines, and phosphorylation as described for Scheme 3.

SCHEME 5

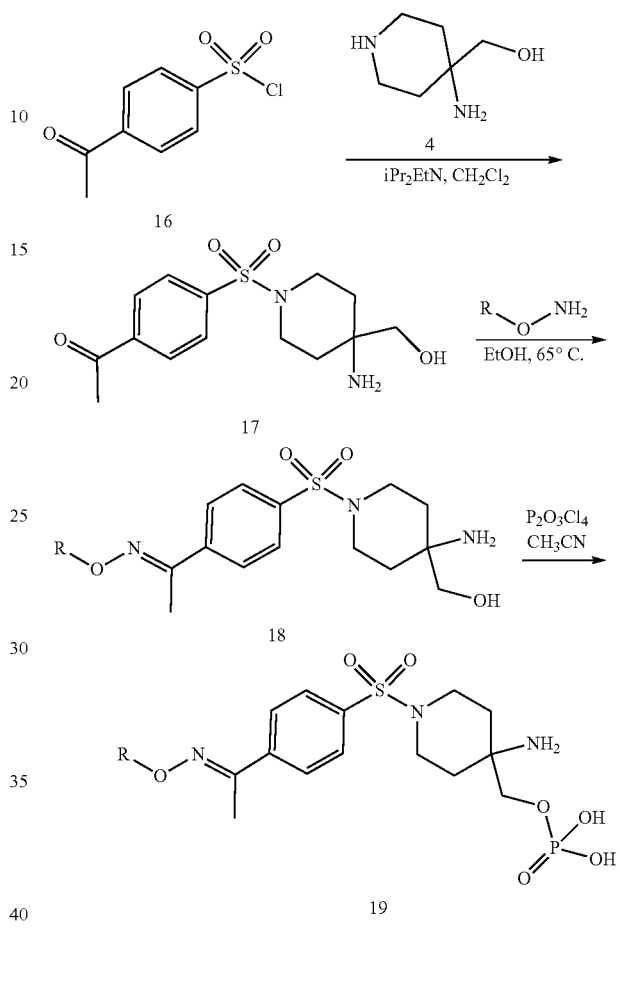

Scheme 5 illustrates one method for the formation of sulfonamides of Formula (I) through the reaction of 4-acetylbenzenesulfonyl chloride with substituted piperi-

EXAMPLES

| ABBREVIATIONS | |
|---|---|
| Ac | acetyl |
| ACN | acetonitrile |
| AcOH | acetic acid |
| anhyd. | anhydrous |
| aq. | aqueous |
| Bu | butyl |
| Boc | tert-butoxycarbonyl |
| CV | Column Volumes |
| DCM | dichloromethane |
| DMAP | dimethylaminopyridine |
| DEA | diethylamine |
| DIPEA | diisopropylethylamine |
| DMF | dimethylformamide |
| DMSO | dimethylsulfoxide |
| EtOAc | ethyl acetate |
| Et | ethyl |
| EtOH | ethanol |
| $H_2$ | hydrogen |
| h, hr or hrs | hour(s) |
| HCl | hydrochloric acid |
| hex | hexane |
| HPLC | high pressure liquid chromatography |

ABBREVIATIONS

| | |
|---|---|
| i | iso |
| LC | liquid chromatography |
| M | molar |
| mM | millimolar |
| Me | methyl |
| MeOH | methanol |
| MHz | megahertz |
| min. | minute(s) |
| mins | minute(s) |
| $M^{+1}$ | $(M + H)^+$ |
| MS | mass spectrometry |
| n or N | normal |
| nm | nanometer |
| nM | nanomolar |
| Pd/C | palladium on carbon |
| Ph | phenyl |
| $PPh_3$ | triphenylphosphine |
| Pr | propyl |
| PSI | pounds per square inch |
| ret. time | retention time |
| sat. | saturated |
| SFC | supercritical fluid chromatography |
| TEA | triethylamine |
| TFA | trifluoroacetic acid |
| THF | tetrahydrofuran |

HPLC Conditions

Condition A: Column: YMC CombiScreen S5 50×4.6 mm (4 min.); Solvent A=10% MeOH-90% $H_2O$-0.2% $H_3PO_3$; Solvent B=90% MeOH-10% $H_2O$-0.2% $H_3PO_4$; Gradient elution from 0% to 100% of Solvent B in Solvent A over 4 min. then 100% of Solvent B for 1 min; Flow Rate=4 mL/min.
Condition G: Column: Waters Acquity BEH C18 2.1×50 mm 1.7 μm; Linear gradient of 0-100% solvent B over 3 min, then 0.75 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Temperature=50° C.; Products detected at 220 nm wavelength.
Condition K: Column: BEH C18 2.1×50 mm 1.7 μm, Linear gradient of 0-100% solvent B over 1.5 min, then 0.7 min hold at 100% B; Flow rate: 1.11 mL/min; Solvent A: 5:95 acetonitrile:water with 10 mM ammonium acetate; Solvent B: 95:5 acetonitrile:water with 10 mM ammonium acetate; Temperature=50° C.; Products detected at 220 nm wavelength.
Condition AA: Column: Luna C18 4.6×30 mm 3 μm; Solvent A: 10:90 $H_2O$:MeOH TFA; Solvent B: 10:90 $H_2O$:MeOH TFA; Gradient: 0%-95% Solvent B in 2 min; 4 mL/min flow.
Condition BB: Column: YMC ProC18 S5 ODS 4.6×50 mm; Start % B=0; Final % B=100; Gradient Time=8 min; Flow Rate=2.5 ml/min; Detection Wavelength=220 nm; Solvent Pair=MeOH/$H_2O$/TFA. Solvent A=10% MeOH-90% $H_2O$-0.2% $H_3PO_4$; Solvent B=90% MeOH-10% $H_2O$-0.2% $H_3PO_4$. Oven Temp.=40° C.
Condition CC: Column=Waters Sunfire C18 2.1×50 mm 5 μm (4 min. grad) Start % B=0; Final % B=100; Gradient Time=4 min; Flow Rate=1 ml/min; Wavelength=220 nm; Solvent Pair=MeOH-$H_2O$-TFA; Solvent A=10% MeOH-90% $H_2O$-0.1% TFA; Solvent B=90% MeOH-10% $H_2O$-0.1% TFA.
Condition DD: Column: YMC CombiScreen S5 50×4.6 mm (4 min) Start % B=0; Final % B=100; Gradient Time=4 min; Flow Rate=4 ml/min; Detection wavelength=254 nm; Solvent A=10% MeOH-90% $H_2O$-0.2% $H_3PO_4$; Solvent B=90% MeOH-10% $H_2O$-0.2% $H_3PO_4$.
Condition EE: Column: Waters Acquity BEH C18 1.7 μm 2.0×50 mm Start % B=0; Final % B=100; Gradient Time=1.5 Minutes; Flow Rate=1 ml/min; Detection wavelength=220 nm; Solvent Pair=Water:ACN:TFA; Solvent A=90:10 Water:ACN with 0.1% TFA; Solvent B=10:90 Water:ACN with 0.1% TFA.
Condition KK: Column: BEH C18 2.1×50 mm 1.7 μm, Linear gradient of 0-100% solvent B over 1.0 min, then 0.5 min hold at 98% B; 1.5-1.6 min 98% B-2% B, Flow rate: 0.8 mL/min; Run time 2.2 min. Solvent A: 5:95 acetonitrile:water with 10 mM ammonium acetate; Solvent B: 95:5 acetonitrile:water with 10 mM ammonium acetate; Temperature=50° C.; Products detected at 220 nm wavelength.

Examples 1 to 4

1-(4-(3-amino-3-(hydroxymethyl)cyclopentyl)phenyl)ethanone O-phenethyl Oxime

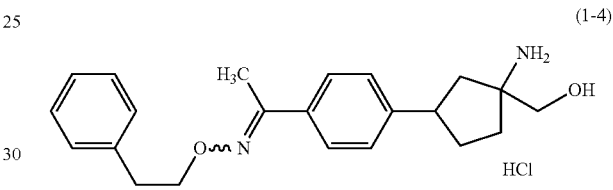

(1-4)

Preparation 1A:
3-(4-bromophenyl)cyclopentan-1-one

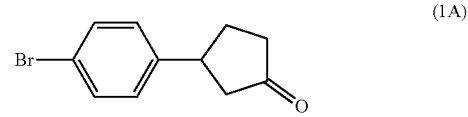

(1A)

To a mixture of 4-bromophenylboronic acid (9.17 g, 45.7 mmol), dioxane (30 mL), and water (5 mL) were sequentially added cyclopent-2-enone (3.06 mL, 36.5 mmol) and chloro(1,5-cyclooctadiene)rhodium(I), dimer (0.216 g, 0.438 mmol) at room temperature under a nitrogen atmosphere. To the orange homogenous reaction mixture was added triethylamine (5.09 mL, 36.5 mmol) over a period of 2 min. at room temperature. The brown-orange reaction mixture was stirred at room temperature for 18 h. The reaction mixture was concentrated and partitioned between EtOAc (150 mL) and brine (60 mL). The EtOAc layer was dried over sodium sulfate and concentrated. To the semi-solid that was obtained was added hexane (50 mL). The contents were triturated for 5 min, sonicated for 10 min. and filtered. The solid was washed with hexane (2×20 mL) and dried to yield 3-(4-bromophenyl)cyclopentanone (5.1 g, 21.33 mmol, 58.4% yield) as a pale yellow solid. The product had an HPLC ret. time=2.82 min (Condition A); LC/MS $M^{+1}$=239, 241. $^1$H NMR (400 MHz, CHLOROFORM-d) δ 7.46 (d, J=8.4 Hz, 2H), 7.13 (d, J=8.4 Hz, 2H), 3.46-3.29 (m, 1H), 2.66 (br dd, J=18.2, 7.4 Hz, 1H), 2.51-2.38 (m, 2H), 2.38-2.24 (m, 2H), 2.04-1.85 (m, 1H).

Preparation 1B: 7-(4-bromophenyl)-1,3-diazaspiro[4.4]nonane-2,4-dione

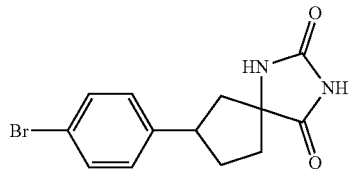
(1B)

To 3-(4-bromophenyl)cyclopentanone (4.8 g, 20.07 mmol) in EtOH (20 mL) and water (10 mL) were sequentially added potassium cyanide (1.961 g, 30.1 mmol) and ammonium carbonate (4.82 g, 50.2 mmol) at room temperature. The reaction vial was sealed, heated at 110° C. (oil bath temp.) for 24 h, cooled using an ice bath, and the cap was slowly unscrewed. Next, 20 mL of water was added to the white solid. The contents were stirred for 10 min. and filtered. The solid was washed with water (5×10 mL) and dried under vacuum for 3 h to yield 7-(4-bromophenyl)-1,3-diazaspiro[4.4]nonane-2,4-dione (6.2 g, 20.05 mmol, 100% yield). HPLC ret. time=2.45 min (Condition AA). LC/MS $M^{+1}$=309, 311. $^1$H NMR (400 MHz, METHANOL-$d_4$) δ 7.44 (d, J=7.5 Hz, 2H), 7.23 (dd, J=8.1, 6.2 Hz, 2H), 2.59-2.33 (m, 1H), 2.30-2.14 (m, 3H), 2.06-1.83 (m, 3H).

Preparation 1C: 1-amino-3-(4-bromophenyl)cyclopentane-1-carboxylic Acid

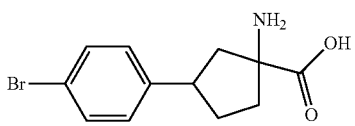
(1C)

To 7-(4-bromophenyl)-1,3-diazaspiro[4.4]nonane-2,4-dione (6.2 g, 20.05 mmol) was added sodium hydroxide (2N aq.) (200 ml, 400 mmol) at room temperature. The mixture was heated at 110° C. (oil bath temp.) for 4 days. The pH was adjusted to 7 by the slow addition of concentrated HCl at room temperature while stirring. As the pH approached close to 7, a white solid separated out. Next, 2 mL of AcOH was added at room temperature. The contents were stirred at room temperature for 5 min. The solid was filtered and washed with water (5×50 mL) (pH of filtrate was 7) and EtOAc (3×50 mL). After drying for 1 h, the sticky solid was washed with THF (3×20 mL) and acetonitrile (3×20 mL) and dried for 3 h. The solid (~6.0 g) was transferred into a 500 mL round bottom flask, azeotroped with MeOH (2×75 mL) and toluene (2×75 mL), and dried under high vacuum. HPLC ret. time=2.11 min (Condition AA) LC/MS $M^{+1}$=284, 286.

Preparation 1D: methyl 1-amino-3-(4-bromophenyl)cyclopentane-1-carboxylate

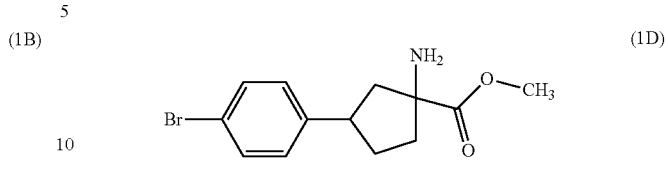
(1D)

Methanol (150 mL) was added to 1-amino-3-(4-bromophenyl) cyclopentanecarboxylic acid (6 g, 21.12 mmol) followed by the addition of thionyl chloride (15.41 mL, 211 mmol) dropwise over a period of 10 min. at room temperature via an additional funnel (exothermic). Towards the end of the addition of thionyl chloride, the reaction mixture became homogenous and slightly cloudy. The mixture was heated at 70° C. (oil bath temp.) for 18 h. The reaction mixture was cooled to room temperature and concentrated under reduced pressure. To the white solid was added EtOAc (25 mL). The contents were triturated and filtered to yield 2.3 g of a white solid. The filtrate was concentrated to yield 2.8 g of a pale yellow solid. LCMS of both solids corresponded to the desired. HPLC ret. time=2.16 min (Condition AA) LC/MS $M^{+1}$=298, 300.

Preparation 1E: (1-amino-3-(4-bromophenyl)cyclopentyl)methanol

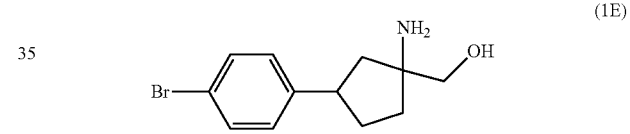
(1E)

To methyl 1-amino-3-(4-bromophenyl)cyclopentanecarboxylate hydrochloride (2.8 g, 8.37 mmol) in EtOH (45 mL) was added sodium borohydride (2 M in triglyme) (29.3 mL, 58.6 mmol) at 0° C. The first 5-8 mL of $NaBH_4$ was added dropwise over a period of 5 min (bubbling of reaction mixture). The remainder of the $NaBH_4$ was added over a period of 5 min. The mixture was stirred at 0° C. for 2 h. The reaction mixture was transferred to a 500 mL beaker and carefully quenched by the slow addition of water (~20 mL) at room temperature. A black-brown solid separated out. Contents of the beaker were decanted into a 1 L round bottom flask. The solid in the beaker was washed with EtOAc (2×20 mL) and the EtOAc washings were transferred into the 1 L round bottom flask. Contents in the 1 L round bottom flask were concentrated under reduced pressure. To the liquid in the round bottom flask was added ether (50 mL). Contents in the flask were triturated and the white solid was filtered off. The filtrate was concentrated to remove ether and an additional 50 mL of ether was added. The contents were triturated and filtered. The filtrate was concentrated to remove ether and the rest of the liquid (mostly triglyme) was distilled using a high vacuum pump. After most of the triglyme was distilled off, the residue in the flask turned into a foamy solid. The contents in the flask were partitioned between EtOAc (2×75 mL) and water (40 mL) (bubbling observed on adding water to foamy solid). The EtOAc layer was dried over sodium sulfate and concentrated under reduced pressure to yield (1-amino-3-(4-bromophenyl)cyclopentyl)methanol (2.3 g, 8.51 mmol, 102% yield) as an oil. The product had an HPLC ret. time=1.73 min. (Condition A). LC/MS M+1=270, 272.

Preparation 1F: 7-(4-bromophenyl)-3-oxa-1-azaspiro[4.4]nonan-2-one

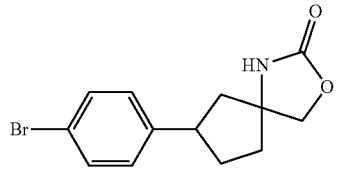

(1F)

To (1-amino-3-(4-bromophenyl)cyclopentyl)methanol (2.3 g, 8.51 mmol) in dichloromethane (20 mL) were sequentially added DIPEA (2.082 mL, 11.92 mmol) and DMAP (0.104 g, 0.851 mmol) at room temperature under a nitrogen atmosphere. To the homogenous solution was added di-tert-butyl dicarbonate (2.77 mL, 11.92 mmol) at room temperature. The reaction mixture was stirred at room temperature for 55 h. The reaction mixture was partitioned between 0.5 N HCl (40 mL) and EtOAc (80 mL). The EtOAc layer was dried over sodium sulfate, concentrated under reduced pressure, and purified by silica gel column chromatography. Fractions corresponding to the desired product were collected and concentrated to yield 7-(4-bromophenyl)-3-oxa-1-azaspiro[4.4]nonan-2-one (1.1 g, 3.71 mmol, 43.6% yield) as a white solid. HPLC ret. time=2.46 min (Condition AA) LC/MS M+1=296, 298. 1H NMR (400 MHz, CHLOROFORM-d) δ 7.52-7.34 (m, 2H), 7.13-7.05 (m, 2H), 4.40-4.22 (m, 2H), 3.27-2.96 (m, 1H), 2.44-2.28 (m, 1H), 2.27-2.09 (m, 2H), 2.05-1.65 (m, 3H).

Preparation 1G: 7-(4-acetylphenyl)-3-oxa-1-azaspiro[4.4]nonan-2-one

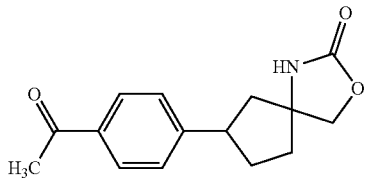

(1G)

A mixture of 7-(4-bromophenyl)-3-oxa-1-azaspiro[4.4] nonan-2-one (0.6 g, 2.026 mmol), dioxane (8 mL), tributyl (1-ethoxyvinyl)stannane (0.719 mL, 2.127 mmol), and bis (triphenylphosphine)palladium(II) chloride (0.071 g, 0.101 mmol) was evacuated and back filled with nitrogen (2×) and heated at 100° C. (oil bath temp.) for 45 min. The reaction mixture was cooled to room temperature and 4 mL of 1N HCl was added. The contents were stirred at room temperature for 18 h. The reaction mixture was concentrated. DCM (20 mL) was added and the contents were stirred at room temperature for 10 min. The DCM layer was filtered over celite and the celite pad was washed with additional DCM (2×20 mL). The DCM layer was concentrated under reduced pressure and purified by silica gel column chromatography to yield 7-(4-acetylphenyl)-3-oxa-1-azaspiro[4.4]nonan-2-one (0.354 g, 1.365 mmol, 67.4% yield) as an oil. HPLC retention time: 2.04 min (Condition AA) LC/MS (M+H): 260.2.

Preparation 1H: 2-phenethoxyisoindoline-1,3-dione

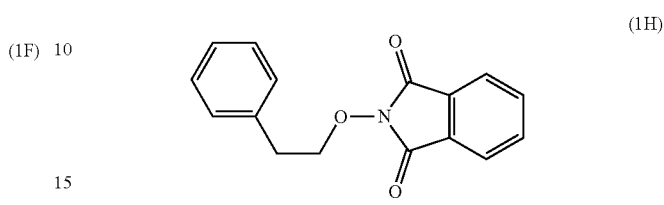

(1H)

To a stirred mixture of 2-phenylethanol (1.961 mL, 16.37 mmol), triphenylphosphine (5.15 g, 19.65 mmol), 2-hydroxyisoindoline-1,3-dione (2.80 g, 17.19 mmol), and THF (20 mL) was added diethyl azodicarboxylate (40% in toluene) (8.95 mL, 19.65 mmol) dropwise over a period of 20 min at 0° C. The orange-yellow reaction mixture was allowed to come to room temperature over a period of 30 min. and stirred at room temperature for 18 h. The reaction mixture was concentrated under reduced pressure. To the semi-solid was added EtOAc (75 mL). The contents were filtered. The solid was washed with additional EtOAc (2×10 mL). The filtrate was concentrated under reduced pressure. The residue was dissolved in DCM and chromatographed to yield 2-phenethoxyisoindoline-1,3-dione (2.4 g, 5.66 mmol, 34.6% yield) (63% purity, 20% of the impurity was PPh3O) as a clear oil. HPLC retention time: 0.95 min (Condition G) LC/MS (M+H): 268.1.

Preparation 1I: O-phenethylhydroxylamine

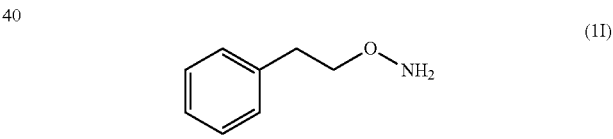

(1I)

To a stirred solution of 2-phenethoxyisoindoline-1,3-dione (63% pure) (2.4 g, 8.98 mmol) in ethanol (20 mL) was added hydrazine (1.409 mL, 44.9 mmol) at room temperature over a period of 2 min. The contents were heated at 90° C. (oil bath temp.) for 1 h. The reaction mixture was cooled to room temperature. EtOH (20 mL) was added. The contents were sonicated for 10 min and filtered over a coarse sintered funnel. The filter cake was washed with additional ethanol (2×20 mL). The filtrate was concentrated under reduced pressure. To the solid was added 1N HCl (20 mL). The contents were sonicated for 5 min. and filtered. The filtrate was extracted with EtOAc (15 mL). The aqueous layer was separated, made basic using 50% aqueous NaOH, and extracted into EtOAc (2×50 mL). The EtOAc layer was dried over sodium sulfate and concentrated under reduced pressure to yield O-phenethylhydroxylamine (0.620 g, 4.52 mmol, 50.3% yield) as a clear oil. HPLC retention time: 0.52 min (Condition A); LC/MS (M+H): 138.15; 1H NMR (400 MHz, CHLOROFORM-d) δ 7.33-7.26 (m, 2H), 7.25-7.17 (m, 3H), 5.38 (br. s., 2H), 3.88 (t, J=7.0 Hz, 2H), 2.90 (t, J=6.9 Hz, 2H).

Preparation 1J: 7-(4-(1-(phenethoxyimino)ethyl)phenyl)-3-oxa-1-azaspiro[4.4]nonan-2-one

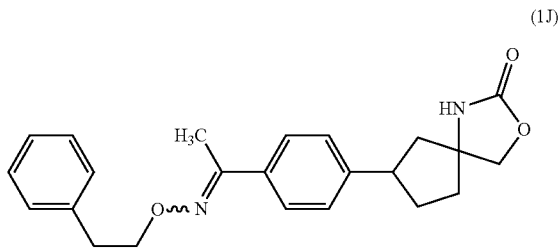 [SMILES: CC(=NOCCc1ccccc1)c1ccc(C2CCC3(COC(=O)N3)C2)cc1]

(1J)

To 7-(4-acetylphenyl)-3-oxa-1-azaspiro[4.4]nonan-2-one (0.12 g, 0.463 mmol) in MeOH (2 mL) was added O-phenethylhydroxylamine (0.063 g, 0.463 mmol), followed by acetic acid (7.95 μl, 0.139 mmol) at room temperature. The reaction mixture was stirred at room temperature for 18 h. LCMS indicated a major and minor peak with desired mass. The reaction mixture was concentrated and subjected to silica gel column chromatography to yield 7-(4-(1-(phenethoxyimino)ethyl)phenyl)-3-oxa-1-azaspiro[4.4]nonan-2-one (0.17 g, 0.449 mmol, 97% yield) as an oil. LC/MS (M+H): 379.2.

Preparation 1K: 1-(4-(3-amino-3-(hydroxymethyl)cyclopentyl)phenyl)ethanone O-phenethyl Oxime

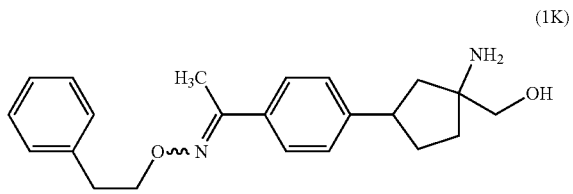 [SMILES: CC(=NOCCc1ccccc1)c1ccc(C2CCC(N)(CO)C2)cc1]

(1K)

To 7-(4-(1-(phenethoxyimino)ethyl)phenyl)-3-oxa-1-azaspiro[4.4]nonan-2-one (0.17 g, 0.449 mmol) in dioxane (8 mL) and water (3.00 mL) was added lithium hydroxide monohydrate (0.140 g, 5.84 mmol) at room temperature. The reaction mixture was heated at 110° C. overnight. LCMS indicated clean conversion to desired product and no starting material. There was a major peak with M+ corresponding to trans isomer and a minor peak with M+ corresponding to the cis isomer. The reaction mixture was concentrated and partitioned between EtOAc (60 mL) and water (15 mL). The aqueous layer was re-extracted with DCM (20 mL). The organic layers were combined, dried over sodium sulfate, and concentrated to yield 1-(4-(3-amino-3-(hydroxymethyl) cyclopentyl)phenyl)ethanone O-phenethyl oxime (0.155 g, 0.396 mmol, 88% yield) as a white solid.

Examples 1-4

Chiral separation of the mixture of stereoisomers of 1-(4-(3-amino-3-(hydroxymethyl)cyclopentyl)phenyl)ethanone O-phenethyl oxime was completed in two stages. The first chiral separation (Column: Chiralpak AD-H 25×3 cm, 5 m; Column Temp.: 35° C.; Flow rate: 150 mL/min; Mobile Phase: $CO_2$/(MeOH+0.5% DEA)=70/30; Detector Wavelength: 233 nm) afforded two fractions (F1 and F2).

Chiral separation of F1 (Column: Chiralpak AS-H 25×3 cm, 5 m; Column Temp.: 35° C.; Flow rate: 150 mL/min; Mobile Phase: $CO_2$/[MEOH-$CH_3CN$(1:1)+0.5% DEA]=70/25; Detector Wavelength: 260 nm) afforded two fractions (F1A and F1B).

Chiral separation of F2 (Column: Chiralpak AS-H 25×3 cm, 5 m; Column Temp.: 35° C.; Flow rate: 150 mL/min; Mobile Phase: $CO_2$/[MEOH-$CH_3CN$(1:1)+0.5% DEA]=85/15; Detector Wavelength: 260 nm) afforded two fractions (F2A and F2B).

F1A: Example 1: LC/MS (M+H): 353.4; HPLC retention time: 3.001 min (Condition A); $^1$H NMR (400 MHz, CHLOROFORM-d) δ 7.60-7.55 (m, 2H), 7.33-7.19 (m, 7H), 4.39 (t, J=7.0 Hz, 2H), 3.47 (s, 2H), 3.45-3.35 (m, 1H), 3.05 (t, J=7.0 Hz, 2H), 2.28-2.21 (m, 1H), 2.19 (s, 3H), 2.04-1.96 (m, 1H), 1.91 (dd, J=13.0, 7.0 Hz, 1H), 1.76-1.64 (m, 2H), 1.59-1.49 (m, 1H).

F1B: Example 2: LC/MS (M+H): 353.4; LC retention time: 3.020 min (Condition A); $^1$H NMR (400 MHz, CHLOROFORM-d) δ 7.60-7.55 (m, 2H), 7.34-7.18 (m, 7H), 4.39 (t, J=7.0 Hz, 2H), 3.52-3.42 (m, 2H), 3.16-3.07 (m, 1H), 3.04 (t, J=7.0 Hz, 2H), 2.30 (dd, J=13.3, 7.8 Hz, 1H), 2.19 (s, 3H), 2.14-2.04 (m, 1H), 1.98-1.87 (m, 1H), 1.82-1.66 (m, 2H), 1.52 (dd, J=13.1, 10.9 Hz, 1H).

F2A: Example 3: LC/MS (M+H): 353.4; LC retention time: 3.013 min (Condition A); $^1$H NMR (400 MHz, CHLOROFORM-d) δ 7.60-7.55 (m, 2H), 7.33-7.18 (m, 7H), 4.39 (t, J=7.0 Hz, 2H), 3.47 (s, 2H), 3.44-3.34 (m, 1H), 3.04 (t, J=7.0 Hz, 2H), 2.27-2.20 (m, 1H), 2.19 (s, 3H), 2.04-1.95 (m, 1H), 1.91 (dd, J=13.0, 7.3 Hz, 1H), 1.76-1.64 (m, 2H), 1.59-1.50 (m, 1H).

F2B: Example 4: LC/MS (M+H): 353.5; LC retention time: 3.020 min (Condition A); $^1$H NMR (400 MHz, CHLOROFORM-d) δ 7.61-7.55 (m, 2H), 7.33-7.18 (m, 7H), 4.39 (t, J=6.9 Hz, 2H), 3.51-3.41 (m, 2H), 3.17-3.07 (m, 1H), 3.05 (t, J=7.0 Hz, 2H), 2.33-2.26 (m, 1H), 2.19 (s, 3H), 2.15-2.04 (m, 1H), 2.00-1.86 (m, 1H), 1.82-1.72 (m, 1H), 1.71-1.63 (m, 1H), 1.54-1.46 (m, 1H).

Intermediate A1: 1-(4-((1R,3R)-3-amino-3-(hydroxymethyl)cyclopentyl)phenyl) ethanone Hydrochloride

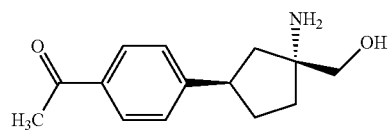

(I-A1)

To ((1R,3R)-1-amino-3-(4-bromophenyl)cyclopentyl) methanol (0.65 g, 2.406 mmol) in dioxane (3 mL) were added tributyl(1-ethoxyvinyl)stannane (0.975 mL, 2.89 mmol) followed by bis(triphenylphosphine)palladium(II) chloride (0.135 g, 0.192 mmol) at room temperature. The flask was evacuated and back flushed with nitrogen (2×) and heated at 110° C. for 6 h. The reaction mixture was cooled to room temperature, filtered and the filter cake washed with dioxane (2×2 mL). To the filtrate was added 0.5 mL of 4N HCl in dioxane dropwise over 1 min. at room temperature and the homogenous reaction mixture is stirred at room temperature for 15 min. The reaction mixture was concentrated under reduced pressure. To the semi-solid that was obtained was added acetonitrile (10 mL). The contents were sonicated for 30 min., filtered and washed with acetonitrile (2×3 mL) and dried under vacuum to yield 1-(4-((1R,3R)-3-amino-3-(hydroxymethyl)cyclopentyl)phenyl)ethanone hydrochloride (310 mg, 0.977 mmol, 40.6% yield) as yellow solid. HPLC ret. time=1.275/5.0 min (condition K); LC/MS M+1=234.2.

Intermediate A-2: (1R,3S)-3-(4-acetylphenyl)-1-(hydroxymethyl)cyclopentan-1-aminium Chloride

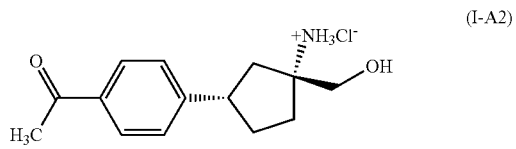

(I-A2)

To a solution of (1R,3S)-methyl 1-amino-3-(4-bromophenyl) cyclopentanecarboxylate (2 g, 6.71 mmol) in EtOH (50 mL) was slowly added sodium borohydride (0.761 g, 20.12 mmol). The reaction mixture was stirred at room temperature for 0.5 h and then stirred at 55° C. for 4 h. The reaction mixture was cooled to 0° C. and 12 N aqueous HCl (10 mL) was added dropwise to quench the reaction. The suspension was stirred at room temperature for 30 min before aqueous NaOH (4 g of NaOH in 10 mL of water) was added at 0° C. The mixture was stirred at room temperature for 1 h and then concentrated on the rotavapor. Ethyl acetate (50 mL) was added. The aqueous layer was separated and extracted with ethyl acetate (3×50 mL). The combined ethyl acetate solutions were dried over Na$_2$SO$_4$ and then concentrated under reduced pressure to give ((1R,3S)-1-amino-3-(4-bromophenyl)cyclopentyl) methanol as a white solid. HPLC ret. time=2.12 min (Condition CC); ESI-MS: m/z 271.17 (M+H).

To ((1R,3S)-1-amino-3-(4-bromophenyl)cyclopentyl) methanol (0.36 g, 1.333 mmol) in dioxane (5 mL) was added tributyl(1-ethoxyvinyl)stannane (0.495 mL, 1.466 mmol) followed by the addition of bis(triphenylphosphine)palladium(II) chloride (0.047 g, 0.067 mmol) at room temperature. The reaction vessel was evacuated, back flushed with nitrogen and heated at 110° C. for 1 h. The reaction mixture was cooled to room temperature and filtered. The filter cake was washed with dioxane (2×3 mL). To the filtrate was added 0.6 mL of 4 N HCl in dioxane dropwise over 1 min. at room temperature. The homogenous reaction mixture was stirred at room temperature for 15 min. The reaction mixture was concentrated under reduced pressure. To the semi-solid was added acetonitrile (10 mL). The contents were sonicated for 30 min., filtered and washed with acetonitrile (2×3 mL) and dried over Na$_2$SO$_4$ to yield 1-(4-((1S,3R)-3-amino-3-(hydroxymethyl)cyclopentyl) phenyl)ethanone hydrochloride (0.245 g, 0.799 mmol, 60.0% yield) as a pale yellow solid. HPLC ret. time=1.26 min (Condition DD); ESI-MS: m/z 234.2 (M+H).

Example 5

1-(4-((1R,3R)-3-amino-3-(hydroxymethyl)cyclopentyl)phenyl)ethanone O-benzyl oxime, TFA

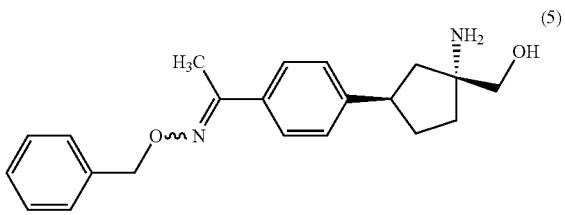 [SMILES: CC(=NOCc1ccccc1)c1ccc([C@@H]2CC[C@](N)(CO)C2)cc1]

(5)

To 1-(4-((1R,3R)-3-amino-3-(hydroxymethyl)cyclopentyl)phenyl)ethanone, HCl (25 mg, 0.072 mmol) in ethanol (1 mL) were sequentially added O-benzylhydroxylamine (17.73 mg, 0.144 mmol) and pyridine (0.017 mL, 0.216 mmol) at room temperature. The reaction mixture was heated at 70° C. (oil bath temp.) for 1 h. LCMS analysis indicated completion of the reaction. The crude material was purified on reverse phase HPLC. The product containing fractions were collected and dried under high vacuum overnight to provide 1-(4-((1R,3R)-3-amino-3-(hydroxymethyl)cyclopentyl)phenyl)ethanone O-benzyl oxime, TFA (18 mg, 0.038 mmol, 53.1% yield). HPLC ret. time: 0.79/2.0 min (condition G), LC/MS M+$^{+1}$=339.2. $^1$H NMR (400 MHz, METHANOL-d$_4$) δ 7.64 (d, J=8.1 Hz, 2H), 7.49-7.25 (m, 7H), 5.22 (s, 2H), 3.66 (m, 2H), 2.27 (s, 3H), 2.35-2.18 (m, 3H), 2.07 (s, 1H), 1.97-1.71 (m, 3H).

The Examples in Table 1 were prepared according to the general procedure for Example 5 using either Intermediate A-1 or I A-2.

TABLE 1

| Ex. No. | Structure | MW | HPLC ret. time (min.) | HPLC condition | MS (M$^{+1}$) |
|---|---|---|---|---|---|
| 3 | ![structure] | 352.47 | 0.81 | G | 353.2 |
| 6 | ![structure] | 302.4 | 0.74 | G | 303.2 |

TABLE 1-continued

| Ex. No. | Structure | MW | HPLC ret. time (min.) | HPLC condition | MS (M⁺¹) |
|---|---|---|---|---|---|
| 7 | 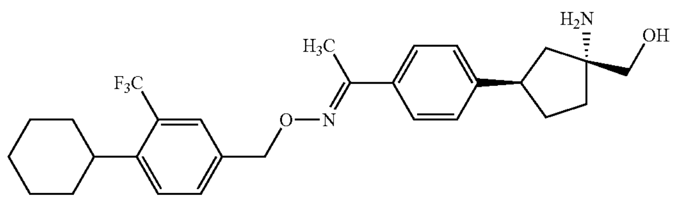 [SMILES: C/C(=N\OCc1ccc(C2CCCCC2)c(C(F)(F)F)c1)c1ccc([C@@H]2CC[C@](N)(CO)C2)cc1] | 488.58 | 0.98 | G | 489.3 |
| 8 | 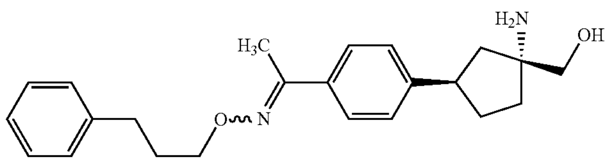 [SMILES: CC(=NOCCCc1ccccc1)c1ccc([C@@H]2CC[C@](N)(CO)C2)cc1] | 366.49 | 0.89 | G | 367.2 |
| 9 | 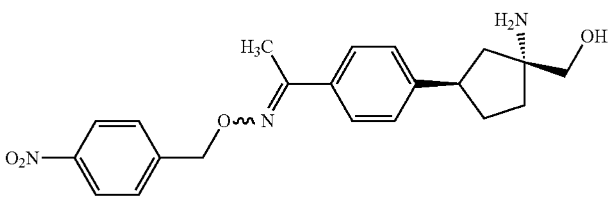 [SMILES: CC(=NOCc1ccc([N+](=O)[O-])cc1)c1ccc([C@@H]2CC[C@](N)(CO)C2)cc1] | 383.44 | 0.80 | G | 384.3 |
| 10 | 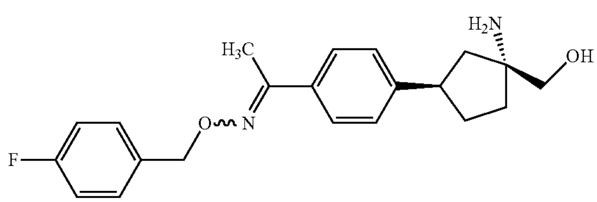 [SMILES: CC(=NOCc1ccc(F)cc1)c1ccc([C@@H]2CC[C@](N)(CO)C2)cc1] | 356.43 | 0.82 | G | 357.3 |
| 11 | 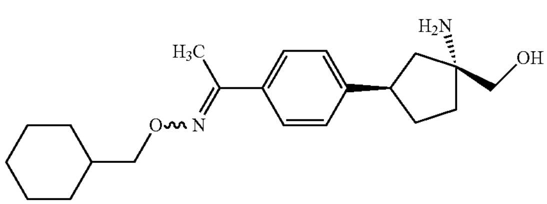 [SMILES: CC(=NOCC1CCCCC1)c1ccc([C@@H]2CC[C@](N)(CO)C2)cc1] | 344.49 | 0.93 | G | 345.3 |
| 12 | 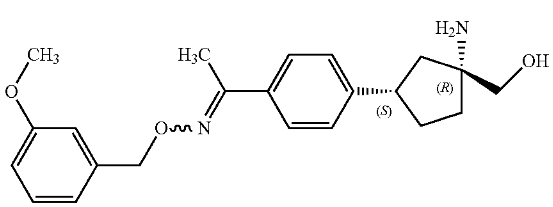 | 368.21 | 3.03 | CC | 369.2 |

TABLE 1-continued

| Ex. No. | Structure | MW | HPLC ret. time (min.) | HPLC condition | MS (M+1) |
|---|---|---|---|---|---|
| 13 | 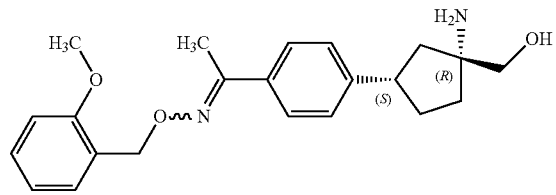 | 368.21 | 3.06 | CC | 369.2 |
| 14 | 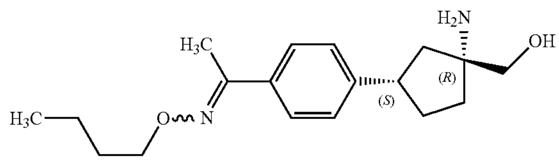 | 304.22 | 3.14 | CC | 305.2 |

Intermediate B-1: Methyl 4-((1R,3R)-3-amino-3-(methoxycarbonyl) cyclopentyl) Benzoate (I-B1)

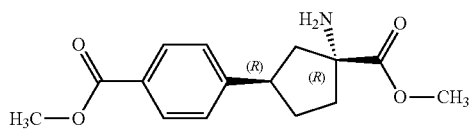

(1R,3R)-methyl 1-amino-3-(4-iodophenyl)cyclopentanecarboxylate (400 mg, 1.159 mmol), palladium (II) acetate (78 mg, 0.348 mmol) and 1,3-bis(diphenylphosphino)propane (143 mg, 0.348 mmol) were suspended in MeOH (5 mL). To this mixture was added TEA (0.646 mL, 4.64 mmol). The reaction was conducted in a steel bomb at 20 psi CO. The mixture was allowed to stir at 80° C. for 15 hours. The catalyst was filtered off and the TEA was removed under vacuum. The residues were redissolved into 1.5 ml MeOH and treated with 2 ml of 4 N HCl. The mixtures were allowed to stir at room temperature overnight. The MeOH was evaporated, and the residue was partitioned between 15 ml 1N HCl and 12 ml of ethyl acetate. The aqueous layer was separated and basified with 40% NaOH to pH 10 and extracted with ethyl acetate three times. LCMS indicated no product remaining in the aqueous layer. The ethyl acetate layers were combined and concentrated to provide 4-((1R,3R)-3-amino-3-(methoxycarbonyl)cyclopentyl)benzoate (220 mg, 0.79 mmol, 68% yield) as yellow oil. HPLC ret. time=0.62 min (condition G); LC/MS M+=278.1.

Intermediate C-1: ((1R,3R)-1-amino-3-(4-(hydroxymethyl)phenyl)cyclopentyl)methanol (I-C1)

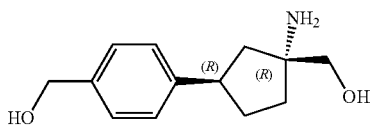

Methyl 4-((1R,3R)-3-amino-3-(methoxycarbonyl)cyclopentyl)benzoate (220 mg, 0.793 mmol) was dissolved in dry THF (4 mL). The solution was cooled down to 0° C. before adding LAH (1.745 mL, 1.745 mmol) slowly. The mixtures were allowed to stir at 0° C. for 1 hour. LCMS analysis indicated that the reaction was complete. The reaction mixture was diluted with 40 ml ether, then $H_2O$ (0.15 ml) was added, followed by 15% NaOH (0.15 mL) and additional $H_2O$ (1.2 mL). The mixture was allowed to stir at room temperature for 45 mins. The sticky solid was filtered off and was washed three times with ethyl acetate. The organic layers were combined and dried over $Na_2SO_4$ and concentrated to provide of ((1R,3R)-1-amino-3-(4-(hydroxymethyl)phenyl)cyclopentyl) methanol (140 mg, 0.633 mmol, 80% yield) as pale yellow oil. HPLC ret time=0.45 min (condition G); LC/MS $M^{+1}$=222.1.

Intermediate D-1: (5R,7R)-7-(4-(hydroxymethyl)phenyl)-3-oxa-1-azaspiro[4.4]nonan-2-one (I-D1)

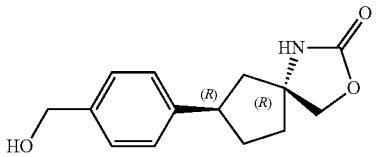

((1R,3R)-1-amino-3-(4-(hydroxymethyl)phenyl)cyclopentyl)methanol (120 mg, 0.542 mmol) was mixed with sodium hydroxide (0.387 ml, 2.169 mmol) and $CHCl_3$ (3 ml). Phosgene (20% in toluene) (0.428 ml, 0.813 mmol) was added into this mixture at room temperature. The mixture was allowed to stir at 45° C. for 2 hours. The solution was cooled down to room temperature, the pH was adjusted to 7-8 and the solution was extracted with ethyl acetate. The organics were evaporated and first purified on silica gel column, which gave incomplete purification. The material was repurified on reverse phase HPLC to provide (5R,7R)-7-(4-(hydroxymethyl)phenyl)-3-oxa-1-azaspiro[4.4]nonan-2-one (45 mg, 34% yield) as a white solid. HPLC ret. time=0.61 min (condition G); LC/MS $M^{+1}$=248.1. $^1$H NMR (400 MHz, METHANOL-$d_4$) δ 7.35-7.30 (m, 2H), 7.29-

7.24 (m, 2H), 4.60 (s, 2H), 4.43-4.34 (m, 2H), 3.32 (m, 1H), 2.32 (dd, J=13.4, 7.3 Hz, 1H), 2.25-2.16 (m, 2H), 2.02 (s, 1H), 1.92 (dd, J=13.4, 11.4 Hz, 1H), 1.75 (br. s., 1H).

Intermediate E-1: 2-((4-((5R,7R)-2-oxo-3-oxa-1-azaspiro[4.4]nonan-7-yl)benzyl)oxy) isoindoline-1,3-dione

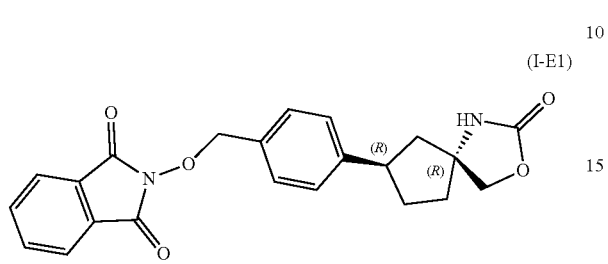

(I-E1)

To (5R,7R)-7-(4-(hydroxymethyl)phenyl)-3-oxa-1-azaspiro[4.4]nonan-2-one (45 mg, 0.182 mmol) in THF (4 mL) were sequentially added triphenylphosphine (62.0 mg, 0.237 mmol) and 2-hydroxyisoindoline-1,3-dione (31.2 mg, 0.191 mmol) at room temperature. The reaction mixture was cooled to 0° C. and DEAD (0.037 mL, 0.237 mmol) in THF (0.6 mL) was added dropwise over a period of 1-2 min. The slightly heterogeneous reaction mixture became homogenous as the addition of DEAD proceeded. The orange-yellow reaction mixture was allowed to warm to room temperature over a period of 30 min. and stirred at room temperature for 15 h. LCMS analysis indicated >90% conversion of starting material. The reaction mixture was concentrated under reduced pressure and the residue was purified on silica gel column. 12 g column 0-60% gradient Sol B in 15 mins, hold for 15 mins. Sol A: Hexane; Sol B: ethyl acetate. The product containing fractions were collected and evaporated under vacuum to provide 2-((4-((5R,7R)-2-oxo-3-oxa-1-azaspiro[4.4]nonan-7-yl)benzyl)oxy)isoindoline-1,3-dione (38 mg, 53% yield) as a white solid. HPLC ret. time=0.83 min (condition G); LC/MS M+1=393.1.

Intermediate F-1: (5R,7R)-7-(4-((aminooxy)methyl)phenyl)-3-oxa-1-azaspiro[4.4]nonan-2-one

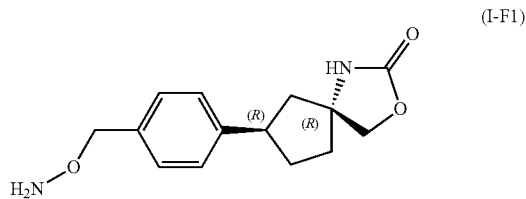

(I-F1)

To 2-((4-((5R,7R)-2-oxo-3-oxa-1-azaspiro[4.4]nonan-7-yl)benzyl)oxy) isoindoline-1,3-dione (38 mg, 0.097 mmol) in ethanol (2 mL) was added hydrazine (0.015 mL, 0.484 mmol) over a period of 1-2 min. at room temperature. After stirring for 5 minutes at room temperature, the solution became cloudy with a white precipitate. The contents were heated at 80° C. (oil bath temp.) for 1 h (additional white solid separated out). LCMS analysis indicated formation of desired product. The reaction mixture was cooled to room temperature, EtOH (2 mL) was added, and the mixture was sonicated and filtered. The solids were washed with additional ethanol (2×1 mL). The solvents were evaporated and 3 ml of saturated NaHCO₃ was added and the solution was extracted with ethyl acetate three times. The organic layers were combined and concentrated to provide (5R,7R)-7-(4-((aminooxy)methyl)phenyl)-3-oxa-1-azaspiro[4.4] nonan-2-one (26 mg). HPLC ret. time=0.51 min (condition G); LC/MS M+1=263.0.

Intermediate G: (5R,7R)-7-(4-((((E)-(1-phenylethylidene)amino)oxy)methyl)phenyl)-3-oxa-1-azaspiro[4.4]nonan-2-one

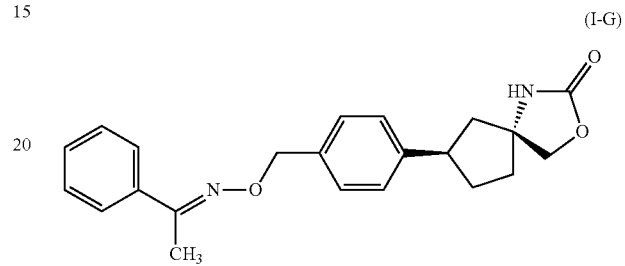

(I-G)

To (5R,7R)-7-(4-((aminooxy)methyl)phenyl)-3-oxa-1-azaspiro[4.4]nonan-2-one (25 mg, 0.095 mmol) in ethanol (1.5 mL) were sequentially added acetophenone (13.74 mg, 0.114 mmol) and pyridine (0.023 mL, 0.286 mmol) at room temperature. The reaction mixture was heated at 70° C. (oil bath temp.) for 1 h. LCMS indicated only trace amount of product. The reaction mixture was allowed to stir at 80° C. for 4 days. LCMS analysis indicated >90% conversion. The reaction mixture was purified on reverse phase HPLC. Column: Phen Luna-Axia C18 21.2*100 mm Sol A: 10% MeOH-90% H₂O-0.1% TFA; Sol B: 90% MeOH-10% H₂O-0.5% TFA. The fractions were collected to provide (5R,7R)-7-(4-((((E)-(1-phenylethylidene)amino)oxy)methyl)phenyl)-3-oxa-1azaspiro[4.4]nonan-2-one (14 mg, 41% yield) as a white solid. HPLC ret. time=1.01 min (condition G); LC/MS M⁺¹=365.3.

Intermediate H: tert-butyl ((1R,3R)-1-(hydroxymethyl)-3-(4-((((E)-(1 phenylethylidene) amino)oxy) methyl)phenyl)cyclopentyl)carbamate

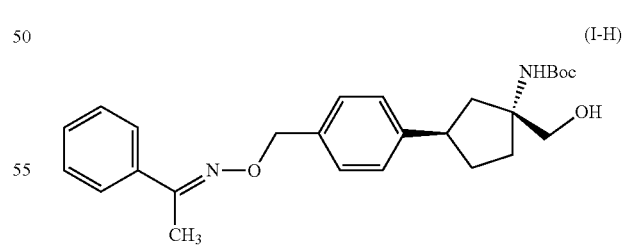

(I-H)

(5R,7R)-7-(4-((((E)-(1-phenylethylidene)amino)oxy) methyl)phenyl)-3-oxa-1-azaspiro[4.4]nonan-2-one (10 mg, 0.027 mmol) was dissolved into CH₂Cl₂ (2 mL), and BOC₂O (0.013 mL, 0.055 mmol), Et₃N (8.33 mg, 0.082 mmol) and a catalytic amount of DMAP were added at room temperature. The mixture was allowed to stir at room temperature for 24 hours. LCMS analysis indicated >90% conversion. The solvent was removed under vacuum and the resulting residue was redissolved into MeOH (2 mL) with 2 drops of H$_2$O. K$_2$CO$_3$ (25 mg, 0.181 mmol) was then added and the mixture was allowed to stir at room temperature overnight. LCMS analysis showed the reaction to be complete. The K$_2$CO$_3$ was filtered off and the MeOH was evaporated. The residue was redissolved into 40 ml ethyl acetate and washed with saturated aqueous NaCl. The organic layer was then dried over Na$_2$SO$_4$ and concentrated under high vacuum to provide tert-butyl ((1R,3R)-1-(hydroxymethyl)-3-(4-((((E)-(1-phenylethylidene)amino)oxy) methyl)phenyl)cyclopentyl)carbamate (13 mg). HPLC ret. time=1.14 min (condition G); LC/MS M+1=439.3.

Example 15

(E)-acetophenone O-(4-((1R,3R)-3-amino-3-(hydroxymethyl)cyclopentyl)benzyl) oxime, TFA

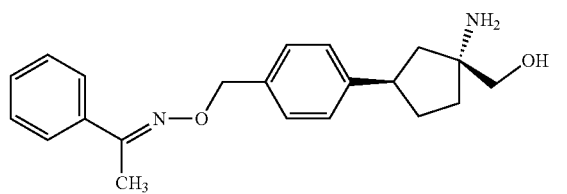

(15)

A solution of tert-butyl ((1R,3R)-1-(hydroxymethyl)-3-(4-((((E)-(1-phenylethylidene)amino)oxy)methyl)phenyl) cyclopentyl)carbamate (13 mg, 0.030 mmol) in CH$_2$Cl$_2$ (3 mL) was cooled down to 0° C. and TFA (1 ml, 12.98 mmol) was added. The reaction mixture was allowed to stir at 0° C. for 2 hours and the solvent was evaporated. The residue was purified on reverse phase HPLC. Column: Phen Luna-Axia C18 21.2*100 mm Sol A: 10% MeOH-90% H$_2$O-0.1% TFA; Sol B: 90% MeOH-10% H$_2$O-0.5% TFA. The product containing fractions were combined and dried under vacuum overnight to provide (E)-acetophenone O-(4-((1R,3R)-3-amino-3-(hydroxymethyl)cyclopentyl)benzyl)oxime, TFA (4.85 mg, 36% yield). HPLC ret. time=0.81 min (condition G); LC/MS M+$^1$=339.2. $^1$H NMR (400 MHz, METHANOL-d$_4$) δ 7.72-7.63 (m, 2H), 7.48-7.38 (m, 5H), 7.34-7.27 (m, 2H), 5.21 (s, 2H), 3.67 (d, J=7.0 Hz, 2H), 3.38 (br. s., 1H), 2.27 (s, 3H), 2.26-2.17 (m, 3H), 1.96-1.76 (m, 3H).

Intermediate I: ((1R,3S)-1-amino-3-(4-bromophenyl)cyclopentyl)methanol

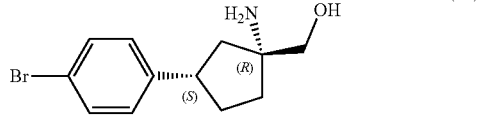

(I-I)

To a mixture of (1R,3S)-methyl 1-amino-3-(4-bromophenyl) cyclopentanecarboxylate, HCl (15 g, 44.8 mmol) in MeOH (100 mL) at 0° C. was added sodium borohydride (4 g, 106 mmol) portionwise. The reaction mixture was warmed to room temperature and sodium borohydride was added portionwise until the reaction was determined to be complete by HPLC analysis. Water was added to quench the reaction. The reaction mixture was diluted with ethyl acetate and washed with saturated NaCl. The aqueous layer was back extracted several times. The combined organic layers were dried with MgSO$_4$, filtered and concentrated. The product (11 g) was recovered after concentration. HPLC retention time=0.65 min (condition G); LC/MS M+$^1$=272: $^1$H NMR (400 MHz, DMSO-d$_6$) δ 7.51-7.40 (m, 2H), 7.27 (d, J=8.4 Hz, 2H), 3.32-3.20 (m, 2H), 3.09-2.92 (m, 1H), 2.11 (dd, J=12.9, 8.7 Hz, 1H), 1.98-1.87 (m, 1H), 1.80 (qd, J=11.1, 7.9 Hz, 1H), 1.69-1.58 (m, 1H), 1.48 (ddd, J=12.4, 7.9, 2.2 Hz, 1H), 1.32 (dd, J=12.8, 10.1 Hz, 1H).

Intermediate J: (5R,7S)-7-(4-bromophenyl)-3-oxa-1-azaspiro[4.4]nonan-2-one

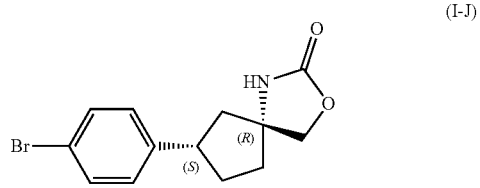

(I-J)

To a mixture of ((1R,3S)-1-amino-3-(4-bromophenyl)cyclopentyl)methanol (11 g, 40.7 mmol) and pyridine (3.29 mL, 40.7 mmol) in dioxane (300 mL) was added 1,1'-carbonyldiimidazole (19.81 g, 122 mmol). The reaction mixture was stirred for 4 hours. The reaction mixture was diluted with ethyl acetate and washed with 1M HCl, brine and saturated NaHCO$_3$. The mixture was back extracted several times. The organic layer was dried with MgSO$_4$, filtered and concentrated to afford 10.5 g of desired product as an off-white solid. HPLC retention time=0.87 min (condition G); LC/MS M+$^1$=297.9; $^1$H NMR (400 MHz, CHLOROFORM-d) δ 7.45 (d, J=8.6 Hz, 2H), 7.12 (d, J=8.4 Hz, 2H), 6.42 (br. s., 1H), 4.41-4.21 (m, 2H), 3.17-2.91 (m, 1H), 2.34 (dd, J=13.3, 7.4 Hz, 1H), 2.23-2.11 (m, 2H), 2.01-1.90 (m, 2H), 1.88-1.74 (m, 1H).

Intermediate K: methyl 4-((5R,7S)-2-oxo-3-oxa-1-azaspiro[4.4]nonan-7-yl)benzoate

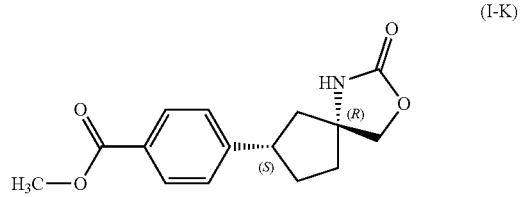

(I-K)

A mixture of (5R,7S)-7-(4-bromophenyl)-3-oxa-1-azaspiro[4.4]nonan-2-one (1 g, 3.38 mmol), 1,3-bis(diphenylphosphino)propane (0.139 g, 0.338 mmol), diacetoxypalladium (0.076 g, 0.338 mmol), TEA (1.412 ml, 10.13 mmol), N,N-dimethylforamide (15 mL) and methanol (5 mL) was stirred at 80° C. for 50 h under a carbon monoxide atmosphere (30 psi). After cooling to room temperature, the mixture was diluted with EtOAc (100 mL) and washed with water (30 mL×2) and brine (30 mL). The organic layer was dried over sodium sulfate and concentrated on the rotavapor. The residue was purified by flash column chromatography Intermediate L: 4-((5R,7S)-2-oxo-3-oxa-1-azaspiro[4.4]nonan-7-yl)benzoic Acid

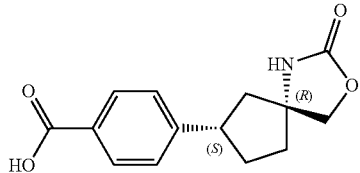

(I-L)

To a mixture of methyl 4-((5R,7S)-2-oxo-3-oxa-1-azaspiro[4.4]nonan-7-yl) benzoate (150 mg, 0.545 mmol) in MeOH (3 mL) was added NaOH (2043 µl, 8.17 mmol). The mixture was stirred at room temperature for 3 h. To the mixture was added 10 mL of water, acidified with concentrated HCl, and extracted with EtOAc (2×30 mL). The organic layer was washed with water (20 mL) and brine (20 mL). The organic layer was dried over sodium sulfate and concentrated on the rotavapor to give the title compound. HPLC ret. time=0.90 min (Condition EE); ESI-MS: m/z 262.4 (M+H+).

Intermediate D2: (5R,7S)-7-(4-(hydroxymethyl)phenyl)-3-oxa-1-azaspiro[4.4]nonan-2-one

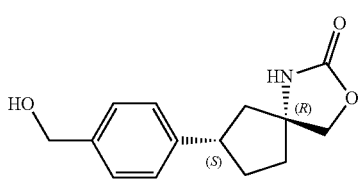

(I-D2)

To a mixture of 4-((5R,7S)-2-oxo-3-oxa-1-azaspiro[4.4]nonan-7-yl)benzoic acid (150 mg, 0.574 mmol) in THF (3 mL) was added BH$_3$.THF (1722 µl, 1.722 mmol) at −5° C. The mixture was warmed up slowly to room temperature and continued to stir for 16 h. To the mixture was added 1 mL of MeOH and diluted with EtOAc (30 mL) and water 10 mL. The aqueous layer was extracted with EtOAc (30 mL) and the combined organic layer was washed with brine (20 mL). The organic layer was dried over sodium sulfate and concentrated on the rotavapor. The crude material was purified with Isco column (12 g, EtOAc/Hexane=0-100%, gradient time=15 min, out at 85% of EtOAc, tube 18-20) to give the title compound. HPLC ret. time=0.92 min (Condition EE); ESI-MS: m/z 248.3 (M+H+).

Intermediate E2: 2-((4-((5R,7S)-2-oxo-3-oxa-1-azaspiro[4.4]nonan-7-yl)benzyl)oxy) isoindoline-1,3-dione

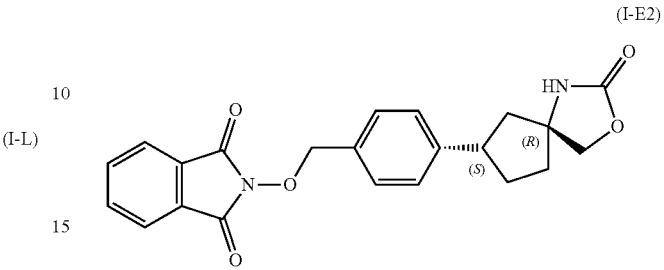

(I-E2)

To (5R,7S)-7-(4-(hydroxymethyl)phenyl)-3-oxa-1-azaspiro[4.4]nonan-2-one (85 mg, 0.344 mmol) in THF (8 mL) were sequentially added triphenylphosphine (135 mg, 0.516 mmol) and 2-hydroxyisoindoline-1,3-dione (67.3 mg, 0.412 mmol) at room temperature. The reaction mixture was cooled to 0° C. and DEAD (82 µl, 0.516 mmol) in THF (1 mL) was added dropwise over a period of 1-2 min. The clear reaction mixture was allowed to come to room temperature over a period of 30 min. and stirred at room temperature for 16 h. The mixture was diluted with EtOAc (30 ml), washed with brine (30 ml), dried over Na$_2$SO$_4$ and concentrated under reduced pressure. The mixture was then purified on silica gel column. 12 g column 0-60% gradient in 15 mins, Sol A: Hexane; Sol B: ethyl acetate. The fractions were collected to afford 100 mg of 2-((4-((5R,7S)-2-oxo-3-oxa-1-azaspiro[4.4]nonan-7-yl)benzyl)oxy)isoindoline-1,3-dione as a white solid. (E-2, yield=74.1%). HPLC ret. time=1.11 min (Condition EE); ESI-MS: M/Z=393.2 (M+H+).

Intermediate F2: (5R,7S)-7-(4-((aminooxy)methyl)phenyl)-3-oxa-1-azaspiro[4.4]nonan-2-one

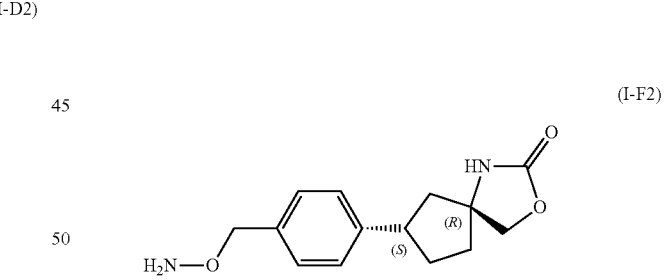

(I-F2)

To 2-((4-((5R,7S)-2-oxo-3-oxa-1-azaspiro[4.4]nonan-7-yl)benzyl)oxy) isoindoline-1,3-dione (100 mg, 0.255 mmol) in ethanol (2 mL) was added hydrazine (40.0 µl, 1.274 mmol) at room temperature over a period of 1-2 min. After stirring for 5 minutes at room temperature the solution became cloudy with a white precipitate. The contents was heated at 80° C. (oil bath temp.) for 1 h. LCMS indicated formation of the desired mass [263.0]. The reaction mixtures were cooled to room temperature. EtOH (2 mL) was added, the contents was sonicated and then filtered, and washed with additional EtOH (2×1 mL). The solvent was removed under reduced pressure. Saturated NaHCO$_3$ (3 mL) was added to the mixture which was extracted with ethyl acetate three times. The organic layers were combined and concentrated under reduced pressure to provide 26 mg of the crude product. HPLC ret. time=0.84 min (Condition EE); ESI-MS: M/Z=263.3 (M+H+).

The examples in Table 2 were prepared according to the general procedure used in the synthesis of Example 15 from Intermediate F-2.

To a reaction vial were added 1-(5-bromopyridin-2-yl)ethanone (215 mg, 1.075 mmol), ethyl 1-((diphenylmethylene)amino)cyclopent-3-enecarboxylate (515 mg, 1.612 mmol), Et$_3$N (0.300 mL, 2.150 mmol) and 1,1'-bis(di-tert-butylphosphino)ferrocene palladium dichloride (35.0 mg, 0.054 mmol) into DMA (4 mL) under N$_2$. The vial was

TABLE 2

| Ex. No. | Structure | MW | HPLC ret. time (min.) | HPLC condition | MS (M+1) |
|---|---|---|---|---|---|
| 16 | 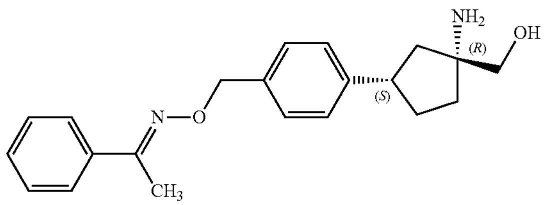 | 338.45 | 1.08 | EE | 339.5 |
| 17 | 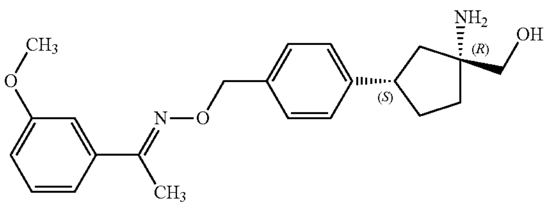 | 368.48 | 1.08 | EE | 369.3 |
| 18 | 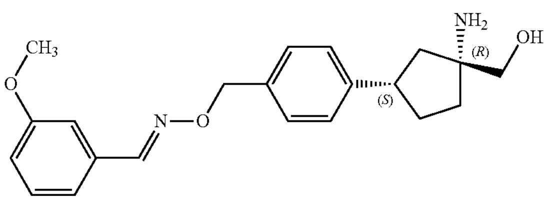 | 354.44 | 1.06 | EE | 355.4 |

Examples 19 to 20

Ethyl 4-(6-acetylpyridin-3-yl)-1-aminocyclopent-2-enecarboxylate

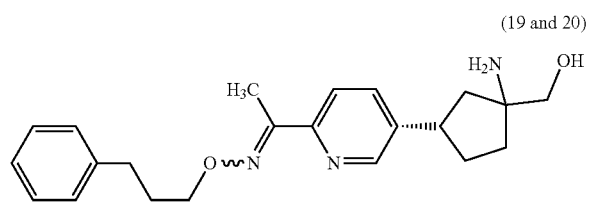

(19 and 20)

Preparation 19A: Ethyl 4-(6-acetylpyridin-3-yl)-1-aminocyclopent-2-ene-1-carboxylate sealed and heated in an oil bath at 120° C. for 15 hours. LCMS showed the desired compound with protected amine had formed. The materials were poured into 80 ml of CH$_2$Cl$_2$ and washed with 0.5N NaOH. The organic layer was then concentrated and purified on silica gel column 80 g column. 0-70% Sol B gradient in 30 mins. Sol A: hexane; Sol B: ethyl acetate. The product containing fractions were collected and the solvent was evaporated to provide the product (120 mg) as a yellow oil. The material was redissolved into ethanol (4 mL). Next, 2 ml of 1N HCl was added. The mixture was allowed to stir at room temperature for 2 hours. LCMS showed the desired deprotected product formed. HPLC ret. time=0.57 min (condition G); LC/MS M+1 (condition G)=275.1.

Preparation 19B: ethyl 3-(6-acetylpyridin-3-yl)-1-aminocyclopentanecarboxylate

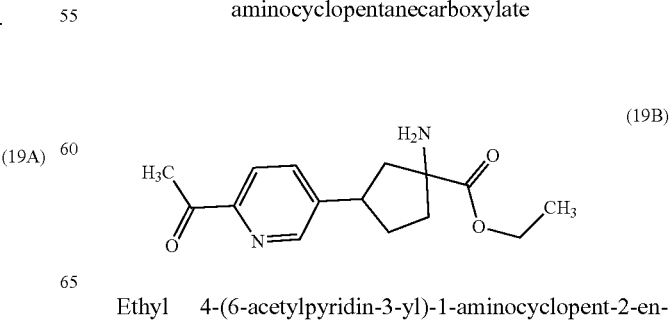

Ethyl 4-(6-acetylpyridin-3-yl)-1-aminocyclopent-2-enecarboxylate (140 mg, 0.510 mmol) was dissolved into ethyl acetate (5 mL). Pd/C (65.2 mg, 0.031 mmol) was added and the flask was purged with $N_2$. The mixtures were allowed to stir under an atmosphere of hydrogen (via a balloon) for 3 hours. LCMS showed completed conversion. The catalyst was filtered off and the reaction mixture was concentrated. HPLC ret. time=0.56 min (condition G); LC/MS M+(condition G)=277.1.

Preparation 19C: (E)-ethyl 1-amino-3-(6-(1-((3-phenylpropoxy)imino)ethyl)pyridin-3-yl)cyclopentanecarboxylate

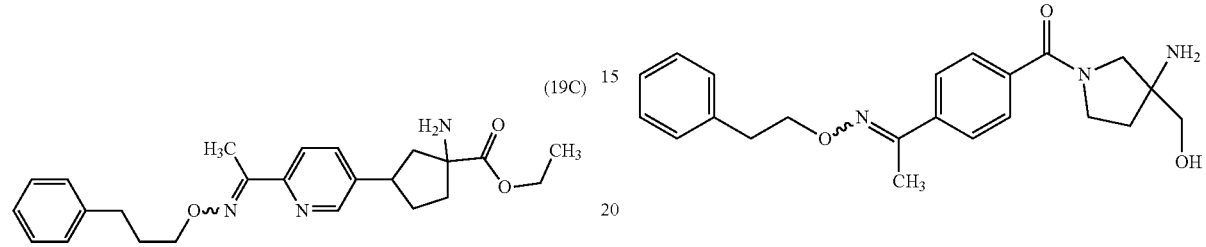

(19C)

To ethyl 3-(6-acetylpyridin-3-yl)-1-aminocyclopentanecarboxylate (100 mg, 0.362 mmol) in ethanol (3 mL) were added O-(3-phenylpropyl)hydroxylamine (109 mg, 0.724 mmol) followed by pyridine (0.088 mL, 1.086 mmol) at room temperature. The reaction mixture was heated at 60° C. (oil bath temp.) for 2 h. LCMS indicated the reaction was completed. The mixture was poured into 100 ml ethyl acetate and washed with saturated $NaHCO_3$ and brine. The organic layer was then dried over $Na_2SO_4$, concentrated, and further dried under vacuum. HPLC ret. time=0.83 min (condition G); LC/MS M+=410.2.

Examples 19 and 20

(E)-ethyl 1-amino-3-(6-(1-((3-phenylpropoxy)imino) ethyl)pyridin-3-yl) cyclopentanecarboxylate (140 mg, 0.256 mmol) was dissolved into MeOH (6 mL). The mixture was cooled down to 0° C. in an ice bath and $NaBH_4$ (38.8 mg, 1.026 mmol) was added in portions. The mixture was allowed to warm to room temperature and then stirred at room temperature for 4 hours. LCMS showed the reaction to be complete. The reaction was quenched with 2N HCl. The crude materials were purified on reverse phase HPLC. The product containing fractions were evaporated to afford 42 mg of the product as a mixture of diastereomers which was further purified by chiral SFC.

Column: YMC ProC18 S5 ODS 4.6×50 mm Oven Temp.=40° C.; Conditions: (Start % B=0; Final % B=100); Gradient Time=8 min; Flow Rate=2.5 ml/min; Detection Wavelength=220 nm; Solvent Pair=MeOH/$H_2$/TFA; Solvent A=10% MeOH-90% $H_2O$-0.2% $H_3PO_4$; Solvent B=90% MeOH-10% $H_2O$-0.2% $H_3PO_4$. Two isolates were recovered, with one a mixture of diastereomers (PK1) and the other was homochiral (PK2).

PK1: HPLC ret. time=4.91 min (Condition BB) LC/MS M+1=368.2. $^1$H NMR (400 MHz, METHANOL-$d_4$) δ 8.59-8.48 (m, 1H), 8.03-7.91 (m, 2H), 7.39-7.11 (m, 5H), 4.29 (t, J=6.4 Hz, 2H), 3.75-3.62 (m, 2H), 2.78 (t, J=7.6 Hz, 2H), 2.32 (s, 3H), 2.42-2.22 (m, 3H), 2.18-1.69 (m, 6H).

PK2: HPLC ret. time=4.92 min (Condition BB) LC/MS M+1=368.2. $^1$H NMR (400 MHz, METHANOL-$d_4$) δ 8.52 (d, J=2.0 Hz, 1H), 8.04-7.90 (m, 2H), 7.37-7.11 (m, 5H), 4.29 (t, J=6.4 Hz, 2H), 3.75-3.66 (m, 2H), 3.51 (br. s., 1H), 2.78 (t, J=7.6 Hz, 2H), 2.32 (s, 3H), 2.42-2.23 (m, 3H), 2.17-2.05 (m, 2H), 1.99-1.81 (m, 3H).

Examples 21 and 22

(3-amino-3-(hydroxymethyl)pyrrolidin-1-yl)(4-(1-(phenethoxyimino)ethyl)phenyl) methanone

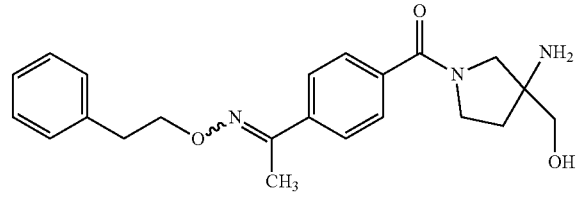

(21 and 22)

Preparation 21A: 1-(4-bromobenzoyl)-3-((tert-butoxycarbonyl)amino)pyrrolidine-3-carboxylic Acid

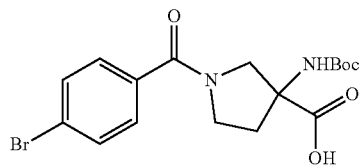

(21A)

4-Bromobenzoyl chloride (343 mg, 1.563 mmol) and 3-((tert-butoxycarbonyl) amino)pyrrolidine-3-carboxylic acid (300 mg, 1.303 mmol) and Hunig's Base (0.273 mL, 1.563 mmol) were dissolved into $CH_2Cl_2$ (8 mL) at 0° C. The mixture was allowed to stir at 0° C. for 10 min. before the ice bath was removed. The mixture was stirred at room temperature for 2 hours. LCMS showed the reaction was completed. The solvent was evaporate and the resulting residue was poured into 150 ml of EA, washed with 0.5M HCl. The aqueous layer was extracted an additional time with EA. The organic layers were combined and dried over $Na_2SO_4$ to provide 560 mg of crude material. HPLC ret. time=0.79 min (condition G); LC/MS M+=357.1.

Preparation 21B: methyl 3-amino-1-(4-bromobenzoyl)pyrrolidine-3-carboxylate, HCl

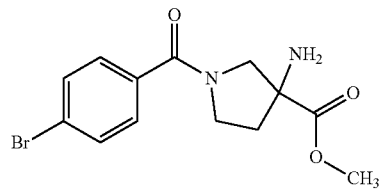

(21B)

1-(4-bromobenzoyl)-3-((tert-butoxycarbonyl)amino)pyrrolidine-3-carboxylicacid (560 mg, 1.355 mmol) was dissolved into MeOH (4 mL). HCl (2 mL, 8.00 mmol) was added slowly. The mixture was stirred at room temperature overnight. LCMS showed the reaction was completed. The solvent and extra HC were removed by evaporation under vacuum. The resulting solid material was dried under vacuum overnight to provide 600 mg of crude material. HPLC ret. time=0.58 min (condition G); LC/MS M+[1]=327.1.

Preparation 21C: (3-amino-3-(hydroxymethyl)pyrrolidin-1-yl)(4-bromophenyl) methanone

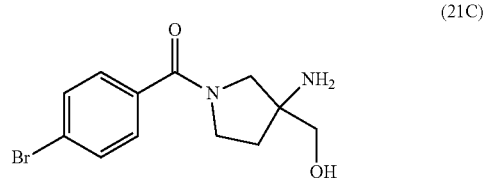 [SMILES: NC1(CO)CCN(C(=O)c2ccc(Br)cc2)C1]

(21C)

Methyl 3-amino-1-(4-bromobenzoyl)pyrrolidine-3-carboxylate (600 mg, 1.284 mmol) was dissolved into MeOH (8 mL). The mixture was cooled to 0° C. with an ice-bath. $NaBH_4$ (389 mg, 10.27 mmol) was added in portions at 0° C. After 20 mins stirring ice bath was removed. The mixture was stirred at room temperature overnight. LCMS showed >95% conversion. The reaction was quenched by the addition of 5 ml 3N HCl. The mixture was stirred at room temperature for 40 mins. The material was partitioned between 20 ml of 1N HCl and 25 ml of ethyl acetate. The aqueous layer was basified with 15% NaOH to pH 9 and extracted with ethyl acetate three times. The organic layers were combined, dried over $Na_2SO_4$, and concentrated to afford 160 mg of product. HPLC ret. time=0.54 min (condition G); LC/MS M+[1]=299.08.

Preparation 21D: 1-(4-(3-amino-3-(hydroxymethyl)pyrrolidine-1-carbonyl)phenyl) Ethanone

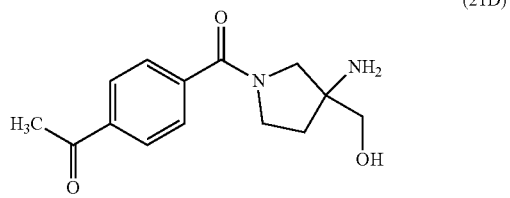

(21D)

To (3-amino-3-(hydroxymethyl)pyrrolidin-1-yl)(4-bromophenyl)methanone (160 mg, 0.535 mmol) in dioxane (2 mL) was added tributyl(1-ethoxyvinyl)stannane (0.235 mL, 0.695 mmol) followed by bis(triphenylphosphine)palladium (II) chloride (30.0 mg, 0.043 mmol) at room temperature. The mixture was evacuated, back flushed with nitrogen (2×), and heated at 110° C. for 6 h. The reaction mixture was cooled to room temperature and filtered. The filter cake was washed with dioxane (2 mL×2).

To the filtrate was added 1 mL of 4N HCl in dioxane dropwise over 1 min. at room temperature. The homogenous reaction mixture was stirred at room temperature for 30 mins. LCMS showed the desired product peak. The reaction mixture was concentrated under reduced pressure. To the semi-solid was added acetonitrile (2 mL). The contents were sonicated for 5 min., then allowed to sit in an ice bath for 2 hours. A grey solid precipitated out. The solid was collected and purified on reverse phase HPLC to afford the product (32 mg). HPLC ret. time=0.45 min (condition G). LC/MS $M^{+1}$=263.2.

Examples 21 and 22

To 1-(4-(3-amino-3-(hydroxymethyl)pyrrolidine-1-carbonyl)phenyl)ethanone (32 mg, 0.122 mmol) in ethanol (1 mL) were sequentially added O-phenethylhydroxylamine (33.5 mg, 0.244 mmol) and pyridine (0.030 mL, 0.366 mmol) at room temperature. The reaction mixture was heated at 70° C. (oil bath temp.) for 2 h at which time LCMS analysis indicated the reaction was complete. The crude material was purified on reverse phase HPLC. Column: Phen Luna-Axia C18 21.20*100 mm; SolA: 10% MeOH-90% $H_2O$-0.5% TFA; SolB: 90% MeOH-10% $H_2O$-0.5% TFA. The product containing fractions were collected and dried under high vacuum overnight to provide 18.5 mg of a racemic mixture. HPLC ret. time=0.76 min (condition G); LC/MS M+[1]=382.2.

The racemate was separated using the following method to give PK1 (early eluting) and PK2 (later eluting): Preparative Chromatographic Conditions: Instrument: Berger SFC MGII (LVL-L4021 Lab); Column: Lux Amylose 2 25×3 cm ID, 5 μm; Flow rate: 85.0 mL/min; Mobile Phase: 70/30 $CO_2$/MeOH with 0.1% DEA; Detector Wavelength: 220 nm; Sample Prep and Inj. Volume: 500 μL of 18 mg dissolved in 2 mL MeOH.

Example 21: PK1 (6.5 mg): Prep SFC Elution time: 7.4 min; $^1$H NMR (400 MHz, METHANOL-$d_4$) δ 7.76 (d, J=8.6 Hz, 2H), 7.61-7.47 (m, 2H), 7.30-7.17 (m, 5H), 4.39 (t, J=6.9 Hz, 2H), 3.86-3.48 (m, 6H), 3.03-3.01 (t, 2H), 2.20 (s, 3H), 1.41-1.22 (m, 2H).

Example 22: PK2 (6.5 mg): Prep SFC Elution time: 9.0 min.

Examples 23 and 24

(3-amino-3-(hydroxymethyl)pyrrolidin-1-yl)(4-(1-((3-phenylpropoxy)imino)ethyl) phenyl)methanone, TFA

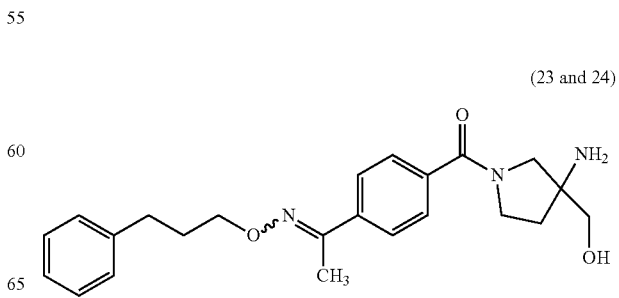

(23 and 24)

Preparation 23A: 1-(4-(3-amino-3-(hydroxymethyl) pyrrolidine-1-carbonyl)phenyl) Ethanone Aqueous Solution

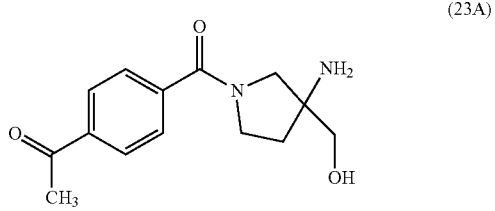 [SMILES: CC(=O)c1ccc(C(=O)N2CCC(N)(CO)C2)cc1]

(23A)

To a 2-dram vial containing a stir bar were added (3-aminopyrrolidin-3-yl) methanol, 2 HCl (25 mg, 0.132 mmol), 4-acetylbenzoic acid (21.70 mg, 0.132 mmol) and DMF to give a cloudy suspension. 1-Propanephosphonic acid cyclic anhydride (50% in ethyl acetate) (0.094 mL, 0.159 mmol) was added dropwise, followed by DIPEA (0.092 mL, 0.529 mmol). After the addition of DIPEA, the suspension slowly cleared up. The reaction mixture was stirred at room temperature for 1.5 h, at which time LCMS analysis showed completed conversion to desired product.

The reaction was quenched with 1.5 mL of 1N HCl. The reaction mixture was stirred for 20-30 minutes before EtOAc (4 ml) was added. The aqueous phase was washed with additional EtOAc (1×4 ml) and the organics were back-extracted with 1N HCl (2 mL). The aqueous solution of the obtained material was used in subsequent transformations. HPLC ret. time=0.44 min (condition G); LC/MS $M^{+1}$=263.1.

Examples 23 and 24

To the aqueous HCl phase containing 1-(4-(3-amino-3-(hydroxymethyl) pyrrolidine-1-carbonyl)phenyl)ethanone was added O-(3-phenylpropyl)hydroxylamine (22 mg, 0.145 mmol) followed by EtOH (2 mL). The resulting clear solution was stirred in an oil bath set to 60° C. for 1 hour, at which time LCMS analysis showed the intermediate to be consumed with one major peak corresponding to the desired product's expected mass. The solution was filtered through a syringe filter to remove the slight cloudiness and purified by reverse phase preparative HPLC to provide (E)-(3-amino-3-(hydroxymethyl)pyrrolidin-1-yl)(4-(1-((3-phenylpropoxy)imino)ethyl)phenyl) methanone, TFA (35.2 mg, 0.068 mmol, 51.2% yield) as a thick oil. HPLC ret. time=0.80 min (condition G); LC/MS $M^{+1}$=396.2. $^1$H NMR (500 MHz, METHANOL-$d_4$) δ 7.83 (d, J=8.3 Hz, 2H), 7.62 (br. s., 2H), 7.30 (d, J=7.2 Hz, 2H), 7.27-7.23 (m, 2H), 7.20 (s, 1H), 4.25 (t, J=6.4 Hz, 2H), 3.85 (br. s., 6H), 2.82-2.76 (m, 2H), 2.29 (s, 3H), 2.23-2.14 (m, 1H), 2.12-2.04 (m, 2H), 1.30 (d, J=6.4 Hz, 1H).

The racemate was separated using the following method to give PK1 (early eluting) and PK2 (later eluting): Preparative Chromatographic Conditions: Instrument: Berger SFC MGII; Column: Chiral AS-H 25×3 cm ID, 5 μm; Flow rate: 85.0 mL/min; Mobile Phase: 75/25 $C_{O2}$/MeOH w/0.1% DEA; Detector Wavelength: 220 nm; Sample Prep: dissolved in 2 mL MeOH.

Example 23: PK1: 11.4 mg. Ret. Time=5.35 min (Chiral SFC); HPLC ret. time=0.82 min (condition G); LC/MS $M^{+1}$=396.3.

Example 24: PK2: 14.7 mg. Ret. Time=7.37 min (Chiral SFC); HPLC ret. time=0.81 min (condition G); LC/MS $M^{+1}$=396.2.

The Examples in Table 3 were prepared according to the general procedure for Examples 23 and 24.

TABLE 3

| Ex. No. | Structure | MW | HPLC ret. time (min.) | HPLC condition | MS ($M^{+1}$) | Comment |
|---|---|---|---|---|---|---|
| 25 | | 517.3 | 3.79 | K | 518.3 | Separated (PK1) |
| 26 | | | | | | (PK2) |

TABLE 3-continued

| Ex. No. | Structure | MW | HPLC ret. time (min.) | HPLC condition | MS (M+1) | Comment |
|---|---|---|---|---|---|---|
| 27 (PK1) 28 (PK2) | 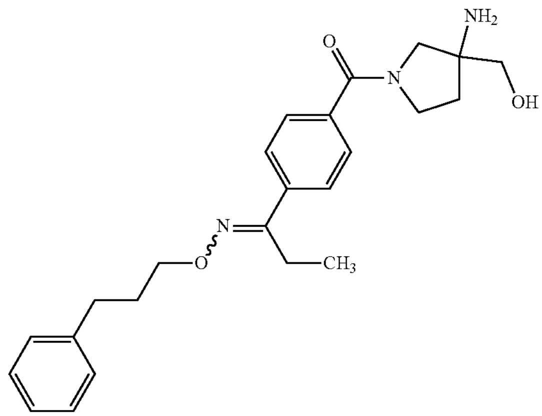 [SMILES: CCC(=NOCCCc1ccccc1)c1ccc(C(=O)N2CCC(N)(CO)C2)cc1] | 409.2 | 3.20 | K | 410.2 | Separated |
| 29 (PK1) 30 (PK2) | 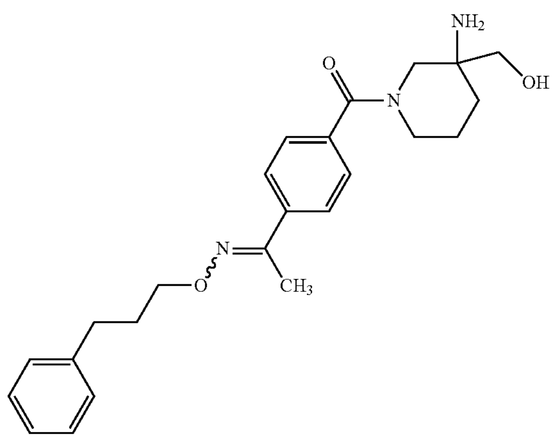 [SMILES: CC(=NOCCCc1ccccc1)c1ccc(C(=O)N2CCCC(N)(CO)C2)cc1] | 409.5 | 5.67 | N | 410.2 | Separated |
| 31 (PK1) 32 (PK2) | 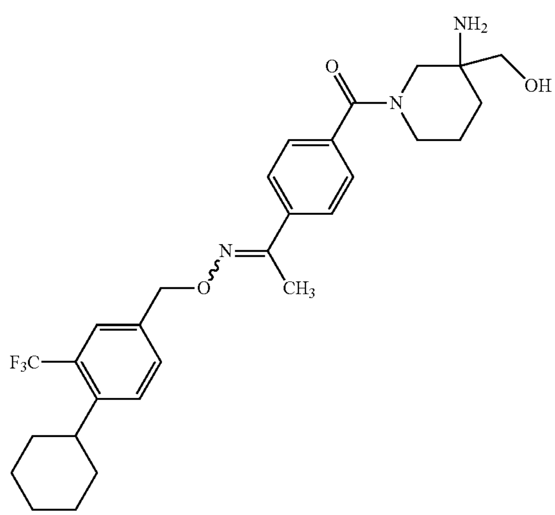 [SMILES: CC(=NOCc1ccc(C2CCCCC2)c(C(F)(F)F)c1)c1ccc(C(=O)N2CCCC(N)(CO)C2)cc1] | 531.6 | 7.24 | N | 532.2 | Separated |

TABLE 3-continued

| Ex. No. | Structure | MW | HPLC ret. time (min.) | HPLC condition | MS (M$^{+1}$) | Comment |
|---|---|---|---|---|---|---|
| 33 | 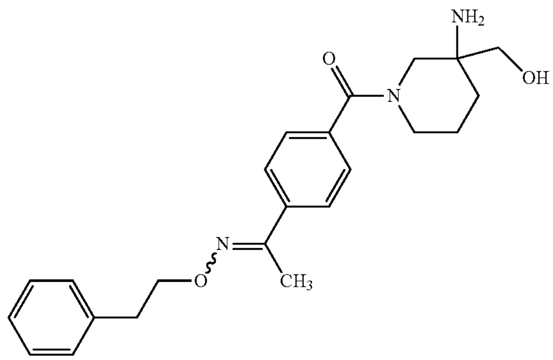 [SMILES: CC(=NOCCc1ccccc1)c1ccc(C(=O)N2CCCC(N)(CO)C2)cc1] | 395.2 | 0.78 | G | 396.3 | Racemic |
| 34 | 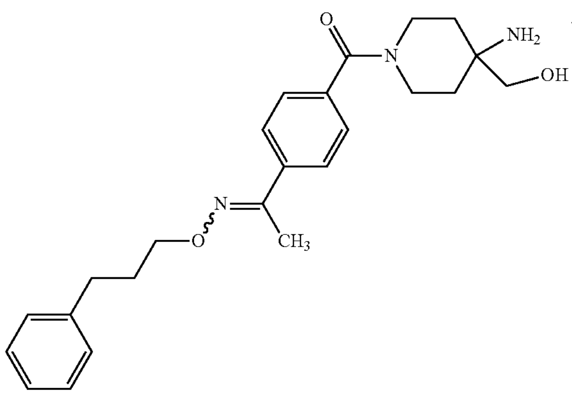 [SMILES: CC(=NOCCCc1ccccc1)c1ccc(C(=O)N2CCC(N)(CO)CC2)cc1] | 409.2 | 3.08 | K | 410.3 | Achiral |
| 35 | 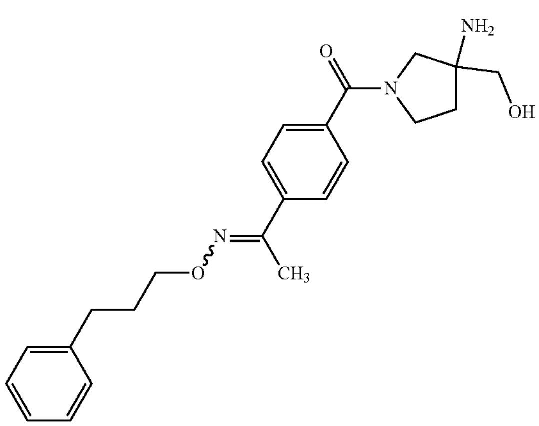 [SMILES: CC(=NOCCCc1ccccc1)c1ccc(C(=O)N2CCC(N)(CO)C2)cc1] | 449.5 | 0.85 | G | 450.2 | Racemic |

Example 36

(E)-1-(4-((4-amino-4-(hydroxymethyl)piperidin-1l-yl)sulfonyl)phenyl)ethanone O-(3-phenylpropyl) Oxime, TFA

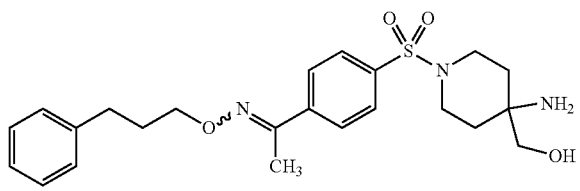
(36)

Preparation 36A: 1-(4-((4-amino-4-(hydroxymethyl) piperidin-1-yl)sulfonyl)phenyl) ethanone

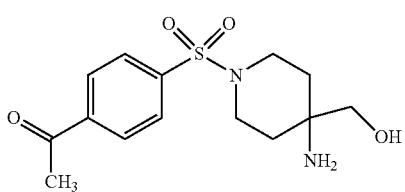
(36A)

4-Acetylbenzene-1-sulfonyl chloride (88 mg, 0.403 mmol) and (4-aminopiperidin-4-yl)methanol (50 mg, 0.384 mmol) were dissolved into $CH_2Cl_2$ (4 mL). DIPEA was added (0.080 mL, 0.461 mmol) into the mixture. The mixture was stirred at room temperature for 2 hours. The reaction was quenched with 1N HCl (4 mL). The mixture was stirred at room temperature for 40 min. The phases were separated and the $CH_2Cl_2$ layer was extracted with 1N HCl (2 mL). The aqueous layers were combined to afford a total of ~5 ml. HPLC ret. time=0.55 min (condition G); LC/MS $M+^1$=313.1.

Example 36

To 2 mL (⅓ of the prepared amount) of the aqueous solution of 1-(4-((4-amino-4-(hydroxymethyl)piperidin-1-yl)sulfonyl)phenyl)ethanone (0.130 mmol) in 2 ml aqueous solution was added ethanol (1 mL) followed by 0-(3-phenylpropyl) hydroxylamine (35.0 mg, 0.231 mmol) at room temperature. The mixture was stirred at room temperature overnight, at which time LCMS analysis indicated complete conversion of the starting material. The crude materials were purified on reverse phase HPLC. Column: Phen Luna-Axia C18 21.2*100 mm SolA: 10% MeOH-90% $H_2O$-0.1% TFA; SolB: 90% MeOH-10% $H_2O$-0.5% TFA. The fractions containing the desired product were collected and evaporated under vacuum to afford (E)-1-(4-((4-amino-4-(hydroxymethyl)piperidin-1-yl)sulfonyl)phenyl)ethanone O-(3-phenylpropyl) oxime, TFA (16 mg, 20% yield). HPLC ret. time=1.90 min (condition M); LC/MS $M+^1$=446.1. $^1H$ NMR (400 MHz, METHANOL-$d_4$) δ 7.96 (d, J=8.6 Hz, 2H), 7.84 (d, J=8.8 Hz, 2H), 7.35-7.12 (m, 5H), 4.26 (t, J=6.4 Hz, 2H), 3.51-3.42 (m, 4H), 2.93 (br. s., 2H), 2.78 (t, J=7.6 Hz, 2H), 2.30 (s, 3H), 2.14-1.97 (m, 4H), 1.87 (br. s., 2H).

Example 37 was prepared according to the general procedure for Example 36.

TABLE 4

| Ex. No. | Structure | MW | HPLC ret. time (min.) | HPLC condition | MS ($M^{+1}$) | Comment |
|---|---|---|---|---|---|---|
| 37 | 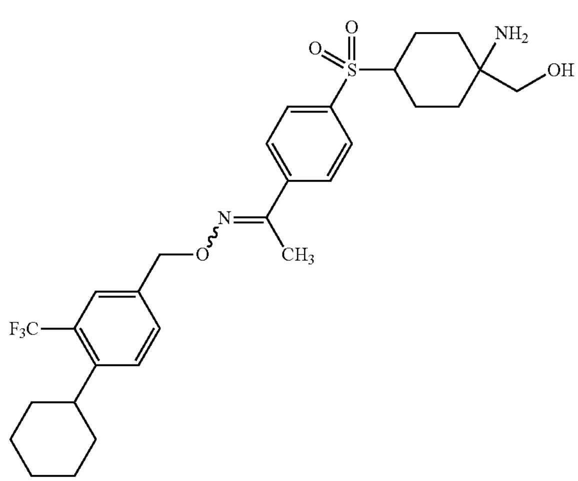 [SMILES: CC(=NOCc1ccc(C2CCCCC2)c(C(F)(F)F)c1)c1ccc(S(=O)(=O)C2CCC(N)(CO)CC2)cc1] | 567.7 | 2.17 | M | 568.2 | Achiral |

Example 38

(((1R,3R)-1-amino-3-(4-(1-((cyclopropylmethoxy)imino)ethyl)phenyl)cyclopentyl)methyl Dihydrogen Phosphate

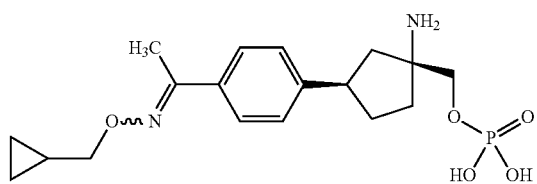

(38)

To a cloudy solution of 1-(4-((1R,3R)-3-amino-3-(hydroxymethyl)cyclopentyl) phenyl)ethanone O-cyclopropylmethyl oxime (8 mg, 0.026 mmol) in anhydrous acetonitrile (1 mL) at 0° C. was added pyrophosphoryl chloride (0.026 mL, 0.185 mmol). The clear solution obtained was allowed to stir at the same temperature for 5 mins, then at room temperature for 3.5 hr. LCMS analysis indicated >80% conversion. Water (0.3 mL) was added and the solution was allowed to stir at room temperature for 40 min. The reaction mixture was then purified on reverse phase HPLC. (Column: Phen Luna-Axia C18 5 um 21.2*100 mm. Sol A: 10% MeOH-90% $H_2O$-0.5% TFA; Sol B: 90% MeOH-10% $H_2O$-0.5% TFA). The product containing fractions were collected and dried under high vacuum overnight to provide ((1R, 3R)-1-amino-3-(4-(1-((cyclopropylmethoxy) imino)ethyl)phenyl)cyclopentyl)methyl dihydrogen phosphate (2.07 mg, 19.4% yield) as a white solid. HPLC ret. time=0.71 min (condition G); LC/MS M+1=383.2. $^1$H NMR (400 MHz, METHANOL-$d_4$) δ 7.65 (d, J=8.4 Hz, 2H), 7.34 (d, J=8.4 Hz, 2H), 4.09-3.98 (m, 4H), 2.37-2.27 (m, 4H), 2.25 (s, 3H), 1.98-1.82 (m, 3H), 1.23 (br. s., 1H), 0.63-0.55 (m, 2H), 0.40-0.30 (m, 2H).

The Examples in Table 5 were prepared according to the general procedure of Example 38 from the corresponding alcohol precursors.

TABLE 5

| Ex. No. | Structure | MW | HPLC ret. time (min.) | HPLC condition | MS (M$^{+1}$) |
|---|---|---|---|---|---|
| 39 | 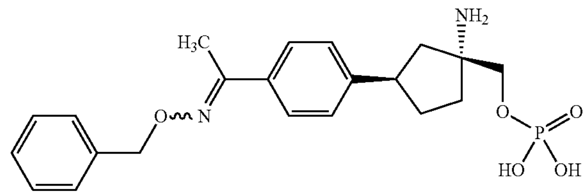 [SMILES: CC(=NOCc1ccccc1)c1ccc([C@@H]2CC[C@](N)(COP(=O)(O)O)C2)cc1] | 418.4 | 2.89 | K | 419.2 |
| 40 | 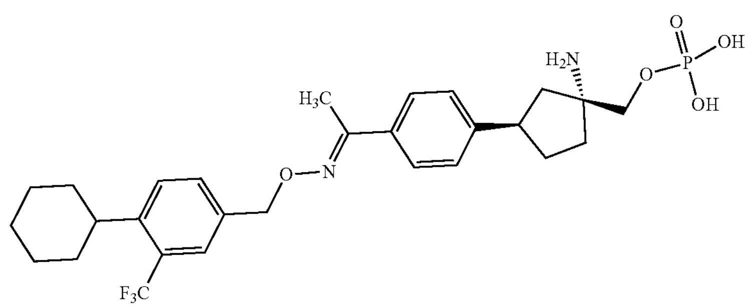 [SMILES: C/C(=N\OCc1ccc(C2CCCCC2)c(C(F)(F)F)c1)c1ccc([C@@H]2CC[C@](N)(COP(=O)(O)O)C2)cc1] | 568.6 | 4.05 | K | 569.2 |
| 41 | 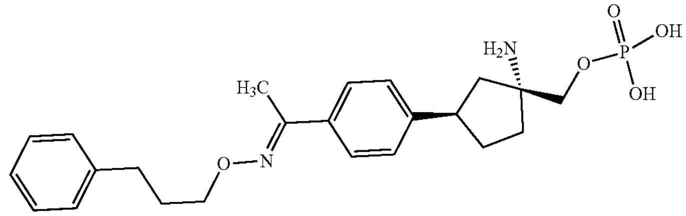 [SMILES: C/C(=N\OCCCc1ccccc1)c1ccc([C@@H]2CC[C@](N)(COP(=O)(O)O)C2)cc1] | 446.5 | 3.22 | K | 447.2 |
| 42 | 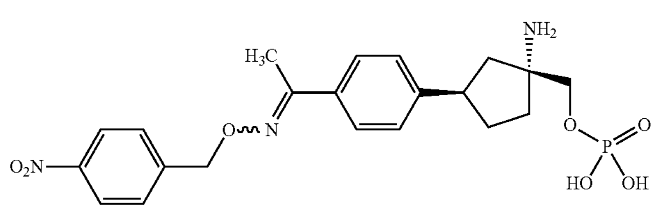 [SMILES: CC(=NOCc1ccc([N+](=O)[O-])cc1)c1ccc([C@@H]2CC[C@](N)(COP(=O)(O)O)C2)cc1] | 463.4 | 3.05 | K | 464.3 |

TABLE 5-continued

| Ex. No. | Structure | MW | HPLC ret. time (min.) | HPLC condition | MS (M+1) |
|---|---|---|---|---|---|
| 43 | 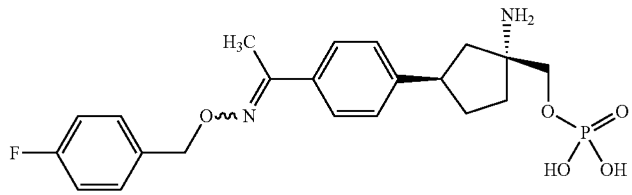 [SMILES: CC(=NOCc1ccc(F)cc1)c1ccc([C@@H]2CC[C@](N)(COP(=O)(O)O)C2)cc1] | 436.4 | 3.16 | K | 437.4 |
| 44 | 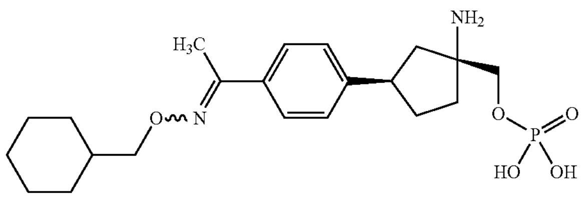 [SMILES: CC(=NOCC1CCCCC1)c1ccc([C@@H]2CC[C@](N)(COP(=O)(O)O)C2)cc1] | 424.5 | 3.66 | K | 425.4 |
| 45 | 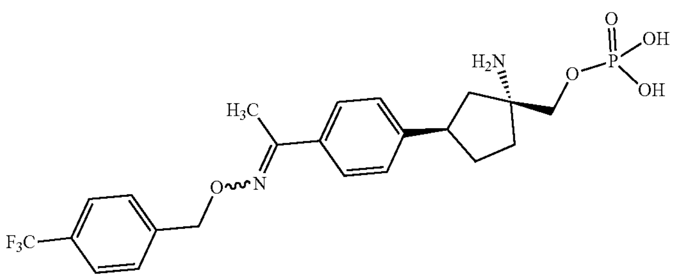 [SMILES: CC(=NOCc1ccc(C(F)(F)F)cc1)c1ccc([C@@H]2CC[C@](N)(COP(=O)(O)O)C2)cc1] | 486.4 | 3.50 | K | 487.2 |
| 46 | 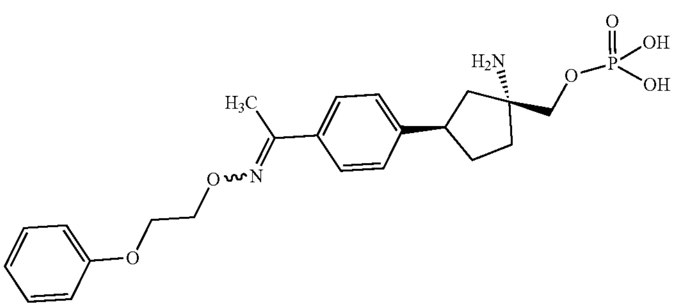 [SMILES: CC(=NOCCOc1ccccc1)c1ccc([C@@H]2CC[C@](N)(COP(=O)(O)O)C2)cc1] | 448.4 | 3.09 | K | 449.2 |
| 47 | 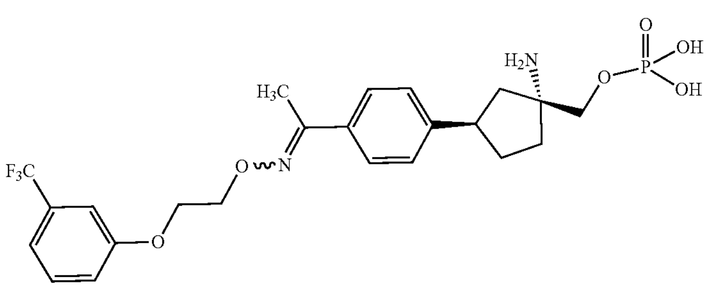 [SMILES: CC(=NOCCOc1cccc(C(F)(F)F)c1)c1ccc([C@@H]2CC[C@](N)(COP(=O)(O)O)C2)cc1] | 516.4 | 3.49 | K | 517.2 |
| 48 | 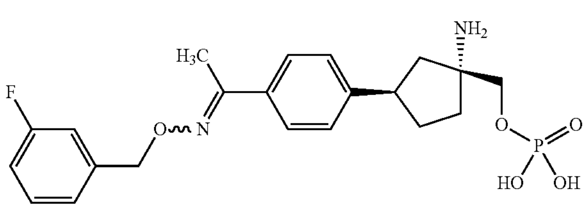 [SMILES: CC(=NOCc1cccc(F)c1)c1ccc([C@@H]2CC[C@](N)(COP(=O)(O)O)C2)cc1] | 436.4 | 3.18 | K | 437.3 |

TABLE 5-continued
| Ex. No. | Structure | MW | HPLC ret. time (min.) | HPLC condition | MS (M+1) |
|---|---|---|---|---|---|
| 49 | 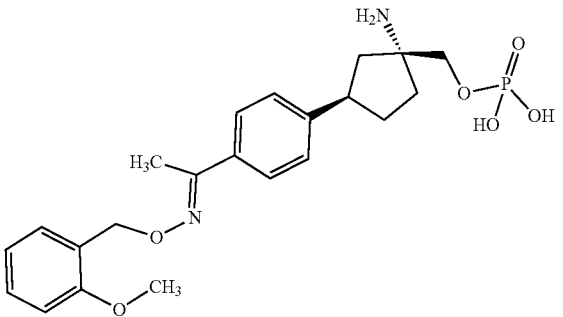 [SMILES: COc1ccccc1CO/N=C(\C)c1ccc([C@@H]2CC[C@](N)(COP(=O)(O)O)C2)cc1] | 448.17 | 3.14 | K | 449.4 |
| 50 | 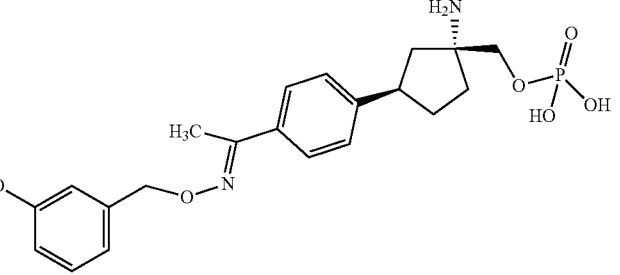 | 448.17 | 3.09 | K | 449.4 |
| 51 | 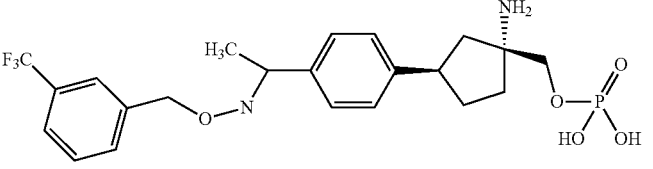 [SMILES: CC(NOCc1cccc(C(F)(F)F)c1)c1ccc([C@@H]2CC[C@](N)(COP(=O)(O)O)C2)cc1] | 486.15 | 3.46 | K | 487.1 |
| 52 | 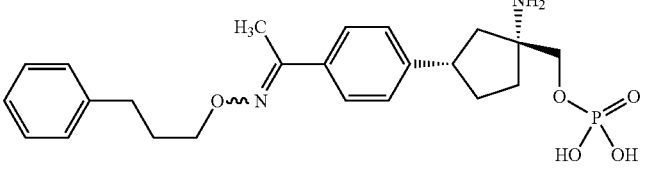 | 446.5 | 3.51 | K | 447.2 |
| 53 | 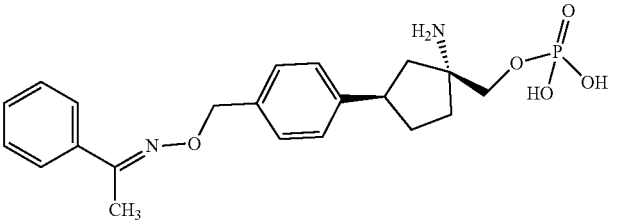 [SMILES: C/C(=N\OCc1ccc([C@@H]2CC[C@](N)(COP(=O)(O)O)C2)cc1)c1ccccc1] | 418.17 | 3.06 | K | 419.1 |
| 54 | 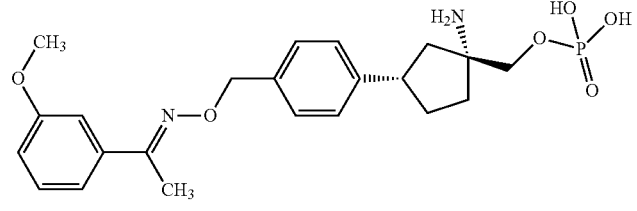 [SMILES: COc1cccc(/C(C)=N/OCc2ccc([C@H]3CC[C@](N)(COP(=O)(O)O)C3)cc2)c1] | 448.46 | 1.02 | EE | 449.4 |

Example 55

(3-amino-1-(4-(1-(phenethoxyimino)ethyl)benzoyl)pyrrolidin-3-yl)methyl Dihydrogen Phosphate

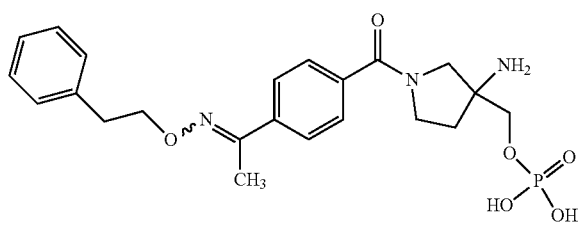

(55)

To a solution of (3-amino-3-(hydroxymethyl)pyrrolidin-1-yl)(4-(1-(phenethoxyimino)ethyl)phenyl)methanone (3 mg, 7.86 μmol) in anhydrous acetonitrile (1 ml) at 0° C. was added pyrophosphoryl chloride (9.79 μl, 0.071 mmol). The resulting clear solution was stirred at 0° C. for 15 min, then at room temperature for overnight. LCMS showed more than 90% conversion. The reaction was quenched with 0.3 ml water. The reaction mixture was stirred at room temperature for 40 min. The reaction mixture was then purified on reverse phase HPLC. Column: Phen Luna-Axia C18 5 um 30*100 mm, SolA: 0.1% TFA in Water: SolB: 0.1% TFA in MeCN. The fractions were collected and dried under high vacuum overnight to provide 1.63 mg of product as a white solid, 40% yield. HPLC Ret. time=2.91 min (condition K). LC/MS $M^{+1}$=462.4.

The Examples in Table 6 were prepared according to the general procedure for Example 55.

TABLE 6

| Ex. No. | Structure | MW | HPLC ret. time (min.) | HPLC condition | MS ($M^{+1}$) |
|---|---|---|---|---|---|
| 56 | 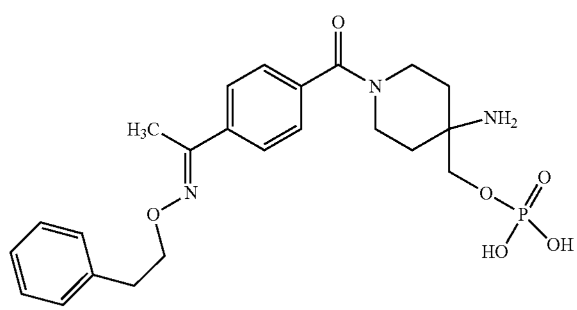 [SMILES: C/C(=N\OCCc1ccccc1)c1ccc(C(=O)N2CCC(N)(COP(=O)(O)O)CC2)cc1] | 475.47 | 6.46 | L | 476.3 |
| 57 | 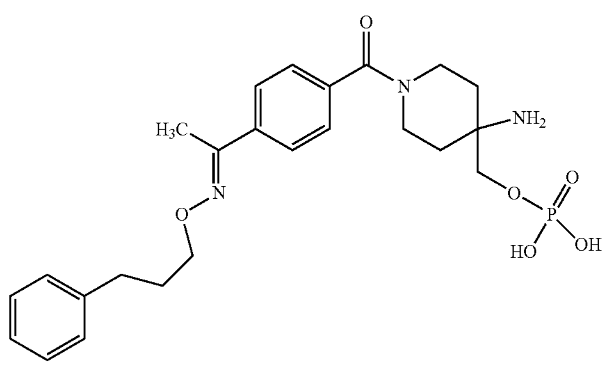 [SMILES: C/C(=N\OCCCc1ccccc1)c1ccc(C(=O)N2CCC(N)(COP(=O)(O)O)CC2)cc1] | 489.5 | 6.85 | L | 490.3 |
| 58 | 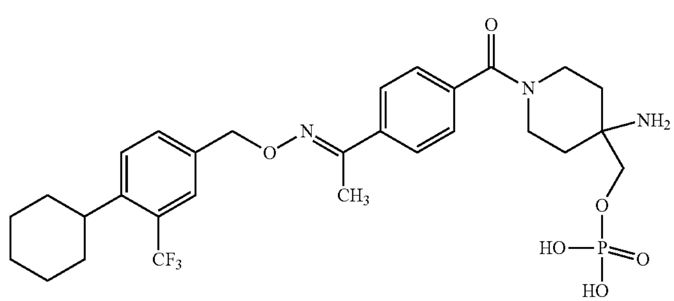 [SMILES: C/C(=N\OCc1ccc(C2CCCCC2)c(C(F)(F)F)c1)c1ccc(C(=O)N2CCC(N)(COP(=O)(O)O)CC2)cc1] | 611.24 | 7.59 | N | 612.2 |

TABLE 6-continued

| Ex. No. | Structure | MW | HPLC ret. time (min.) | HPLC condition | MS (M$^{+1}$) |
|---|---|---|---|---|---|
| 59 (PK1) 60 (PK2) | 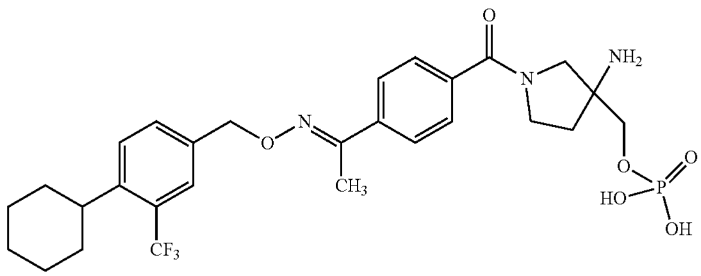 [SMILES: C/C(=N\OCc1ccc(C2CCCCC2)c(C(F)(F)F)c1)c1ccc(C(=O)N2CCC(N)(COP(=O)(O)O)C2)cc1] | 597.2 | 4.02 | K | 598.1 |
| 61 (PK1) 62 (PK2) | 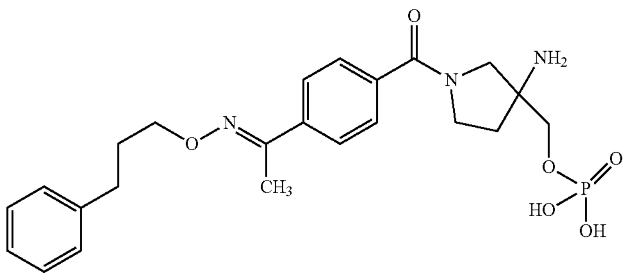 [SMILES: C/C(=N\OCCCc1ccccc1)c1ccc(C(=O)N2CCC(N)(COP(=O)(O)O)C2)cc1] | 475.47 | 3.17 | K | 476.1 |
| 63 (PK1) 64 (PK2) | 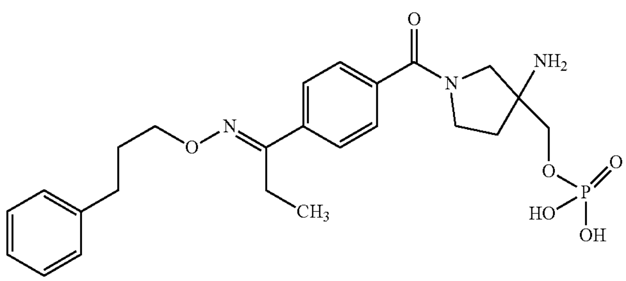 [SMILES: CC/C(=N\OCCCc1ccccc1)c1ccc(C(=O)N2CCC(N)(COP(=O)(O)O)C2)cc1] | 489.2 | 3.37 | K | 490.2 |
| 65 | 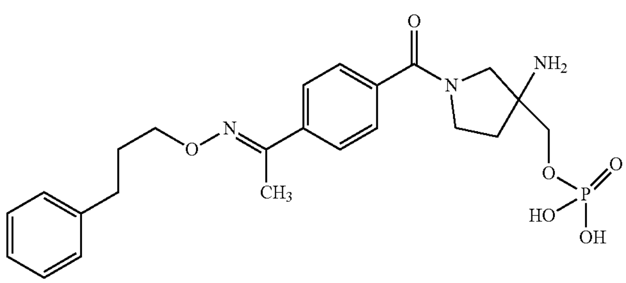 [SMILES: C/C(=N\OCCCc1ccccc1)c1ccc(C(=O)N2CCC(N)(COP(=O)(O)O)C2)cc1] | 529.16 | 3.37 | K | 530.2 |
| 66 (PK1) 67 (PK2) | 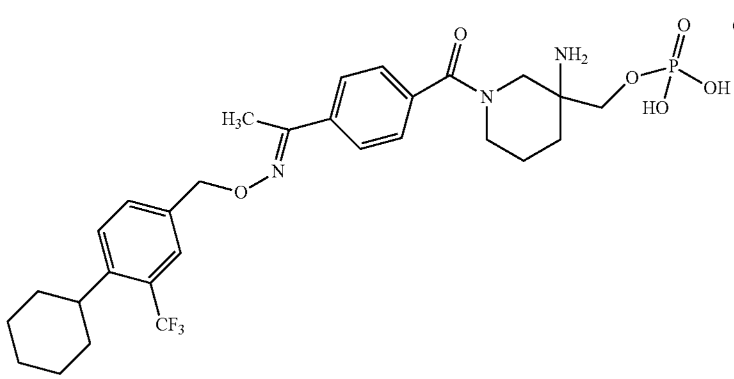 [SMILES: C/C(=N\OCc1ccc(C2CCCCC2)c(C(F)(F)F)c1)c1ccc(C(=O)N2CCCC(N)(COP(=O)(O)O)C2)cc1] | 611.24 | 7.63 | N | 612.1 |

TABLE 6-continued

| Ex. No. | Structure | MW | HPLC ret. time (min.) | HPLC condition | MS (M$^{+1}$) |
|---|---|---|---|---|---|
| 68 (PK1) 69 (PK2) | 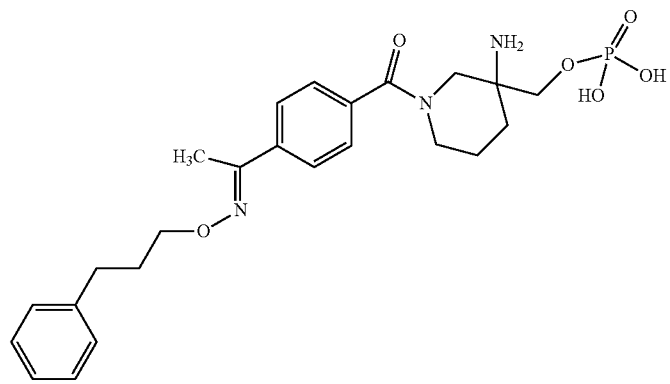 [SMILES: C/C(=N\OCCCc1ccccc1)c1ccc(C(=O)N2CCCC(N)(COP(=O)(O)O)C2)cc1] | 489.5 | 6.00 | N | 490.1 |
| 70 | 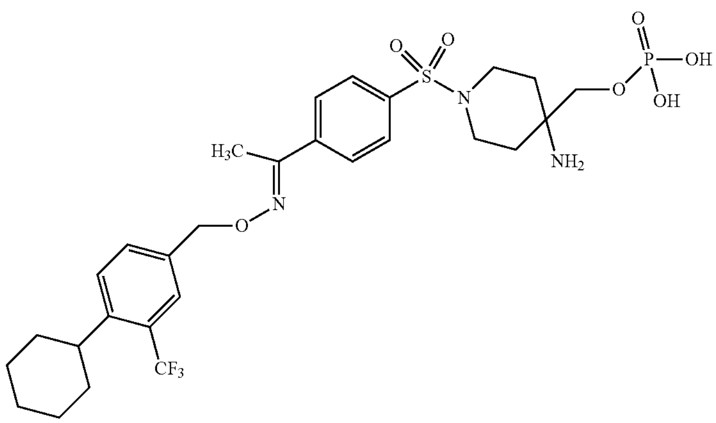 [SMILES: C/C(=N\OCc1ccc(C2CCCCC2)c(C(F)(F)F)c1)c1ccc(S(=O)(=O)N2CCC(N)(COP(=O)(O)O)CC2)cc1] | 647.2 | 7.76 | N | 648.1 |
| 71 | 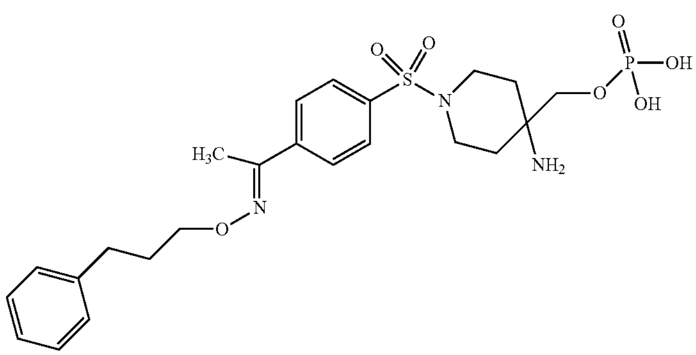 [SMILES: C/C(=N\OCCCc1ccccc1)c1ccc(S(=O)(=O)N2CCC(N)(COP(=O)(O)O)CC2)cc1] | 525.5 | 6.35 | N | 526.0 |
| 72 | 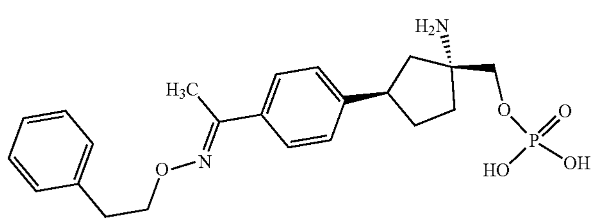 [SMILES: C/C(=N\OCCc1ccccc1)c1ccc([C@@H]2CC[C@](N)(COP(=O)(O)O)C2)cc1] | 432.45 | 2.53 | AA | 433.1 |

TABLE 6-continued

| Ex. No. | Structure | MW | HPLC ret. time (min.) | HPLC condition | MS (M+1) |
|---|---|---|---|---|---|
| 73 | 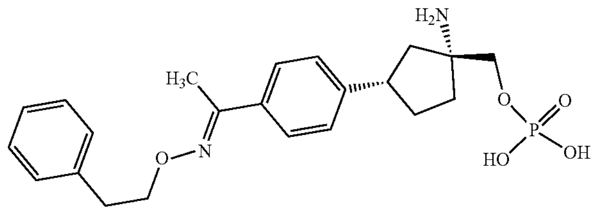 [SMILES: C/C(=N\OCCc1ccccc1)c1ccc([C@H]2CC[C@](N)(COP(=O)(O)O)C2)cc1] | 432.45 | 2.53 | AA | 433.1 |

The Examples in Table 7 were prepared according to the general procedure for Example 5.

TABLE 7

| Ex. No. | Structure | MW | HPLC ret. time (min.) | HPLC condition | MS (M+1) |
|---|---|---|---|---|---|
| 74 | 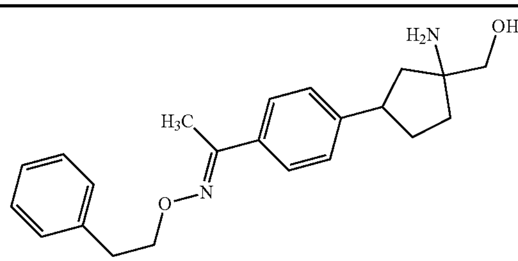 | 352.48 | 0.82 | KK | 353.3 |
| 75 | 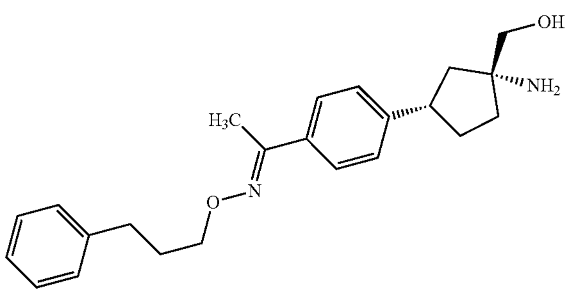 [SMILES: C/C(=N\OCCCc1ccccc1)c1ccc([C@H]2CC[C@](N)(CO)C2)cc1] | 366.51 | 0.88 | KK | 367.2 |
| 76 | 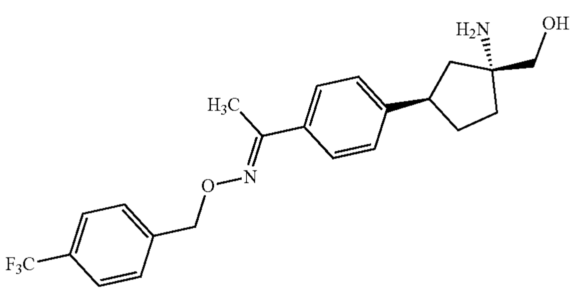 [SMILES: C/C(=N\OCc1ccc(C(F)(F)F)cc1)c1ccc([C@@H]2CC[C@](N)(CO)C2)cc1] | 406.45 | 0.87 | KK | 407.2 |
| 77 | 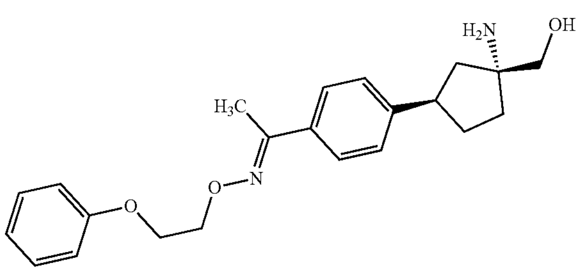 [SMILES: C/C(=N\OCCOc1ccccc1)c1ccc([C@@H]2CC[C@](N)(CO)C2)cc1] | 368.48 | 0.80 | KK | 369.2 |

TABLE 7-continued

| Ex. No. | Structure | MW | HPLC ret. time (min.) | HPLC condition | MS (M+1) |
|---|---|---|---|---|---|
| 78 | 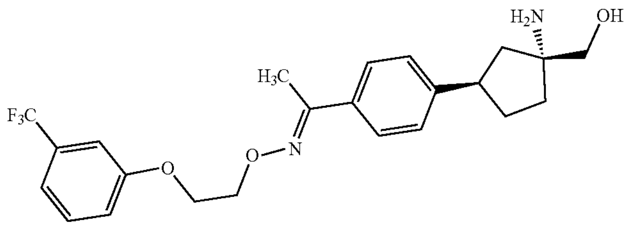 [SMILES: C/C(=N\OCCOc1cccc(C(F)(F)F)c1)c1ccc([C@@H]2CC[C@](N)(CO)C2)cc1] | 436.48 | 0.87 | KK | 437.2 |
| 79 | 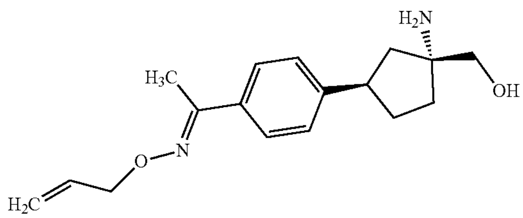 [SMILES: C=CCO/N=C(\C)c1ccc([C@@H]2CC[C@](N)(CO)C2)cc1] | 288.39 | 0.72 | KK | 289.2 |
| 80 | 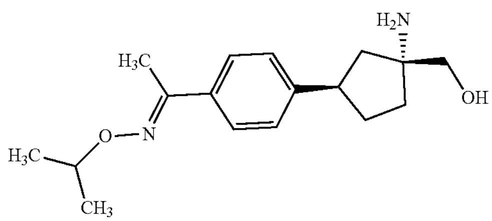 [SMILES: C/C(=N\OC(C)C)c1ccc([C@@H]2CC[C@](N)(CO)C2)cc1] | 290.41 | 0.76 | KK | 291.2 |
| 81 | 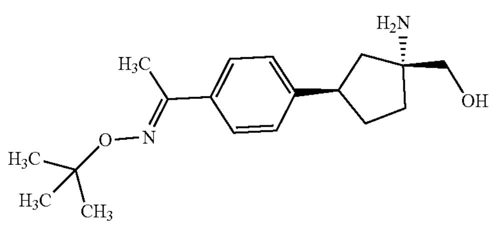 [SMILES: C/C(=N\OC(C)(C)C)c1ccc([C@@H]2CC[C@](N)(CO)C2)cc1] | 304.43 | 0.81 | KK | 305.2 |
| 82 | 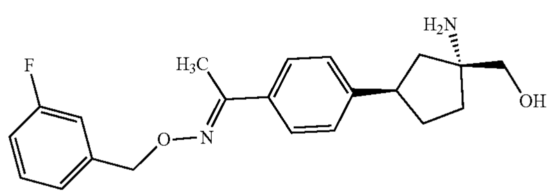 [SMILES: C/C(=N\OCc1cccc(F)c1)c1ccc([C@@H]2CC[C@](N)(CO)C2)cc1] | 356.44 | 0.80 | KK | 357.2 |
| 83 | 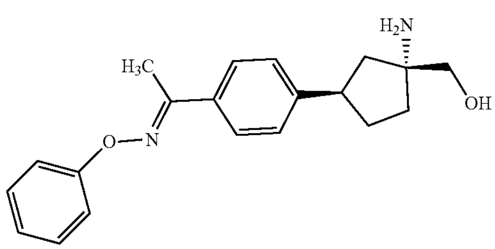 [SMILES: C/C(=N\Oc1ccccc1)c1ccc([C@@H]2CC[C@](N)(CO)C2)cc1] | 324.42 | 0.80 | KK | 325.2 |
| 84 | 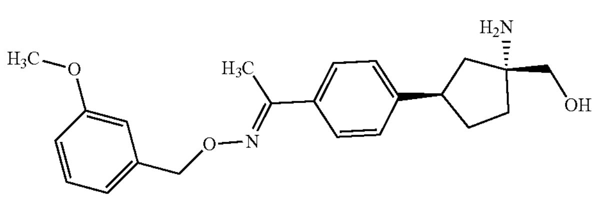 [SMILES: COc1cccc(CO/N=C(\C)c2ccc([C@@H]3CC[C@](N)(CO)C3)cc2)c1] | 368.48 | 0.81 | KK | 369.2 |

TABLE 7-continued

| Ex. No. | Structure | MW | HPLC ret. time (min.) | HPLC condition | MS (M$^{+1}$) |
|---|---|---|---|---|---|
| 85 | 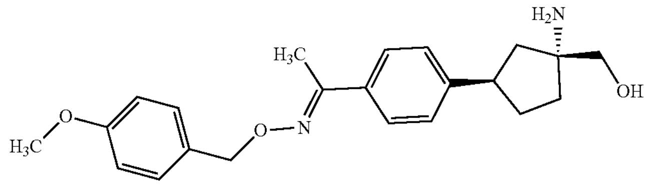 [SMILES: COc1ccc(CO/N=C(\C)c2ccc([C@@H]3CC[C@](N)(CO)C3)cc2)cc1] | 368.48 | 0.81 | KK | 369.3 |
| 86 | 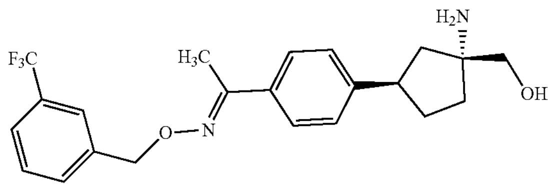 [SMILES: C/C(=N\OCc1cccc(C(F)(F)F)c1)c1ccc([C@@H]2CC[C@](N)(CO)C2)cc1] | 406.45 | 0.88 | KK | 407.3 |

The Examples in Table 7 were prepared according to the general procedure for Example 5 or Example 23

TABLE 7

| Ex. No. | Structure | MW | HPLC ret. time (min.) | HPLC condition | MS (M$^{+1}$) |
|---|---|---|---|---|---|
| 87 | 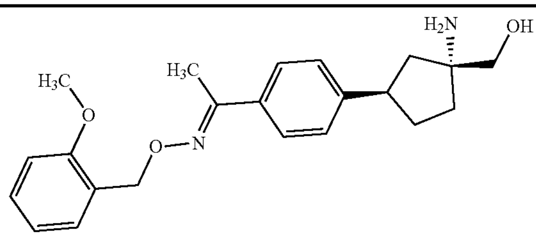 | 368.47 | 0.82 | KK | 369.2 |
| 88 | 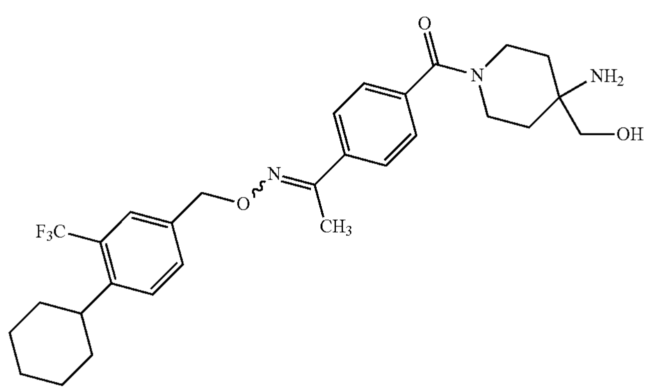 [SMILES: CC(=NOCc1ccc(C2CCCCC2)c(C(F)(F)F)c1)c1ccc(C(=O)N2CCC(N)(CO)CC2)cc1] | 531.62 | 1.03 | KK | 532.2 |

BIOLOGICAL ASSAYS

The compounds of Formula (I) or salts thereof engage their biological targets (e.g. S1P$_1$) after bioactivation through phosphorylation of the alcohol to provide active phosphate ester compounds of Formula (I) or salts thereof. In vitro characterization of biological activity of the examples was conducted on synthetically prepared samples of the phosphorylated compounds.

S1P1 Binding Assay:

Membranes were prepared from CHO cells expressing human S1P$_1$. Cells pellets (1×10$^9$ cells/pellet) were suspended in buffer containing 20 mM HEPES (4-(2-hydroxyethyl)-1-piperazineethanesulfonic acid), pH 7.5, 50 mM NaCl, 2 mM EDTA (ethylenediamine tetraacetic acid) and Protease Inhibitor cocktail (Roche), and disrupted on ice using the Polytron homogenizer. The homogenate was centrifuged at 20,000 rpm (48,000 g) and the supernatant was discarded. The membrane pellets were resuspended in buffer containing 50 mM HEPES, pH 7.5, 100 mM NaCl, 1 mM MgCl$_2$, 2 mM EDTA and stored in aliquots at −80° C. after protein concentration determination.

Membranes (2 μg/well) and 0.03 nM final concentration of $^{33}$P-S1P ligand (1 mCi/ml, Perkin Elmer or American Radiolabeled Chemicals) diluted in assay buffer (50 mM HEPES, pH7.4, 5 mM MgCl$_2$, 1 mM CaCl$_2$), 0.5% fatty acid free BSA (bovine serum albumin), 1 mM NaF) were added to the compound plates (384 Falcon v-bottom plate (0.5 µl/well in a 11 point, 3-fold dilution). Binding was performed for 45 minutes at room temperature, terminated by collecting the membranes onto 384-well Millipore FB filter plates, and radioactivity was measured by TOPCOUNT®. The competition data of the test compounds over a range of concentrations was plotted as percentage inhibition of radioligand specific binding. The $IC_{50}$ is defined as the concentration of competing ligand needed to reduce specific binding by 50%.

Receptor [$^{35}$S] GTPγS Binding Assays:

Compounds were loaded in a 384 Falcon v-bottom plate (0.5 µl/well in an 11 point, 3-fold dilution). Membranes prepared from $S1P_1$/CHO cells or EDG3-Gal5-bla HEK293T cells (EDG3 equivalent $S1P_3$) were added to the compound plate (40 l/well, final protein 3 µg/well) with MULTIDROP®. [$^{35}$S]GTP (1250 Ci/mmol, Perkin Elmer) was diluted in assay buffer: 20 mM HEPES, pH7.5, 10 mM $MgCl_2$, 150 mM NaCl, 1 mM EGTA (ethylene glycol tetraacetic acid), 1 mM DTT (Dithiothreitol), 10 µM GDP, 0.1% fatty acid free BSA, and 10 µg/ml Saponin to 0.4 nM. 40 µl of the [35S] GTP solution was added to the compound plate with a final concentration of 0.2 nM. The reaction was kept at room temperature for 45 min. At the end of incubation, all the mixtures in the compound plate were transferred to Millipore 384-well FB filter plates via the VELOCITY11® Vprep liquid handler. The filter plate was washed with water 4 times by using the manifold Embla plate washer and dried at 60° C. for 45 min. MicroScint 20 scintillation fluid (30 µl) was added to each well for counting on the Packard TOPCOUNT®. $EC_{50}$ is defined as the agonist concentration that corresponds to 50% of the Ymax (maximal response) obtained for each individual compound tested.

A smaller value for GTPγS $S1P_1$ $EC_{50}$ value indicated greater activity for the compound in the GTPγS $S1P_1$ binding assay. Thus the compounds of the present invention may be used in treating, preventing, or curing various $S1P_1$ receptor-related conditions. The compounds have potential use in treating, preventing, or curing autoimmune and inflammatory diseases such as multiple sclerosis, rheumatoid arthritis, inflammatory bowel disease, lupus, psoriasis, or minimizing or reducing rejection of transplanted organs.

TABLE A

| Ex. | $S1P_1$ Binding $IC_{50}$ (nM) | GTPγS $S1P_1$ $EC_{50}$ (nM) | GTPγS $S1P_3$ $EC_{50}$ (nM) |
|---|---|---|---|
| 38 | 283.5 | >30,000 | >30,000 |
| 39 | 864.8 | NA | NA |
| 40 | 28.3 | 38.1 | >60,000 |
| 41 | 20.0 | 25.3 | 773 |
| 42 | NA | 17.6 | >30,000 |
| 43 | NA | 26.4 | >30,000 |
| 44 | 15.1 | 20.3 | >60,000 |
| 45 | 2.7 | 5.6 | >60,000 |
| 46 | 5.2 | 11.2 | >60,000 |
| 50 | 563.4 | 630.2 | >60,000 |
| 52 | 31.9 | 1.1 | >30,000 |
| 54 | 14.2 | NA | NA |
| 55 | NA | 1557.0 | >60,000 |
| 56 | NA | 295.1 | >60,000 |
| 57 | 1873.4 | 324.5 | >60,000 |
| 58 | 10.7 | 60.8 | >3,125 |
| 59 | 10.5 | 136.3 | >3,125 |
| 60 | 28.4 | 434.1 | >6,250 |
| 61 | 125.7 | 203.9 | >6,250 |
| 62 | 1472.8 | 503.7 | >6,250 |
| 63 | 182.6 | 342.5 | >6,250 |
| 64 | 2530.4 | 500.4 | >6,250 |
| 65 | 1994.9 | 626.0 | >6,250 |
| 66 | 62.0 | 193.7 | 9375 |
| 67 | 120.4 | 754.1 | >18,000 |
| 68 | 361.6 | 399.4 | 9375 |
| 69 | 898.6 | 767.4 | 9375 |
| 70 | 917.9 | 406.5 | >18,000 |
| 71 | 219.3 | 242.3 | >18,000 |
| 72 | 61.6 | 91.5 | >30,000 |
| 73 | 49.6 | 44.4 | >30,000 |

Blood Lymphocyte Reduction (BLR) assay in rodent:

Lewis rats were dosed orally with vehicle alone (polyethylene glycol 300, "PEG300") or with the comparative compound 2-amino-2-[2-(4-octylphenyl)ethyl]-1,3-propanediol, hydrochloride ("FTY" CAS: 162359-6-0) as a solution in the vehicle at doses of 0.1 mg/kg, 0.5 mg/kg and 3.0 mg/kg. The results are provided in Table B and the level of lymphocyte reduction at 24 hours post-dose was maximal at 3.0 mg/kg. The percent reduction in lymphocytes is dose-related but the relationship is not linear, with non-proportional increases in dose being required to elicit sequentially greater reductions in lymphocyte counts. For example, in this study to demonstrate a change of 13% (from 69% reduction to 82% reduction) required escalation of five-fold in dose (from 0.1 mg/kg to 0.5 mg/kg). Furthermore, to demonstrate an additional change of 7% in this study (from 82% reduction to 89% reduction) required escalation of six-fold in dose (from 0.5 mg/kg to 3.0 mg/kg). As shown in Table C in a separate study, Example 3 at 10 mg/kg and 30 mg/kg drove a maximal level of lymphocyte reduction comparable to the reduction shown by FTY.

TABLE B 2-amino-2-[2-(4-octylphenl)pethyl]-1,3-propanediol, hydrochloride

Rat Blood Lymphocyte Reduction Assay at 24 hr post-dose

| Dosage (mg/kg) | Compound | | Vehicle Control | | Percent reduction vs. control |
|---|---|---|---|---|---|
| | Mean | SEM | Mean | SEM | |
| 0.1 | 2.78 | 0.17 | 9.01 | 0.19 | 69% |
| 0.5 | 1.64 | 0.25 | 9.01 | 0.19 | 82% |
| 3.0 | 1.02 | 0.06 | 9.01 | 0.19 | 89% |

TABLE C

| Example No. | Dosage (mg/kg) | Rat Blood Lymphocyte Reduction Assay at 24 hr post-dose Percent reduction vs. vehicle control |
|---|---|---|
| 3 | 0.3 | 29% |
| 3 | 1 | 62% |
| 3 | 10 | 85% |
| 3 | 30 | 85% |
| FTY | 3 | 87% |

Pulmonary Toxicity Assay

The analysis of protein levels in bronchoalveolar lavage (BAL) fluid obtained from an animal were used to gauge pulmonary side effects. Increased levels of protein in BAL fluid were indicative of undesired edematous pulmonary effects, such as pulmonary edema.

Example 3 was administered orally to rats at doses of 0.3, 1.0, 10, 30 mg/kg and 2-amino-2-[2-(4-octylphenyl)ethyl]-1,3-propanediol, hydrochloride (CAS: 162359-56-0) was administered at 3.0 mg/kg as a solution in the vehicle. At 24 hours post dose, the rats were then euthanized by barbiturate overdose. The trachea was exposed by incision of the overlying skin and then cannulated. The lungs were lavaged with 4 mL of saline. The recovered lavage fluid was assayed for total protein content. The concentration of the BAL protein in the recovered BAL fluid was determined on an Advia 1800 Chemistry Analyzer (Siemens Healthcare Diagnostics). The results of the bronchoalveolar lavage (BAL) assay are shown in Table 5. The results represent the average results of all animals within each treatment group (n=2-4).

TABLE D

| Example No. | Dosage (mg/kg) | BAL protein level (mg/dL) (24 hr post-dose) Relative BAL protein vs. control |
|---|---|---|
| 3 | 0.3 | 0.8 |
| 3 | 1 | 0.8 |
| 3 | 10 | 1.2 |
| 3 | 30 | 1.3 |
| FTY | 3 | 1.8 |

Table D shows the relative BAL protein levels at 24 hours for the tested compounds compared to the administration of vehicle only. In this study, as reported in Table D, Example 3 could be administered up to 10 mg/kg with an elevation of just 1.2 fold or up to 30 mg/kg with an elevation of 1.3 fold whereas comparative compound 2-amino-2-[2-(4-octylphenyl)ethyl]-1,3-propanediol when administered at at 3 mg/kg led to a relative BAL increase of 1.8 fold indicating increased pulmonary toxicity.

What is claimed is:
1. A compound of Formula (I):

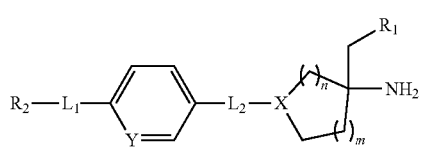

or a salt thereof, wherein:
X is CH or N;
Y is CH or N;
$R_1$ is —OH or —OP(O)(OH)$_2$;
$L_1$ is —CR$_3$=N—O—CR$_a$R$_a$— or —CR$_a$R$_a$—O—N=CR$_3$—;
$L_2$ is a bond, —C(O)—, or —S(O)$_2$—;
$R_2$ is $C_{1-4}$ alkyl, —CH=CH$_2$, $C_{3-6}$ cycloalkyl, —(CH$_2$)$_p$-A, or —CH$_2$O-A;
A is phenyl substituted with zero to 2 substituents independently selected from F, $C_1$, $C_{1-2}$ alkyl, —CF$_3$, —NO$_2$, —O($C_{1-2}$ alkyl), and $C_{3-6}$ cycloalkyl;
$R_3$ is H, $C_{1-2}$ alkyl, or —CF$_3$;
each $R_a$ is independently H or —CH$_3$;
m is 1 or 2;
n is 1 or 2; provided that n+m is 2 or 3; and
p is zero, 1, or 2.
2. The compound according to claim 1 or a salt thereof, wherein Y is CH.

3. The compound according to claim 1 or a salt thereof, wherein:
X is CH;
$L_2$ is a bond;
m is 1; and
n is 1.
4. The compound according to claim 3 or a salt thereof, wherein:
$R_2$ is —CH$_3$, —CH$_2$CH$_2$CH$_3$, $C_{3-6}$ cycloalkyl, or —(CH$_2$)$_p$-A; and
A is phenyl substituted with zero to 2 substituents independently selected from F, —CF$_3$, —NO$_2$, —OCH$_3$, and cyclohexyl.
5. The compound according to claim 1 or a salt thereof, wherein:
X is N;
Y is CH;
$L_1$ is —CR$_3$=NO—CH$_2$—; and
$L_2$ is —C(O)— or —S(O)$_2$—.
6. The compound according to claim 5 or a salt thereof, wherein:
$R_2$ is —(CH$_2$)$_p$-A; and
A is phenyl substituted with zero to 2 substituents independently selected from —CF$_3$ and cyclohexyl.
7. The compound according to claim 1 or a salt thereof, wherein said compound is:
1-(4-(3-amino-3-(hydroxymethyl)cyclopentyl)phenyl) ethanone O-phenethyl oxime (1-4); 1-(4-((1R,3R)-3-amino-3-(hydroxymethyl)cyclopentyl)phenyl)ethanone O-benzyl oxime, TFA (5);
1-(4-((1R,3R)-3-amino-3-(hydroxymethyl)cyclopentyl) phenyl)ethan-1-one O-cyclopropylmethyl oxime (6);
(E)-1-(4-((1R,3R)-3-amino-3-(hydroxymethyl)cyclopentyl)phenyl)ethan-1-one O-(4-cyclohexyl-3-(trifluoromethyl)benzyl) oxime (7);
1-(4-((1R,3R)-3-amino-3-(hydroxymethyl)cyclopentyl) phenyl)ethan-1-one O-(3-phenylpropyl) oxime (8);
1-(4-((1R,3R)-3-amino-3-(hydroxymethyl)cyclopentyl) phenyl)ethan-1-one O-(4-nitrobenzyl) oxime (9);
1-(4-((1R,3R)-3-amino-3-(hydroxymethyl)cyclopentyl) phenyl)ethan-1-one O-(4-fluorobenzyl) oxime (10);
1-(4-((1R,3R)-3-amino-3-(hydroxymethyl)cyclopentyl) phenyl)ethan-1-one O-cyclohexylmethyl oxime (11);
1-(4-((1S,3R)-3-amino-3-(hydroxymethyl)cyclopentyl) phenyl)ethan-1-one O-(3-methoxybenzyl) oxime (12);
1-(4-((1S,3R)-3-amino-3-(hydroxymethyl)cyclopentyl) phenyl)ethan-1-one O-(2-methoxybenzyl) oxime (13);
1-(4-((1S,3R)-3-amino-3-(hydroxymethyl)cyclopentyl) phenyl)ethan-1-one O-butyl oxime (14);
(E)-acetophenone O-(4-((1R,3R)-3-amino-3-(hydroxymethyl)cyclopentyl)benzyl) oxime, TFA (15);
(E)-1-phenylethan-1-one O-(4-((1S,3R)-3-amino-3-(hydroxymethyl)cyclopentyl) benzyl) oxime (16);
(E)-1-(3-methoxyphenyl)ethan-1-one O-(4-((1S,3R)-3-amino-3-(hydroxymethyl) cyclopentyl)benzyl) oxime (17);
(E)-3-methoxybenzaldehyde 0-(4-((1S,3R)-3-amino-3-(hydroxymethyl)cyclopentyl) benzyl) oxime (18);
ethyl 4-(6-acetylpyridin-3-yl)-1-aminocyclopent-2-enecarboxylate (19-20);
(3-amino-3-(hydroxymethyl)pyrrolidin-1-yl)(4-(1-(phenethoxyimino)ethyl)phenyl) methanone (21 and 22);
(3-amino-3-(hydroxymethyl)pyrrolidin-1-yl)(4-(1-((3-phenylpropoxy)imino)ethyl) phenyl)methanone, TFA (23 and 24);

(3-amino-3-(hydroxymethyl)pyrrolidin-1-yl)(4-(1-(((4-cyclohexyl-3-(trifluoromethyl) benzyl)oxy)imino)ethyl)phenyl)methanone (25-26);
(3-amino-3-(hydroxymethyl)pyrrolidin-1-yl)(4-(1-((3-phenylpropoxy)imino)propyl) phenyl)methanone (27-28);
(3-amino-3-(hydroxymethyl)piperidin-1-yl)(4-(1-((3-phenylpropoxy)imino)ethyl) phenyl)methanone (29-30);
(3-amino-3-(hydroxymethyl)piperidin-1-yl)(4-(1-(((4-cyclohexyl-3-(trifluoromethyl) benzyl)oxy)imino)ethyl)phenyl)methanone (31-32);
(3-amino-3-(hydroxymethyl)piperidin-1-yl)(4-(1-(phenethoxyimino)ethyl)phenyl) methanone (33);
(4-amino-4-(hydroxymethyl)piperidin-1-yl)(4-(1-((3-phenylpropoxy)imino)ethyl) phenyl)methanone (34);
(3-amino-3-(hydroxymethyl)pyrrolidin-1-yl)(4-(2,2,2-trifluoro-1-((3-phenylpropoxy) imino)ethyl)phenyl)methanone (35);
(E)-1-(4-((4-amino-4-(hydroxymethyl)piperidin-1-yl)sulfonyl)phenyl)ethanone O-(3-phenylpropyl)oxime, TFA (36);
1-(4-((4-amino-4-(hydroxymethyl)piperidin-1-yl)sulfonyl)phenyl)ethan-1-one O-(4-cyclohexyl-3-(trifluoromethyl)benzyl) oxime (37);
(E)-1-(4-(3-amino-3-(hydroxymethyl)cyclopentyl)phenyl)ethan-1-one O-phenethyl oxime (74);
(E)-1-(4-((1S,3R)-3-amino-3-(hydroxymethyl)cyclopentyl)phenyl)ethan-1-one O-(3-phenylpropyl) oxime (75);
(E)-1-(4-((1R,3R)-3-amino-3-(hydroxymethyl)cyclopentyl)phenyl)ethan-1-one O-(4-(trifluoromethyl)benzyl) oxime (76);
(E)-1-(4-((1R,3R)-3-amino-3-(hydroxymethyl)cyclopentyl)phenyl)ethan-1-one O-(2-phenoxyethyl) oxime (77);
(E)-1-(4-((1R,3R)-3-amino-3-(hydroxymethyl)cyclopentyl)phenyl)ethan-1-one O-(2-(3-(trifluoromethyl)phenoxy)ethyl) oxime (78);
(E)-1-(4-((1R,3R)-3-amino-3-(hydroxymethyl)cyclopentyl)phenyl)ethan-1-one O-allyl oxime (79);
(E)-1-(4-((1R,3R)-3-amino-3-(hydroxymethyl)cyclopentyl)phenyl)ethan-1-one O-isopropyl oxime (80);
(E)-1-(4-((1R,3R)-3-amino-3-(hydroxymethyl)cyclopentyl)phenyl)ethan-1-one O-(tert-butyl) oxime (81);
(E)-1-(4-((1R,3R)-3-amino-3-(hydroxymethyl)cyclopentyl)phenyl)ethan-1-one O-(3-fluorobenzyl) oxime (82);
(E)-1-(4-((1R,3R)-3-amino-3-(hydroxymethyl)cyclopentyl)phenyl)ethan-1-one O-phenyl oxime (83);
(E)-1-(4-((1R,3R)-3-amino-3-(hydroxymethyl)cyclopentyl)phenyl)ethan-1-one O-(3-methoxybenzyl) oxime (84);
(E)-1-(4-((1R,3R)-3-amino-3-(hydroxymethyl)cyclopentyl)phenyl)ethan-1-one O-(4-methoxybenzyl) oxime (85);
(E)-1-(4-((1R,3R)-3-amino-3-(hydroxymethyl)cyclopentyl)phenyl)ethan-1-one O-(3-(trifluoromethyl)benzyl) oxime (86);
(E)-1-(4-((1R,3R)-3-amino-3-(hydroxymethyl)cyclopentyl)phenyl)ethan-1-one O-(2-methoxybenzyl) oxime (87); or
(4-amino-4-(hydroxymethyl)piperidin-1-yl)(4-(1-(((4-cyclohexyl-3-(trifluoromethyl)benzyl)oxy)imino)ethyl)phenyl)methanone (88).

8. The compound according to claim 1 wherein said compound is:
((1R,3R)-1-amino-3-(4-(1-((cyclopropylmethoxy)imino)ethyl)phenyl)cyclopentyl) methyl dihydrogen phosphate (38);
((1R,3R)-1-amino-3-(4-(1-((benzyloxy)imino)ethyl)phenyl)cyclopentyl)methyl dihydrogen phosphate (39);
((1R,3R)-1-amino-3-(4-((E)-1-(((4-cyclohexyl-3-(trifluoromethyl)benzyl)oxy) imino)ethyl)phenyl)cyclopentyl)methyl dihydrogen phosphate (40);
((1R,3R)-1-amino-3-(4-((E)-1-((3-phenylpropoxy)imino)ethyl)phenyl)cyclopentyl) methyl dihydrogen phosphate (41);
((1R,3R)-1-amino-3-(4-(1-(((4-nitrobenzyl)oxy)imino)ethyl)phenyl)cyclopentyl) methyl dihydrogen phosphate (42);
((1R,3R)-1-amino-3-(4-(1-(((4-fluorobenzyl)oxy)imino)ethyl)phenyl)cyclopentyl) methyl dihydrogen phosphate (43);
((1R,3R)-1-amino-3-(4-(1-(((4-fluorobenzyl)oxy)imino)ethyl)phenyl)cyclopentyl) methyl dihydrogen phosphate (44);
((1R,3R)-1-amino-3-(4-(1-(((4-(trifluoromethyl)benzyl)oxy)imino)ethyl)phenyl) cyclopentyl)methyl dihydrogen phosphate (45);
((1R,3R)-1-amino-3-(4-(1-((2-phenoxyethoxy)imino)ethyl)phenyl)cyclopentyl) methyl dihydrogen phosphate (46);
((1R,3R)-1-amino-3-(4-(1-((2-(3-(trifluoromethyl)phenoxy)ethoxy)imino)ethyl) phenyl)cyclopentyl)methyl dihydrogen phosphate (47);
((1R,3R)-1-amino-3-(4-(1-(((3-fluorobenzyl)oxy)imino)ethyl)phenyl)cyclopentyl) methyl dihydrogen phosphate (48);
((1R,3R)-1-amino-3-(4-((E)-1-(((2-methoxybenzyl)oxy)imino)ethyl)phenyl) cyclopentyl)methyl dihydrogen phosphate (49);
((1R,3R)-1-amino-3-(4-((E)-1-(((3-methoxybenzyl)oxy)imino)ethyl)phenyl) cyclopentyl)methyl dihydrogen phosphate (50);
((1R,3R)-1-amino-3-(4-((E)-1-(((3-(trifluoromethyl)benzyl)oxy)imino)ethyl)phenyl) cyclopentyl)methyl dihydrogen phosphate (51);
((1R,3S)-1-amino-3-(4-(((((E)-1-(3-methoxyphenyl)ethylidene)amino)oxy)methyl) phenyl)cyclopentyl) methyl dihydrogen phosphate (52);
((1R,3S)-1-amino-3-(4-(((((E)-1-(3-methoxyphenyl)ethylidene)amino)oxy)methyl) phenyl)cyclopentyl) methyl dihydrogen phosphate (53);
((1R,3S)-1-amino-3-(4-(((((E)-1-(3-methoxyphenyl)ethylidene)amino)oxy)methyl) phenyl)cyclopentyl) methyl dihydrogen phosphate (54);
(3-amino-1-(4-(1-(phenethoxyimino)ethyl)benzoyl)pyrrolidin-3-yl)methyl dihydrogen phosphate (55);
(4-amino-1-(4-(1-(phenethoxyimino)ethyl)benzoyl)piperidin-4-yl)methyl dihydrogen phosphate (56);
(4-amino-1-(4-(1-((3-phenylpropoxy)imino)ethyl)benzoyl)piperidin-4-yl)methyl dihydrogen phosphate (57);
(E)-(4-amino-1-(4-(1-(((4-cyclohexyl-3-(trifluoromethyl)benzyl)oxy)imino)ethyl) benzoyl)piperidin-4-yl) methyl dihydrogen phosphate (58);
(E)-(3-amino-1-(4-(1-(((4-cyclohexyl-3-(trifluoromethyl)benzyl)oxy)imino)ethyl) benzoyl)pyrrolidin-3-yl) methyl dihydrogen phosphate (59-60);
(E)-(3-amino-1-(4-(1-((3-phenylpropoxy)imino)ethyl)benzoyl)pyrrolidin-3-yl)methyl dihydrogen phosphate (61-62);

(E)-(3-amino-1-(4-(1-((3-phenylpropoxy)imino)propyl)benzoyl)pyrrolidin-3-yl) methyl dihydrogen phosphate (63-64);

(Z)-(3-amino-1-(4-(2,2,2-trifluoro-1-((3-phenylpropoxy)imino)ethyl)benzoyl) pyrrolidin-3-yl)methyl dihydrogen phosphate (65);

(E)-(3-amino-1-(4-(1-(((4-cyclohexyl-3-(trifluoromethyl)benzyl)oxy)imino)ethyl) benzoyl)piperidin-3-yl) methyl dihydrogen phosphate (66-67);

(E)-(3-amino-1-(4-(1-((3-phenylpropoxy)imino)ethyl)benzoyl)piperidin-3-yl)methyl dihydrogen phosphate (68-69);

(E)-(4-amino-1-((4-(1-(((4-cyclohexyl-3-(trifluoromethyl)benzyl)oxy)imino)ethyl) phenyl)sulfonyl)piperidin-4-yl)methyl dihydrogen phosphate (70);

(E)-(4-amino-1-((4-(1-((3-phenylpropoxy)imino)ethyl)phenyl)sulfonyl)piperidin-4-yl)methyl dihydrogen phosphate (71); or ((1R,3R)-1-amino-3-(4-((E)-1-(phenethoxyimino)ethyl)phenyl)cyclopentyl)methyl dihydrogen phosphate (72-73).

9. A pharmaceutical composition comprising a compound according to claim 1 or a pharmaceutically-acceptable salt thereof; and a pharmaceutically acceptable carrier.

10. A method of treating an autoimmune disease or a chronic inflammatory disease, comprising administering to a mammalian patient a compound according to claim 1 or a pharmaceutically acceptable salt thereof.

11. The method according to claim 10 wherein said autoimmune disease or a chronic inflammatory disease is selected from lupus, multiple sclerosis, inflammatory bowel disease, Sjögren's syndrome, and rheumatoid arthritis.

12. The compound according to claim 1 wherein said compound is:

$L_2$ is a bond.

13. The compound according to claim 1 wherein said compound is:

$L_2$ is —C(O)— or —S(O)$_2$—.

* * * * *

UNITED STATES PATENT AND TRADEMARK OFFICE
CERTIFICATE OF CORRECTION

PATENT NO. : 11,059,784 B2  
APPLICATION NO. : 16/636662  
DATED : July 13, 2021  
INVENTOR(S) : Alaric Dyckman et al.

Page 1 of 1

It is certified that error appears in the above-identified patent and that said Letters Patent is hereby corrected as shown below:

On the Title Page

Column 2 (Item (57) Abstract), Line 3, delete "L" and insert -- $L_1$ --, therefor.

Column 2 (Item (57) Abstract), Line 4, delete "$CR_aR$" and insert -- $CR_aR_a$ --, therefor.

In the Claims

Claim 1, Column 83, Line 59, delete "$C_1$" and insert -- Cl --, therefor.

Claim 5, Column 84, Line 19, delete "NO" and insert -- N-O --, therefor.

Claim 7, Column 84, Line 58, delete "0-(" and insert -- O-( --, therefor.

Signed and Sealed this  
Second Day of September, 2025

Coke Morgan Stewart  
*Acting Director of the United States Patent and Trademark Office*